(12) United States Patent
Niculescu

(10) Patent No.: US 11,047,009 B2
(45) Date of Patent: Jun. 29, 2021

(54) BLOOD BIOMARKERS FOR SUICIDALITY

(71) Applicants: Indiana University Research and Technology Corporation, Indianapolis, IN (US); United States Government as Represented by the Department of Veterans Affairs, Washington, DC (US)

(72) Inventor: Alexander B. Niculescu, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 788 days.

(21) Appl. No.: 15/091,706

(22) Filed: Apr. 6, 2016

(65) Prior Publication Data

US 2016/0215346 A1 Jul. 28, 2016

Related U.S. Application Data

(63) Continuation of application No. 14/194,024, filed on Feb. 28, 2014, now abandoned.

(60) Provisional application No. 61/770,696, filed on Feb. 28, 2013.

(51) Int. Cl.
*C12Q 1/6883* (2018.01)
*G01N 33/68* (2006.01)
*G01N 33/94* (2006.01)

(52) U.S. Cl.
CPC ....... *C12Q 1/6883* (2013.01); *G01N 33/6893* (2013.01); *G01N 33/9466* (2013.01); *C12Q 2600/158* (2013.01); *G01N 2800/304* (2013.01); *G01N 2800/52* (2013.01)

(58) Field of Classification Search
CPC ............ C12Q 1/6883; C12Q 2600/158; G01N 33/9466; G01N 33/6893; G01N 2800/304; G01N 2800/52
See application file for complete search history.

(56) References Cited

U.S. PATENT DOCUMENTS

| | | |
|---|---|---|
| 8,401,801 B2 | 3/2013 | Mrazek et al. |
| 8,688,385 B2 | 4/2014 | Mrazek et al. |
| 10,196,693 B2 | 2/2019 | Peterson et al. |
| 2005/0282911 A1 | 12/2005 | Hakkarainen et al. |
| 2012/0041911 A1 | 2/2012 | Pestian et al. |
| 2012/0269906 A1 | 10/2012 | Sheehan et al. |
| 2013/0142776 A1 | 6/2013 | Blumenfeld |
| 2013/0330429 A1 | 12/2013 | Vuckovic |
| 2014/0235663 A1 | 8/2014 | Yovell |
| 2014/0243211 A1 | 8/2014 | Niculescu |
| 2016/0153044 A1 | 6/2016 | Kaminsky et al. |
| 2018/0181701 A1 | 6/2018 | Niculescu |
| 2020/0312425 A1 | 10/2020 | Niculescu |
| 2020/0318188 A1 | 10/2020 | Niculescu |

FOREIGN PATENT DOCUMENTS

| | | |
|---|---|---|
| WO | 2015/006645 A1 | 1/2015 |
| WO | 2016/201299 A1 | 12/2016 |

OTHER PUBLICATIONS

Belzeaux et al. (2010) "Clinical variations modulate patterns of gene expression and define blood biomarkers in major depression" Journal of Psychiatric Research 44(16):1205-1213.*
Ayalew M. et al., "Convergent functional genomics of schizophrenia: from comprehensive understanding to genetic risk prediction," Molecular Psychiatry 17, pp. 887-905, doi:l0.1 038/mp.2012.37 (2012).
Benedelli et al., Opposite effects of suicidality and lithium on gray mailer volumes in bipolar depression. J Affect Disord 135, pp. 139-147, doi:l 0.1016/j.jad.2011.07.006 (2011).
Berngruber, T., et al., Evolution of suicide as a defence strategy against pathogens in a spatially structured environment. Ecol Lell (2013).
Chen, G. G., L. M. Fiori, et al. "Evidence of altered polyamine concentrations in cerebral cortex of suicide completers." Neuropsychopharmacology 35(7): 1477-1484 (2010).
Duckworth CA et al., "CD24 is expressed in gastric parietal cells and regulates apoptosis and the response to Helicobacter felis infection in the murine stomach," American Journal of Physiology, Gastrointestinal and Liver Physiology 303, G915-926, doi:10.1152/ajpgi.00068.2012 (2012).
Dwivedi, Y.,et al. "Modulation in activation and expression of phosphatase and tensin homolog on chromosome ten, Aktl, and 3-phosphoinositide-dependent kinase 1: further evidence demonstrating altered phosphoinositide 3-kinase signaling in postmortem brain of suicide subjects." Bioi Psychiatry 67(11): pp. 1017-1025 (2010).
Falcone et al. (2010) "Serum S100B: A Potential Biomarker for Suicidality in Adolescents?" PLoS One 5(6): e11 089.
Fiori et al., Global gene expression profiling of the polyamine system in suicide completers. Int. J. Neuropsychopharmacol. 14, 595-605, doi:10.1017/S146114571 0001574 (2011).
Fiori, L. M., et al. "Identification and characterization of spermidine/spermine N1-acetyltransferase promoter variants in suicide completers." Bioi Psychiatry 66(5): 460-467 (2009).
Fiori. L. M. et al., "Epigenetic regulation of spermidinelspermine n. acetyltransferase (SATI) in suicide." J Psychiatr Res 45(9): pp. 1229-1235 (2011).
Fori. L. M .. B. Wanner. et al. "Association of polyaminergic loci with anxiety, mood disorders, and attempted suicide." PLoS One 5(11): e15146 (2010).
Fiori, L. M., et at., (2011). "X chromosome and suicide." Mol Psychiatry 16(2): pp. 216-226.
Galfalvy, H., et al. (2013). "A pilot genome wide association and gene expression array study of suicide with and without major depression." World J Bioi Psychiatry.

(Continued)

*Primary Examiner* — Olga N Chernyshev
(74) *Attorney, Agent, or Firm* — Faegre Drinker Biddle & Reath LLP

(57) ABSTRACT

Biomarkers and methods for screening expression levels of the biomarkers for predicting and tracking suicidality, as well as for monitoring response to a treatment for suicidal risk and for determining suicidal risk as a side-effect of an antidepressant are disclosed.

3 Claims, 18 Drawing Sheets

(56) References Cited

OTHER PUBLICATIONS

Gaiteri C, et al., Altered gene synchrony suggests a combined hormone-mediated dysregulated state in major depression. PLoS One; 5(4): e9970.

Guipponi, M., et al. (2008). "Genetic and epigenetic analysis of SSAT gene dysregulation in suicidal behavior." Am J Med Genet B Neuropsychiatr Genet 150B(6): pp. 799-807.

Hakak Y, et al. Genome-wide expression analysis reveals dysregulation of myelination-related genes in chronic schizophrenia. Proc Natl Acad Sci USA 2001; 98(8): pp. 4746-4751.

Karege F. et al., Alteration in kinase activity but not in protein levels of protein kinase B and glycogen synthase kinase-3beta in ventral prefrontal cortex of depressed suicide victims. Biol Psychiatry 61, pp. 240-245, doi:10.1016/j.biopsych.2006.04.036 (2007).

Karege F., et al. Alterations in phosphatidylinositol 3-kinase activity and PTEN phosphatase in the prefrontal cortex of depressed suicide victims. Neuropsychobiology 2011; 63(4): pp. 224-231.

Kelleher, I., F. Lynch, et al. (2012). "Psychotic Symptoms in Adolescence Index Risk for Suicidal Behavior: Findings From 2 Population-Based Case-Control Clinical Interview Studies." Arch Gen Psychiatry: 1-7.

Kim, S., et al. (2007). "Suicide candidate genes associated with bipolar disorder and schizophrenia: an exploratory gene expression profiling analysis of post-mortem prefrontal cortex." BMC Genomics 8: 413.

Klempan, T. A., et al. (2008). "Profiling brain expression of the spermidine/spermine N1-acetyltransferase 1 (SAT1) gene in suicide." Am J Med Genet B Neuropsychiatr Genet 150B(7): pp. 934-943.

Klempan, T. A., et at. (2009). "Altered expression of genes involved in ATP biosynthesis and GABAergic neurotransmission in the ventral prefrontal cortex of suicides with and without major depression." Mol Psychiatry 14(2): pp. 175-189.

Kurian S.M. et al., "Identification of blood biomarkers for psychosis using convergent functional genomics," Molecular Psychiatry 16, pp. 37-58, doi:10.1038/mp.2009.117 (2011).

Lalovic, A., T. Klempan, et al. (2010). "Altered expression of lipid metabolism and immune response genes in the frontal cortex of suicide completers." J Affect Disord 120(1-3): pp. 24-31.

Le-Niculescu H. et al., "Phenomic, convergent functional genomic, and biomarker studies in a stress-reactive genetic animal model of bipolar disorder and co-morbid alcoholism," American Journal of Medical Genetics, Part B, Neuropsychiatric genetics: the official publication of the International Society of Psychiatric Genetics 147B, pp. 134-166, doi:10.1002/ajmg.b.30707 (2008).

Le-Niculescu, H., et al. (2007). Towards understanding the schizophrenia code: an expanded 33 convergent functional genomics approach. American journal of medical genetics. Part B, Neuropsychiatric genetics: the official publication of the International Society of Psychiatric Genetics 144B(2): pp. 129-158.

Le-Niculescu, H., et al. (2011). "Convergent functional genomic studies of omega-3 fatty acids in stress reactivity, bipolar disorder and alcoholism." Translational Psychiatry 1: e4.

Le-Niculescu, H., et al. (2009). "Convergent functional genomics of genome-wide association data for bipolar disorder: comprehensive identification of candidate genes, pathways and mechanisms." American journal of medical genetics. Part B, Neuropsychiatric genetics: the official publication of the International Society of Psychiatric Genetics 150B(2): pp. 155-181.

Le-Niculescu, H., et at. (2010). "Convergent integration of animal model and human studies of bipolar disorder (manic-depressive illness)." Curr Opin Pharmacol 10(5): pp. 594-600.

Le-Niculescu H. et al., "Discovery and validation of blood biomarkers for suicidality", Molecular Psychiatry (2013), pp. 1-16.

Le-Niculescu H. et al., "Identifying blood biomarkers for mood disorders using convergent functional genomics," Molecular Psychiatry 14, pp. 156-174, doi:10.. 1111/ele.12064 (2009).

Lewis MD. et al., "Suicide deaths of active-duty US military and omega-3 fatty-acid status: a case-control comparison," J Clin Psychiatry 72, pp. 1585-1590, doi:10A088/JCP.11m06879 (2011).

Lowthert et al., Increased ratio of anti-apoptotic to pro-apoptotic Bcl2 gene-family members in lithium-responders one month after treatment initiation. Biology of Mood & Anxiety Disorders 2, 15, doi:10.1186/2045-5380-2-15 (2012).

Malkesman et al. Targeting the BH3-interacting domain death agonist to develop mechanistically unique antidepressants. Mol. Psychiatry 17, pp. 770-780, doi:10.1038/mp.2011.77 (2012).

Margoob et al. (2004) "Serum Cholesterol Level and Suicidal Attempts—Kashmir Scenario" JK—Practitioner 11 (3): pp. 171-177.

Menke, A., et al. (2012). "Genome-wide association study of antidepressant treatment-emergent suicidal ideation." Neuropsychopharmacology 37(3): pp. 797-807.

Miller BH, et al. MicroRNA-132 dysregulation in schizophrenia has implications for both neurodevelopment and adult brain function. Proc Natl Acad Sci USA 2012; 109(8): pp. 3125-3130.

Min et al., Altered levels of growth-related and novel gene transcripts in reproductive and other tissues of female mice overexpressing spermidien/spermine N1-actyltransferase (SSAT). J. Biol. Chem. 277, pp. 3647-3657, doi:l0.1074/ibc.MI100751200 (2002).

Mudge J., et al. Genomic convergence analysis of schizophrenia: mRNA sequencing reveals altered synaptic vesicular transport in post-mortem cerebellum. PLoS One 2008; 3(11): e3625.

Niculescu, A. B., et al. (2000). "Identifying a series of candidate genes for mania and psychosis: a convergent functional genomics approach." Physiological genomics 4(1): pp. 83-91.

Niculescu, A. B. et al., (2010). "Convergent Functional Genomics: what we have learned and can learn about genes, pathways, and mechanisms." Neuropsychopharmacology 35(1): pp. 355-356.

Niculescu, et al., PhenoChipping of psychotic disorders: a novel approach for deconstructing and quantitating 11 psychiatric phenotypes. American Journal of Medical Genetics. Part B, Neuropsychiatric genetics: the official publication of the International Society of Psychiatric Genetics 141 B, pp. 653-662, doi:10.1002/ajmg.b.30404 (2006).

Nock, M. K., G. Borges, et al. (2008). "Suicide and suicidal behavior." Epidemiol Rev 30: pp. 133-154.

Ogden, C. A., et at. (2004). "Candidate genes, pathways and mechanisms for bipolar (manic-depressive) and related disorders: an expanded convergent functional genomics approach." Molecular psychiatry 9(11): pp. 1007-1029.

Oquendo, M. A., et al. (2010). "Increased risk for suicidal behavior in comorbid bipolar disorder and alcohol use disorders: results from the National Epidemiologic Survey on Alcohol and Related Conditions (NESARC)." The Journal of clinical psychiatry 71 (7): pp. 902-909.

Pandey, G. N., et al. (2003). "Altered expression and phosphorylation of myristoylated alanine-rich C kinase substrate (MARCKS) in postmortem brain of suicide victims with or without depression." J Psychiatr Res 37(5): pp. 421-432.

Pandey, G. N., et al. (2012). "Proinflammatory cytokines in the prefrontal cortex of teenage suicide victims." J Psychiatr Res 46(1): pp. 57-63.

Patel S.D. et al., "Coming to grips with complex disorders: genetic risk prediction in bipolar disorder using panels of genes identified through convergence functional genomics," American Journal of Medical Genetics Part b, Neuropsychiatric genetics: the official publication of the International Society of Psychiatric genetics 153B, pp. 850-877, doi:10.1 pp2/ajmg.b.31087 (2010).

Pietila et al., Activation of polyamine catabolism profoundly alters tissue polyamine pools and affects hair growth and female fertility in transgenic mice overexpressing spermidine/spermine N1-acetyltransferase. J Biol. Chem. 272, D18746-18751 (1997).

Sequeira A. et al., Gene expression changes in the prefrontal cortex, anterior cingulate cortex and nucleusaccumbens of mood disorders subjects that committed suicide, PloS one 7, e35367, doi:10, 10,1371/journal, pone.0035367 (2012).

Sequeira. A., et al. (2006). "Implication of SSAT by gene expression and genetic variation in suicide and major depression." Arch Gen Psychiatry 63(1): pp. 35-48.

(56) References Cited

OTHER PUBLICATIONS

Sequeira, A., et al. (2007). "Patterns of gene expression in the limbic system of suicides with and without major depression." Mol Psychiatry 12(7): pp. 640-655.

Sequeira, A., et al. (2009). "Global brain gene expression analysis links glutamatergic and GABAergic alterations to suicide and major depression." PLoS One 4(8): e6585 (2010).

Sublette M. et al., "Omega-3 polyunsaturated essential fatty acid status as a predictor of future suicide risk," Am J Psychiatry 163, pp. 1100-1102, doi:10.1176/appi.ajp.163.6.110 (2006).

Bertone-Johnson et al., Vitamin D and the Occurrence of Depression: Casual Associate or Circumstantial Evidence?; Nutr Ref. 2009, August, vol. 67, No. 8, pp. 481-492.

Brent et al. "Pharmacogenomics of Suicidal Events. Pharmacogenomics.", Jun. 2010; vol. 11, No. 6; pp. 1-20;.

Brucker et al., "Assessing Risk of Future Suicidality in Emergency Department Patients," Acad. Emerg. Med., (2019), 26(4):376-383.

International Preliminary Report on Patentability received for PCT Patent Application No. PCT/US2016/036985, dated Dec. 21, 2017, 12 pages.

International Preliminary Report on Patentability received for PCT Patent Application No. PCT/US2018/032540, dated Nov. 21, 2019, 9 pages.

International Search Report and Written Opinion received for PCT Patent Application No. PCT/US2016/036985, dated Sep. 9, 2016, 12 pages.

International Search Report and Written Opinion received for PCT Patent Application No. PCT/US2018/032540, dated Sep. 14, 2018, 11 pages.

Johnson, Erb, "Vitamin D and the Occurrence of Depression: Casual Association or Circumstantial Evidence?", Nutrition Reviews. Aug. 2009; vol. 67, No. 8; pp. 1-17.

Le-Niculescu et al., Molecular Psychiatry, 2013, 18:1249-64.

Levey et al., "Towards understanding and predicting suicidality in women: biomarkers and clinical risk assessment", Molecular Psychiatry, vol. 21, No. 6, Apr. 5, 2016, pp. 768-785.

Mudge et al., Genomic Convergence Analysis of Schizophrenia: mRNA Sequencing Reveals Altered Synaptic Vesicular Transport in Post-Mortem Cerebellum, PLoS ONE, (2008) 11(3):e3625.

Niculescu et al., "Dissecting Suicidality Using a Combined Genomic and Clinical Approach," Neuropsychopharmacology, (2017), 42:360-378.

Niculescu et al., "Effects of p21Cip1/Waf1 at Both the G1/S and the G2/M Cell Cycle Transitions: pRb Is a Critical Determinant in Blocking DNA Replication and in Preventing Endoreduplication," Molecular and cellular biology, (1998), 18(1):629-643.

Niculescu et al., Psychiatric blood biomarkers: avoiding jumping to premature negative or positive conclusions, Mol. Psychiatry, (2015), 20(3):286-288.

Niculescu et al., "Understanding and predicting suicidality using a combined genomic and clinical risk assessment approach," Molecular Psychiatry, (2015), 20:1266-1285.

Niculescu et al., Precision medicine for suicidality: from universality to subtypes and personalization, Molecular Psychiatry, (2017), 22:1250-1273.

Oquendo et al., "Toward a Biosignature for Suicide," Am. J. Psychiatry, (2014) 171(12):1259-1277.

Owens, Predictors of suicidal behavior found in blood, Nature, doi:10.1038/nature.2013.13570; Aug. 20, 2013. Available at http://www.nature.com/news/predictors-of-suicidal-behaviour-found-in-blood-1.13570.

Pandey, G. N., Y. Dwivedi, et al. (2003). "Altered expression and phosphorylation of myristoylated alanine-rich Ckinase substrate (MARCKS) in postmortem brain of suicide victims with or without depression." J Psychiatr Res 37(5):421-432.

Stopkova, et al. "Identification of PIK3C3 Promoter Variant Associated with Bipolar Disorder and Schizophrenia. Biological Psychiatry", May 15, 2004; vol. 55, No. 10; pp. 981-988.

Supplementary European search report dated Jan. 21, 2019 for EP Application No. 16808423.

Tsai et al., "Bcl-2 associated with positive symptoms of schizophrenic patients in an acute phase", Psychiatry Research vol. 210, Issue 3, Dec. 30, 2013, pp. 735-738.

Underwood, A blood test for suicide?, https://www.sciencemag.org/news/2013/08/blood-test-suicide.

Asellus et al., J. Affective Disorders, 2016, 190:132-142.

Hwang et al., Dementia and geriatric cognitive disorders, 2006, 22(41:334-8).

Non-Final Office Action issued by the United States Patent and Trademark Office, dated Mar. 18, 2021, for U.S. Appl. No. 16/677,414; 14 pages.

\* cited by examiner

SUICIDAL IDEATION (SI)
FROM HAMILTON RATING SCALE FOR DEPRESSION (HAMD17)
No SI - SCORE OF 0; High SI - SCORE OF 2 OR ABOVE

SUICIDE

0 = ABSENT
1 = FEELS LIFE IS NOT WORTH LIVING
2 = WISHES HE WERE DEAD OR ANY THOUGHTS OF POSSIBLE DEATH TO SELF
3 = SUICIDAL IDEAS OR GESTURE
4 = ATTEMPTS AT SUICIDE (ANY SERIOUS ATTEMPT RATES 4)

FIG. 1B

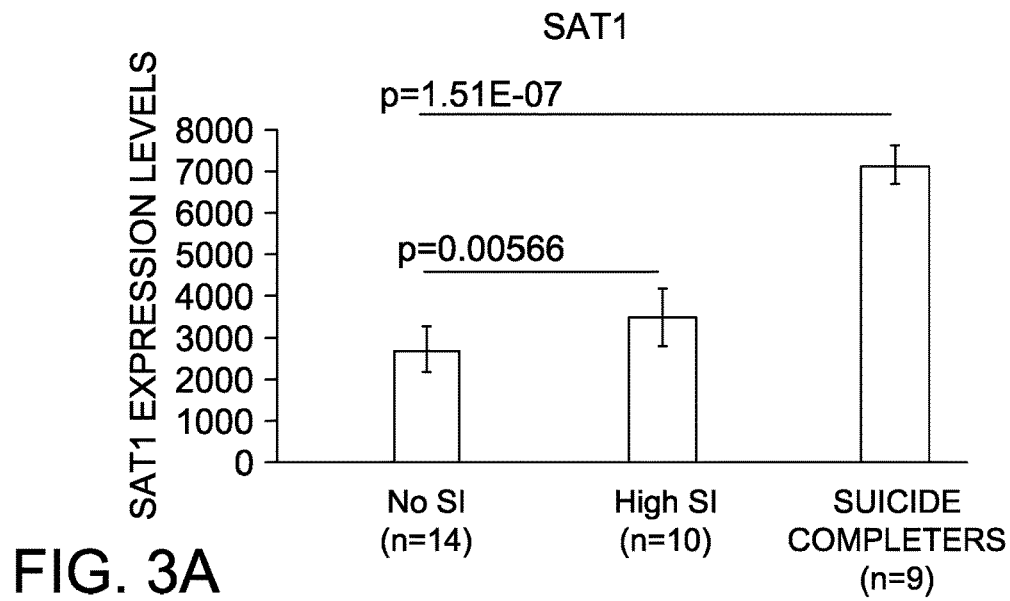
FIG. 3A
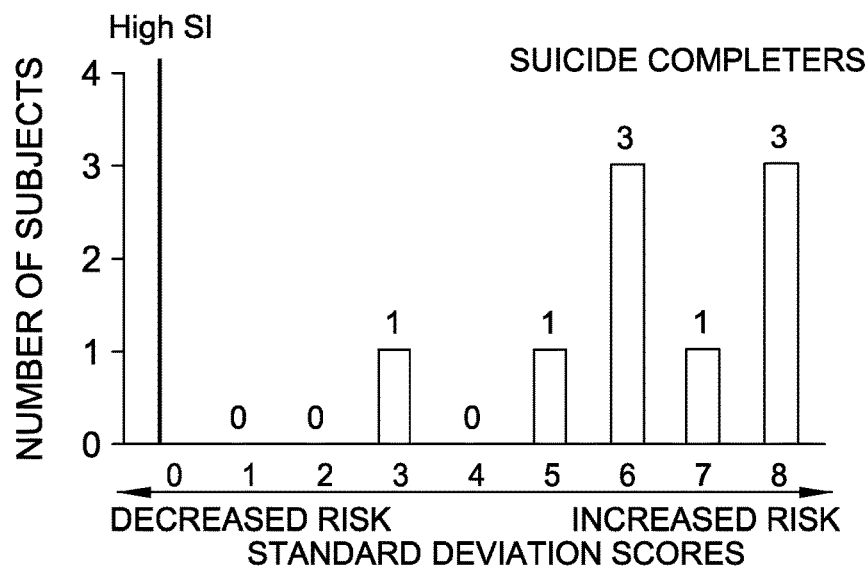
FIG. 3B
| DISCOVERY COHORT | SAT1 STANDARD DEVIATION SCORES | | | | | | | | |
|---|---|---|---|---|---|---|---|---|---|
| | 0 | 1 | 2 | 3 | 4 | 5 | 6 | 7 | 8 |
| DISCOVERY COHORT VALUES DETERMINE RISK CUTOFFS | 2642.97-3413.37 | 3413.37-4084.34 | 4084.34-4755.31 | 4755.31-5426.28 | 5426.28-6097.25 | 6768.22-7439.19 | 7439.19-8110.16 | 8110.16-8781.12 | 8781.12-9452.1 |
| High SI mean = 3413.37 High SI Std. D = 670.97 | | | | INBR009 | | INBR011 | INBR013 INBR017 INBR018 | INBR016 | INBR012 INBR014 INBR015 |
FIG. 3C

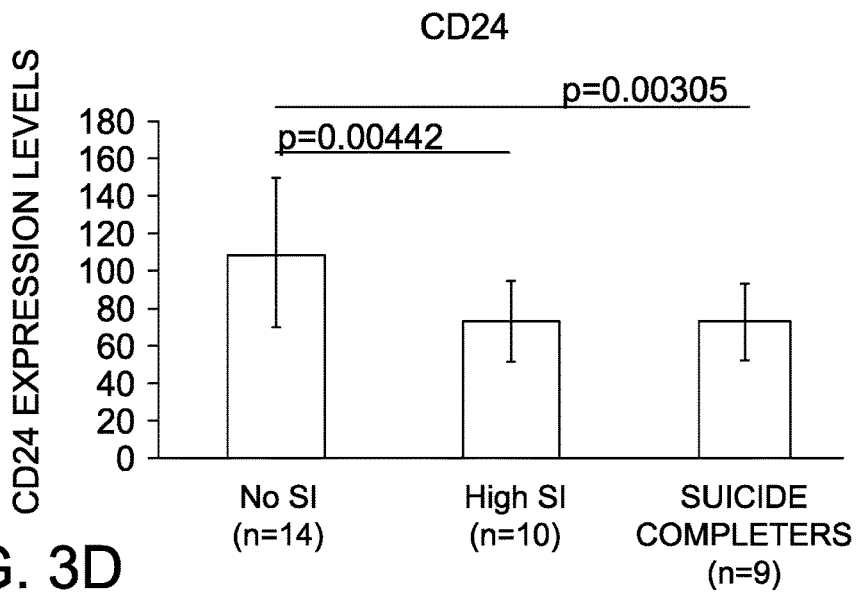
FIG. 3D
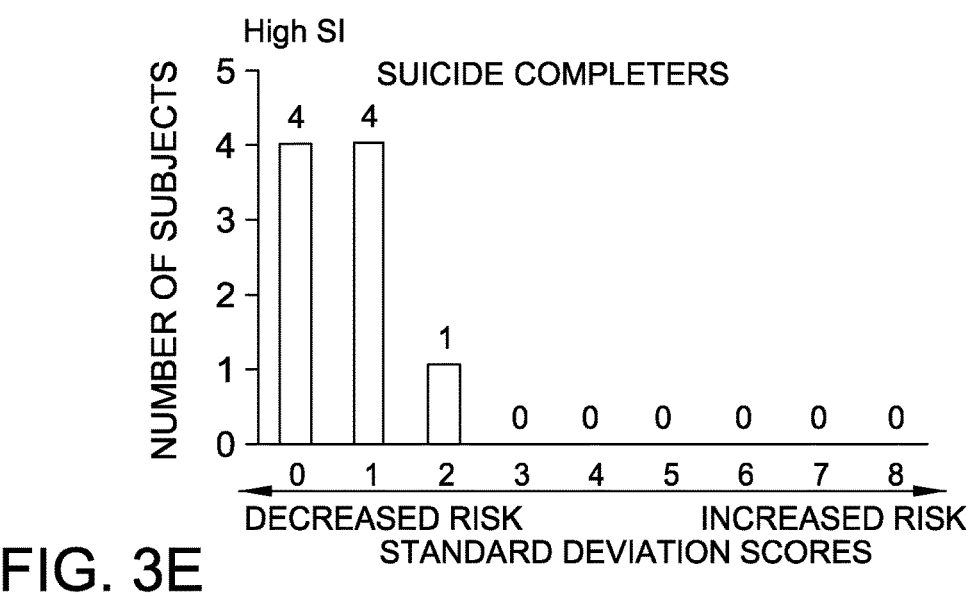
FIG. 3E
| DISCOVERY COHORT | CD24 STANDARD DEVIATION SCORES | | | | | | | | |
|---|---|---|---|---|---|---|---|---|---|
| | 0 | 1 | 2 | 3 | 4 | 5 | 6 | 7 | 8 |
| DISCOVERY COHORT VALUES DETERMINE RISK CUTOFFS | 108.63-73.01 | 73.01-51.53 | 51.53-30.01 | 30.01-8.58 | 8.58-0 | 0 | 0 | 0 | 0 |
| High SI mean = 73.01 High SI Std. D = 21.48 | INBR011 INBR014 INBR016 INBR018 | INBR009 INBR012 INBR017 INBR015 | INBR013 | | | | | | |
FIG. 3F

| CFG Score | Gene | Direction of Change | P-Value (One-Way ANOVA) |
|---|---|---|---|
| 8 | SAT1 | I | 2.91E-13 |
| 4 | UBA6 | I | 8.94E-05 |
| 6 | MARCKS | I | 0.000187221 |
| 6 | PTEN | I | 0.000298958 |
| 4 | MT-ND6 | I | 0.000391061 |
| 4 | MAP3K3 | I | 0.000777774 |
| 6 | LHFP | I | 0.001535921 |
| 4 | LOC727820 | I | 0.003706529 |
| 8 | CD24 | D | 0.006082658 |
| 6 | RECK | I | 0.009035235 |
| 8 | FOXN3 | I | 0.010040264 |
| 4 | SCARF1 | I | 0.014880001 |
| 4 | RICTOR | I | 0.040726456 |

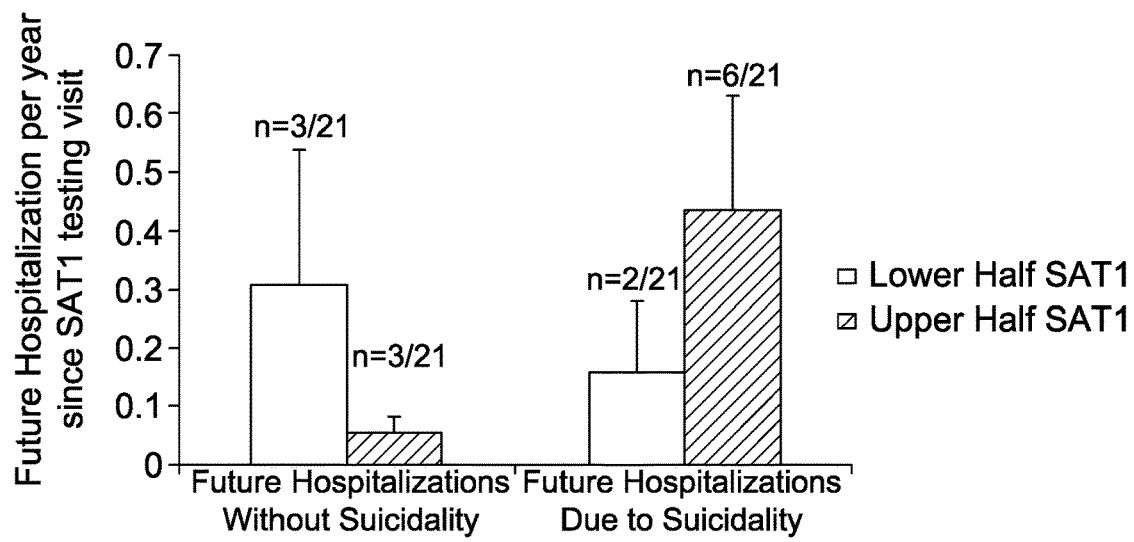
FIG. 5A
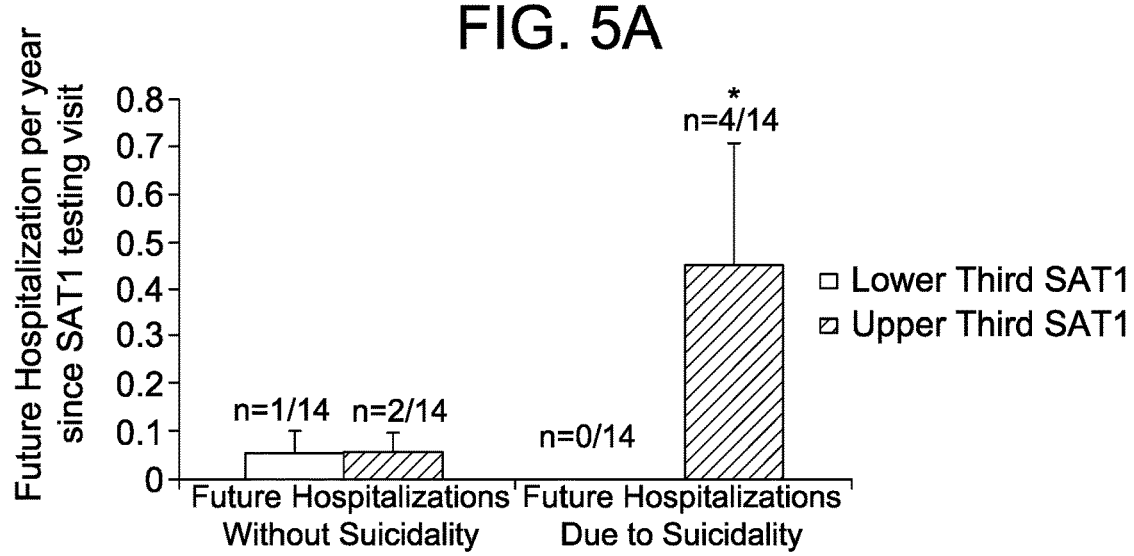
FIG. 5B
|  | Hospitalizations Without Suicidality t-test | Hospitalizations Due to Suicidality t-test |
|---|---|---|
| Upper Half SAT1 vs. Lower Half SAT1 | 0.14028 | 0.1195 |
| Upper Third SAT1 vs. Lower Third SAT1 | 0.4827 | 0.0484 |
FIG. 5C

| | Hospitalizations Without Suicidality t-test | Hospitalizations Due to Suicidality t-test |
|---|---|---|
| Bipolar Upper Third SAT1 vs. Lower Third SAT1 | 0.1108 | 0.03626 |

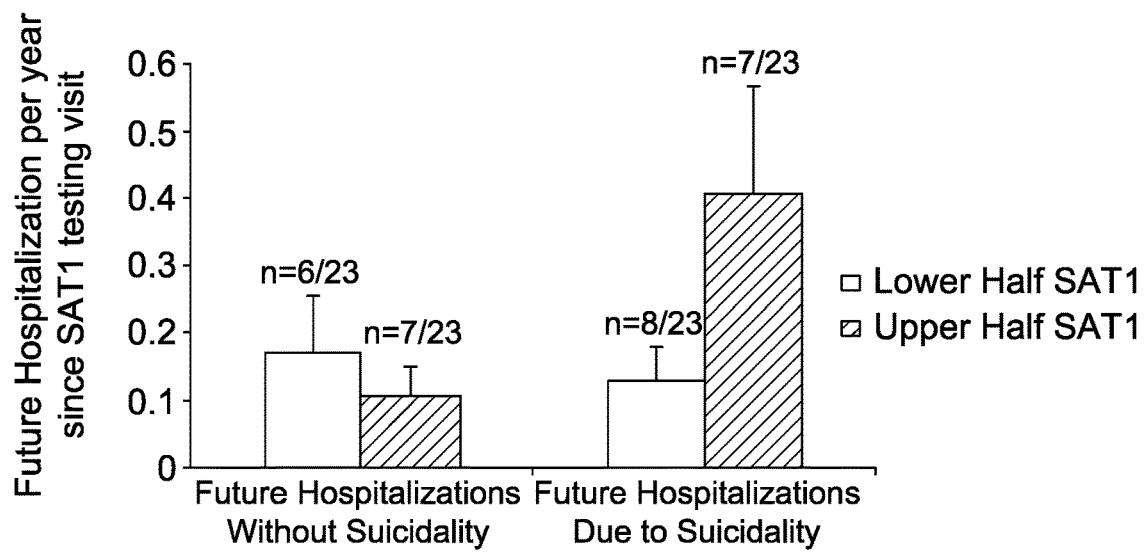
FIG. 6A
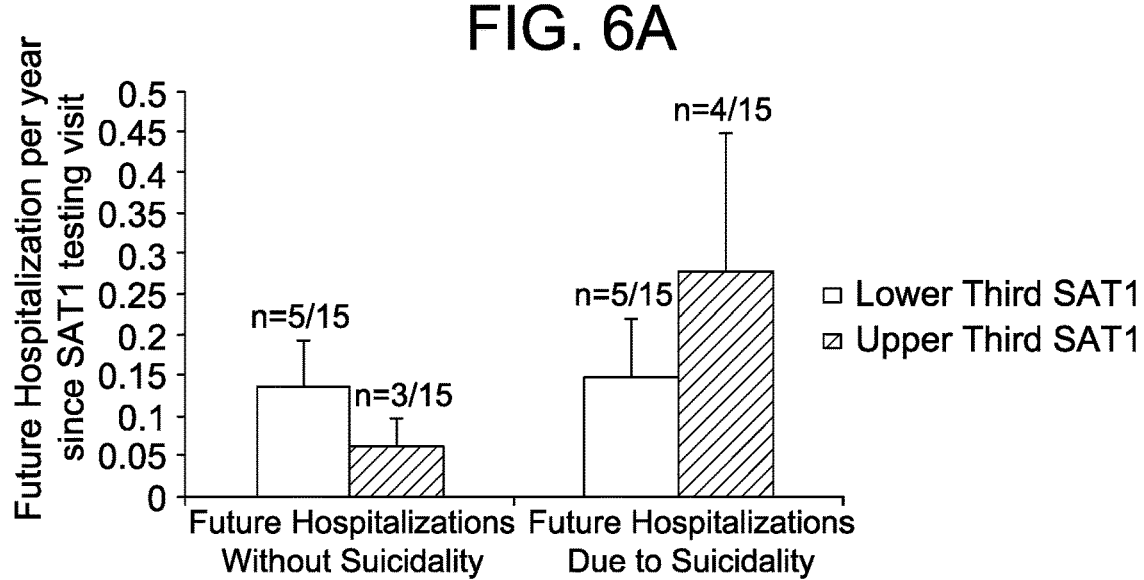
FIG. 6B
|  | Hospitalizations Without Suicidality t-test | Hospitalizations Due to Suicidality t-test |
|---|---|---|
| Upper Half SAT1 vs. Lower Half SAT1 | 0.2346 | 0.0519 |
| Upper Third SAT1 vs. Lower Third SAT1 | 0.1251 | 0.2461 |
FIG. 6C

| | Hospitalizations Without Suicidality t-test | Hospitalizations Due to Suicidality t-test |
|---|---|---|
| Psychosis Upper Half SAT1 vs. Lower Half SAT1 | 0.4564 | 0.0274 |

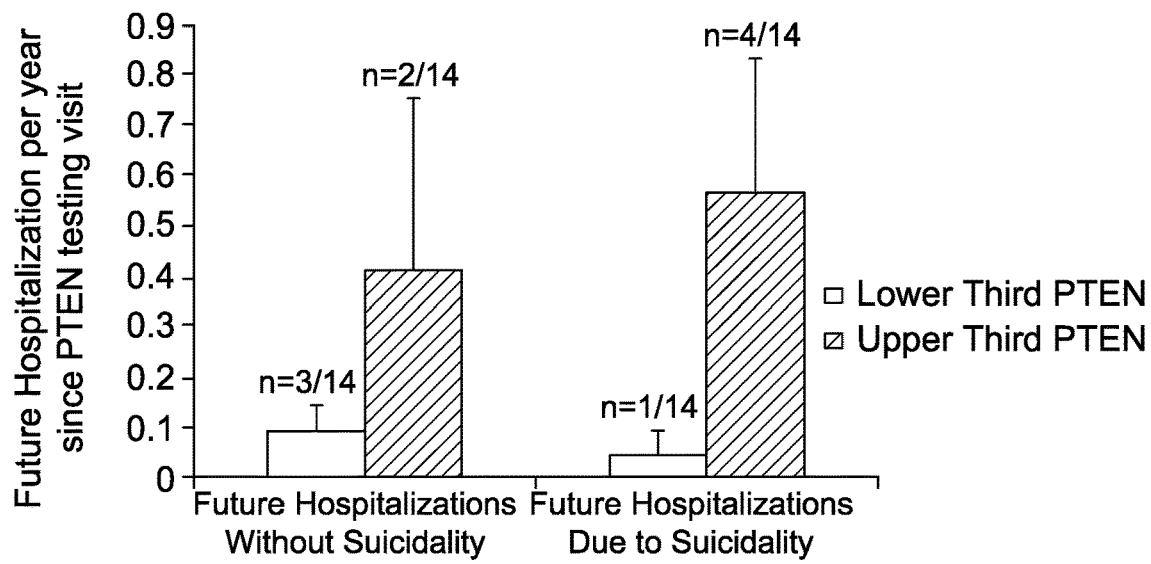
FIG. 7A
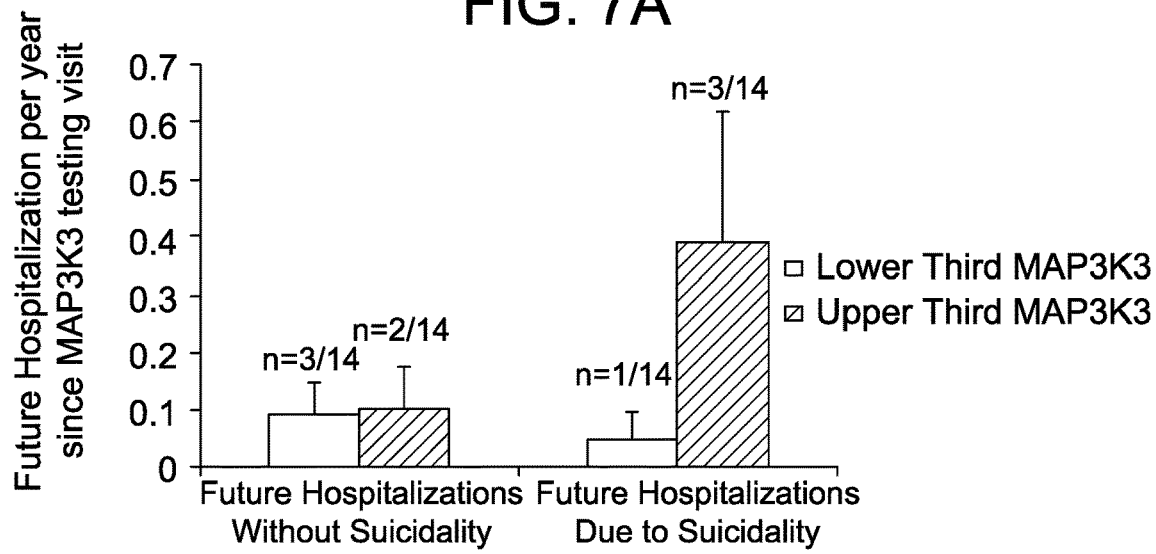
FIG. 7B
|  | Hospitalizations Without Suicidality t-test | Hospitalizations Due to Suicidality t-test |
| --- | --- | --- |
| Upper Third PTEN vs. Lower Third PTEN | 0.1856 | 0.0324 |
| Upper Third MAP3K3 vs. Lower Third MAP3K3 | 0.4570 | 0.0724 |
FIG. 7C

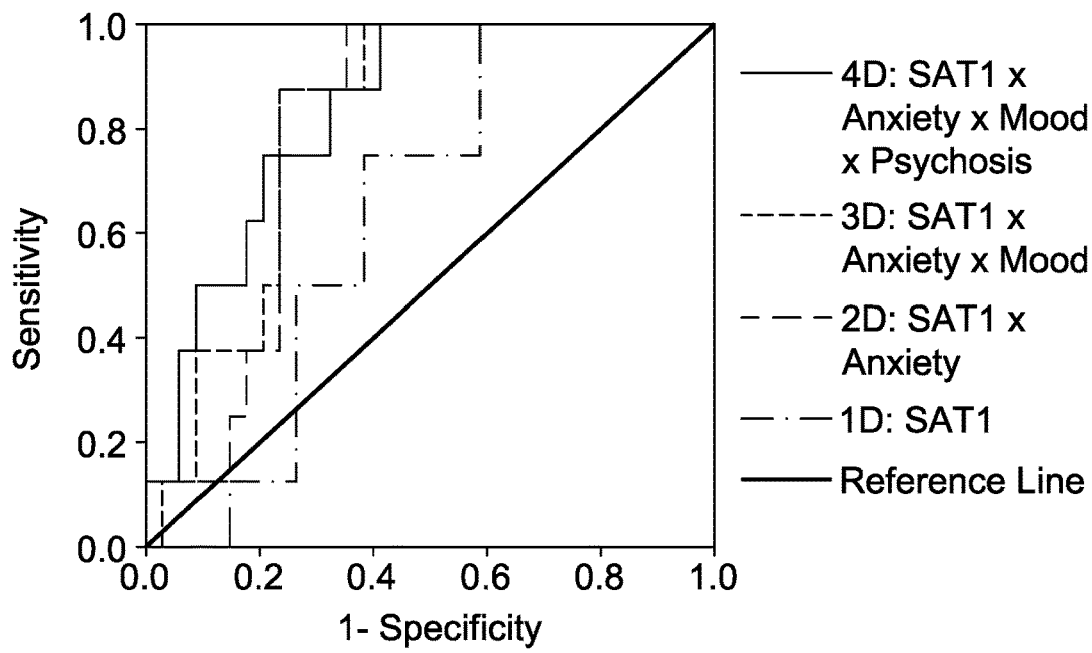
FIG. 8A
| D | Test Result Variable(s) | Area Under the Curve | Std. Error | Significance | 95% Confidence Interval | |
|---|---|---|---|---|---|---|
| | | | | | Lower Bound | Upper Bound |
| 1D | SAT1 | .640 | .086 | .224 | .471 | .808 |
| 2D | SAT1 x Anxiety | .798 | .068 | .009 | .665 | .931 |
| 3D | SAT1 x Anxiety x Mood | .813 | .066 | .006 | .683 | .942 |
| 4D | SAT1 x Anxiety x Mood x Psychosis | .835 | .066 | .004 | .706 | .964 |
FIG. 8B
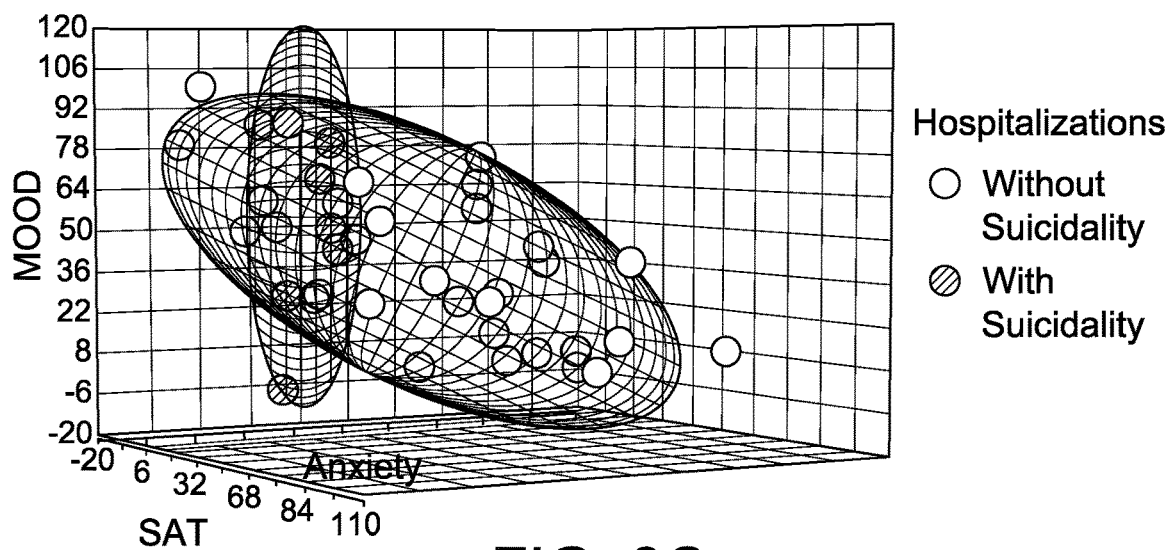
FIG. 8C

| D | Test Result Variable(s) | Area Under the Curve | Std. Error | Significance | 95% Confidence Interval ||
|---|---|---|---|---|---|---|
| | | | | | Lower Bound | Upper Bound |
| 1D | BioM6 | .732 | .079 | .044 | .578 | .886 |
| 2D | BioM6 x Anxiety | .864 | .056 | .002 | .754 | .974 |

1) Anxiety

How anxious are you right now? Compare to the worst, and to the most anxious, you ever remember feeling in your life, and to the best, least anxious you ever remember feeling.

Least Anxious                                Most Anxious

2) Mood

How good is your mood right now? Compare to the worst, most depressed you ever remember feeling in your life, and to the best you ever remember feeling.

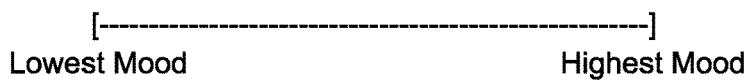

Lowest Mood                              Highest Mood

3) Psychosis: averaging the scores for Hallucinations and Delusions, two key psychotic symptoms, from the Positive and Negative Symptoms Scale (PANSS)

(A) Hallucinatory Behavior: Verbal report or behavior indicating perceptions which are not generated by external stimuli. These may occur in the auditory, visual, olfactory or somatic realms. Basis for rating: Verbal report and physical manifestations during the course of interview.

| Hallucinations Score | State | Definition |
|---|---|---|
| 1 | Absent | Definition does not apply |
| 2 | Minimal | Questionable pathology; may be at the upper extreme of normal limits |
| 3 | Mild | One or two clearly formed but intelligent hallucinations, or else a number of vague abnormal perceptions which do not result in distortions of thinking or behavior. |
| 4 | Moderate | Hallucinations occur frequently but not continuously, and the patient's thinking and behavior are affected only to a minor extent. |
| 5 | Moderate Severe | Hallucinations are frequent, may include more than one sensory modality, and tend to distort thinking and/or disrupt behavior. Patient may have delusional interpretation of these experiences and respond to them emotionally and, on occasion, verbally as well. |
| 6 | Severe | Hallucinations are present almost continuously, causing major disruption of thinking and behavior. Patient treats these as real perceptions, and functioning is impeded by frequent emotional and verbal responses to them. |
| 7 | Extreme | Patient is almost totally preoccupied with hallucinations which virtually dominate thinking and behavior. Hallucinations are provided a rigid delusional interpretation and provoke verbal and behavioral responses, including obedience to command hallucinations. |

B) Delusions: beliefs which are unfounded, unrealistic, and idiosynchratic. Basis for rating: thought content expressed in the interview.

| Delusions Score | State | Definition |
|---|---|---|
| 1 | Absent | Definition does not apply |
| 2 | Minimal | Questionable pathology; may be at the upper extreme of normal limits |
| 3 | Mild | Presence of one or two delusions which are vague, uncrystallized and not tenaciously held. Delusions do not interfere with thinking, social relations or behavior. |
| 4 | Moderate | Presence of either a kaleidoscopic array of poorly formed, unstable delusions or of a few well formed delusions that occasionally interfere with thinking, social relations or behavior. |
| 5 | Moderate Severe | Presence of numerous, well-formed delusions that are tenaciously held and occasionally interfere with thinking, social relations or behavior. |
| 6 | Severe | Presence of a stable set of delusions which are crystallized, possibly systemitized, tenaciously held and clearly interfere with thinking, social relations and behavior. |
| 7 | Extreme | Presence of a stable set of delusions which are highly systemitized or very numerous, and which dominate major facets of the patient's life. This frequently results in inappropriate and irresponsible action, which may even jeopardize the safety of the patient or others. |

FIG. 10

BLOOD BIOMARKERS FOR SUICIDALITY

CROSS-REFERENCE TO RELATED APPLICATIONS

This application is a continuation application of U.S. application Ser. No. 14/194,024 filed on Feb. 28, 2014, which claims priority to U.S. Provisional Patent Application No. 61/770,696 filed on Feb. 28, 2013, both of which are hereby incorporated by reference in their entireties.

STATEMENT OF GOVERNMENT SUPPORT

This invention was made with government support under OD007363 awarded by the National Institutes of Health. The Government has certain rights in the invention.

BACKGROUND OF THE DISCLOSURE

The present disclosure relates generally to blood biomarkers and their use for predicting mental state, and in particular, for predicting a subjects' risk of suicide (also referred to herein as "suicidality"). More particularly, the present disclosure relates to gene expression biomarkers, and to methods of screening for biomarkers, for identifying subjects who are at risk of committing suicide and methods for monitoring response to potential treatments by analyzing biomarkers.

Suicides are a leading cause of death in psychiatric patients, and in society at large. Particularly, suicide accounts for one million deaths worldwide each year. There are currently no objective tools to asses and track changes in suicidal risk without asking the subjects directly. Such tools, however, could prove substantially advantageous as the subjects at risk often choose not to share their suicidal ideation or intent with others, for fear of stigma, hospitalization, or that, in fact, their plans will be thwarted.

Conventionally, a convergence of methods assessing the subject's internal subjective feelings and thoughts, along with external, more objective, ratings of actions and behaviors, are used de facto in clinical practice, albeit not in a formalized and systematic way. Accordingly, there exists a need to develop more quantitative and objective ways for predicting and tracking suicidal states. More particularly, it would be advantageous if objective screening methods could be developed for determining expression levels of biomarkers to allow for determining suicidal risk and other psychotic depressed mood states, as well as monitoring a subject's response to treatments for lessening suicidal risk.

SUMMARY OF THE DISCLOSURE

The present disclosure relates generally to predicting and tracking suicidality. Particularly, the present disclosure is directed to screening expression levels of biomarkers for predicting and tracking suicidality, and other psychotic depressed mood states, as well as for monitoring response to a treatment for suicidal risk. In one embodiment, the screening methods are useful in determining the suicidal risk of antidepressant treatment in a subject, which has been shown to be rare, but very serious in certain situations.

Biomarkers useful for identifying subjects at risk for suicide, as well as useful for monitoring the risk of suicide following treatment have been discovered. Accordingly, the present disclosure is directed to methods of identifying a subject at risk for suicide. The present disclosure is further directed to methods for monitoring response of a subject at risk for suicide to a treatment for suicide risk.

By monitoring and tracking changes in suicide state, the present disclosure allows for detection of an increased suicide risk prior to any suicide attempt by a subject, and further allows subjects at risk of suicide and other psychotic depressed mood states to be monitored and treated effectively. Accordingly, in another embodiment, the present disclosure relates to predicting future hospitalization for subjects being at risk for suicide and other psychotic depressed mood states such to provide sufficient monitoring and treatment to the subjects.

In one aspect, the present disclosure is directed to a method for identifying a subject at risk for suicide. The method includes obtaining a reference expression level of a blood biomarker; and determining an expression level of the blood biomarker in a sample obtained from the subject, wherein a change in the expression level of the blood biomarker in the sample obtained from the subject as compared to the reference expression level indicates a risk for suicide.

In another aspect, the present disclosure is directed to a method for monitoring response of a subject to a treatment for suicidal risk. The method includes obtaining an expression level of a biomarker from the subject; administering a treatment for suicidal risk to the subject; and determining an expression level of the biomarker in a sample obtained from the subject after the treatment is administered, wherein a change in the expression level of the biomarker in the sample obtained from the subject after the treatment is administered as compared to the expression level before administration indicates a response to the treatment.

In another aspect, the present disclosure is directed to a method for determining suicidal risk of an antidepressant, the method comprising: obtaining an expression level of a biomarker from a subject; administering an antidepressant to the subject; and determining an expression level of the biomarker in a sample obtained from the subject after the antidepressant is administered, wherein a change in the expression level of the biomarker in the sample obtained from the subject after the antidepressant is administered as compared to the expression level of the biomarker before the antidepressant is administered indicates a suicidal risk.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 1B depicts the HAMD17 Suicidal Ideation scores as discussed in Example 1.

FIGS. 3A-I depict the validation of biomarkers in the Validation Cohort (i.e., suicide completers) as discussed in Example 1.

FIGS. 5A-E depict SAT1 expression levels versus subsequent hospitalizations due to suicidality as analyzed in Example 2.

FIGS. 6A-E depict SAT1 expression levels versus prediction of future hospitalizations due to suicidality as analyzed in Example 2.

FIGS. 7A-C depict expression levels of PTEN and MAP3K3 versus prediction of future hospitalizations due to suicidality as analyzed in Example 2.

FIGS. 8A-8C depict multi-dimensional prediction of future psychiatric hospitalizations due to suicidality as analyzed in Example 2. Data in each dimension was normalized to a 0-100 scale (with the mood VAS scale inverted, as the assumption was made that depressed mood states would more closely correlate with suicidality). The angle between dimensions was assumed to be 90 degrees, and a simple Pythagorean distance from origin score was calculated. The distribution of this score in the test cohort was used to generate an ROC curve for hospitalizations due to suicidality. FIG. 8A). ROC curve. FIG. 8B). Detailed results. FIG. 8C). 3 D visualization.

FIG. 9A). ROC curve. FIG. 9B). Detailed results.

FIG. 10 depicts the clinical measures used in the multimodal approach in FIGS. 8A-8C.

Figure 1A:
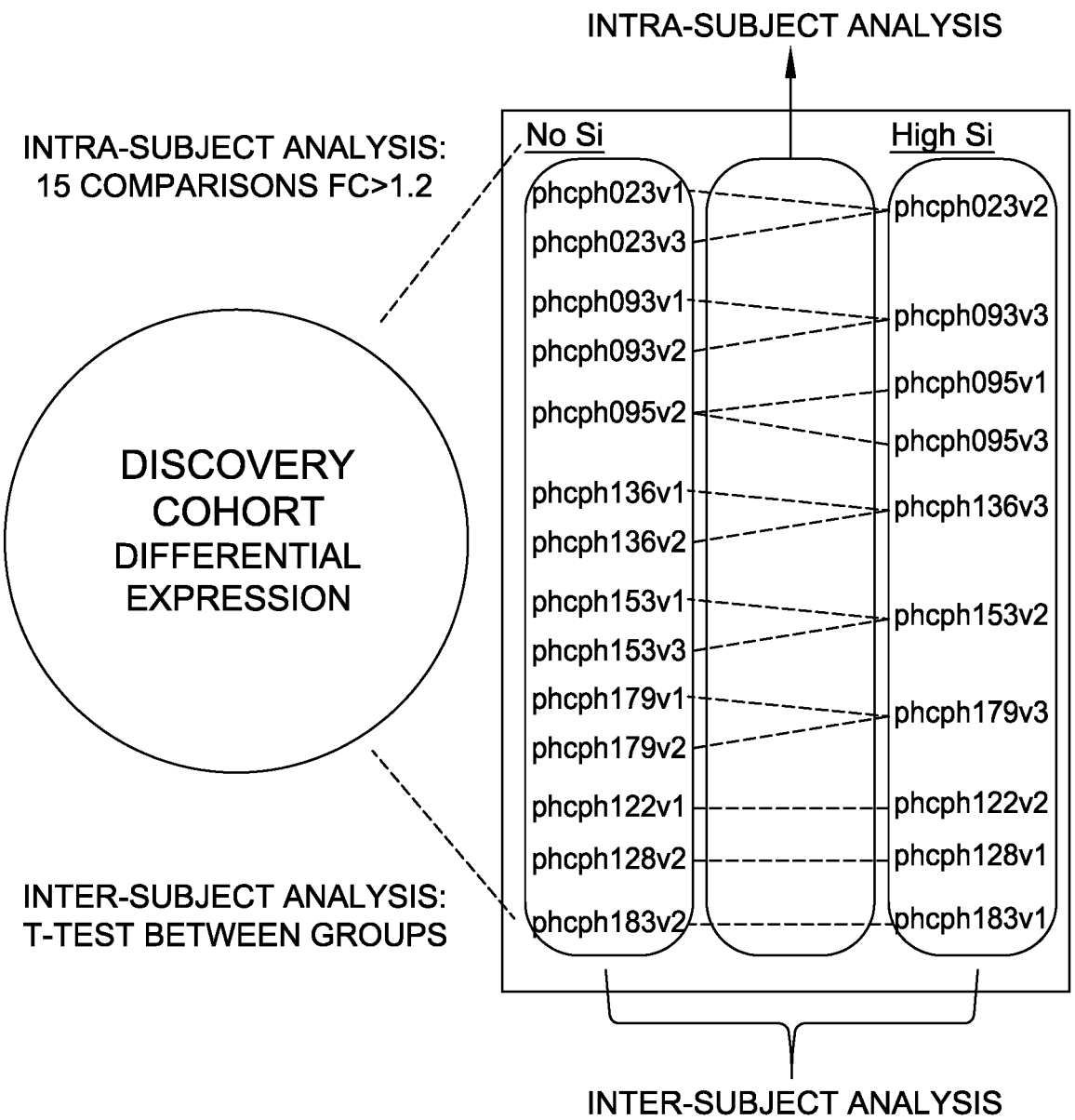
FIG. 1A depicts the Discovery Cohort intra-subject and inter-subject analyses as discussed in Example 1.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein may be used in the practice or testing of the present disclosure, the preferred materials and methods are described below.

In accordance with the present disclosure, biomarkers useful for objectively identifying subjects at risk for suicide, as well as for monitoring the risk of suicide following treatment and determining the risk of suicide following administration of antidepressants have been discovered. In one aspect, the present disclosure is directed to a method for identifying a subject at risk for suicide. The method includes obtaining a reference expression level of a blood biomarker; and determining an expression level of the blood biomarker in a sample obtained from the subject. A change in the expression level of the blood biomarker in the sample obtained from the subject as compared to the reference expression level indicates a risk for suicide. In some embodiments, the methods further include obtaining clinical risk factor information and clinical scale data such as for anxiety, mood and/or psychosis from the subject in addition to obtaining blood biomarker expression level in a sample obtained from the subject. This combined clinical data and blood biomarker expression level can further improve predictability of the risk of suicide as shown in FIGS. 8A-8C and 9A-9B.

As used herein, "a subject at risk for suicide" refers to a subject diagnosed by one skilled in the art such as, for example, a clinician, using established protocols and methods for diagnosing suicidality. Such methods can include, for example, rigorous clinical interview using clinical standards for assessing and diagnosing whether a subject is at risk for suicide. Suicidality diagnosis can be established using, for example, questionnaires to identify suicidal ideation. Diagnosis can include diagnostic assessment using psychiatric rating scales including, for example, the Hamilton Rating Scale for Depression (HAMD-17), which includes a suicidal ideation rating item, Beck Scale for suicide ideation, Columbia Suicide Severity Rating Scale, The Kessler Psychological Distress Scale, and combinations thereof.

Particularly suitable subjects are humans. Suitable subjects can also be experimental animals such as, for example, monkeys and rodents, that display a behavioral phenotype associated with suicide, for example, a mood disorder or psychosis.

As used herein, "a reference expression level of a biomarker" refers to the expression level of a biomarker established for a subject with no suicidal ideation, expression level of a biomarker in a normal/healthy subject with no suicidal ideation as determined by one skilled in the art using established methods as described herein, and/or a known expression level of a biomarker obtained from literature. As known by those skilled in the art, "suicidal ideation" refers to thoughts, feelings, intent, external actions and behaviors about completing suicide. Suicidal ideation can vary from fleeting thoughts to unsuccessful attempts.

As used herein, "expression level of a biomarker" refers to the process by which a gene product is synthesized from a gene encoding the biomarker as known by those skilled in the art. The gene product can be, for example, RNA (ribonucleic acid) and protein. Expression level can be quantitatively measured by methods known by those skilled in the art such as, for example, northern blotting, amplification, polymerase chain reaction, microarray analysis, tag-based technologies (e.g., serial analysis of gene expression and next generation sequencing such as whole transcriptome shotgun sequencing or RNA-Seq), Western blotting, and combinations thereof.

Suitable biomarkers found to have a change in expression level include, for example, spermidine/spermine N1-acetyltransferase 1 (SAT1); forkhead box N3 (FOXN3); guanylate binding protein 1 (GBP1); phosphoinositide-3-kinase regulatory subunit 5 (PIK3R5); apolipoprotein L2 (APOL2); ATPase H+ transporting lysosomal 9 kDa, V0 subunit e1 (ATP6V0E1); GRINL1A complex locus (GCOM1); interleukin 1 beta (IL1B); lipoma HMGIC fusion partner (LHFP); lipase A (LIPA); myristoylated alanine-rich protein kinase C substrate (MARCKS); 6-phosphogluconolactonase (PGLS); phosphatase and tensin homolog (PTEN); reversion-inducing-cysteine-rich protein with kazal motifs (RECK); tumor necrosis factor (ligand) superfamily member 10 (TNFSF10); ATP-binding cassette, subfamily A (ABC1) member 1 (ABCA1); Rho guanine nucleotide exchange factor (GEF) 40 (ARHGEF4; FLJ10357); cancer susceptibility candidate 1 (CASC1); dehydrogenase/reductase (SDR family) member 9 (DHRS9); disrupted in schizophrenia 1 (DISC1); eukaryotic translation initiation factor 2-alpha kinase 2 (EIF2AK2); uncharacterized LOC727820 (LOC727820); mitogen-activated protein kinase kinase kinase 3 (MAP3K3); mitochondrially encoded NADH dehydrogenase 6 (MT-ND6; ND6); RNA binding motif protein 47 (RBM47); RPTOR independent companion of MTOR complex 2 (RICTOR); sterile alpha motif domain containing 9-like (SAMD9L); scavenger receptor class F member 1 (SCARF1); solute carrier family 36 (proton/amino acid symporter) member 1 (SLC36A1); signal transducer and activator of transcription 1, 91 kDa (STAT1); cytochrome c oxidase subunit Vb (COX5B); SWI/SNF related matrix associated actin dependent regulator of chromatin subfamily a member 1 (SMARCA1); ubiquitin-like modifier activating enzyme 6 (UBA6); zinc finger CCCH-type antiviral 1 (ZC3HAV1), CD24, ATP13A2, EPHX1, HTRA1, SPTBN1, MBNL2, OR2J3, RHEB, DBP, and combination thereof. Particularly suitable biomarkers include SAT1, MARCKS, PTEN, MAP3K3, and combinations thereof.

As used herein, a "change" in the expression level of the biomarker refers to an increase or a decrease of by about 1.2-fold or greater in the expression level of the biomarker as determined in a sample obtained from the subject as compared to the reference expression level of the biomarker. In one embodiment, the change in expression level is an increase or decrease by about 1.2 fold.

In one embodiment, the expression level of the blood biomarker in the sample obtained from the subject is increased as compared to the reference expression level of the biomarker. It has been found that an increase in the expression level of particular blood biomarkers in the sample obtained from the subject as compared to the reference expression level of the biomarker indicates a risk for suicide. Suitable biomarkers that indicate a risk for suicide when the expression level increases can be, for example, spermidine/spermine N1-acetyltransferase 1 (SAT1); forkhead box N3 (FOXN3); guanylate binding protein 1 (GBP1); phosphoinositide-3-kinase regulatory subunit 5 (PIK3R5); apolipoprotein L2 (APOL2); ATPase H+ transporting lysosomal 9 kDa, V0 subunit e1 (ATP6V0E1); GRINL1A complex locus (GCOM1); interleukin 1 beta (IL1B); lipoma HMGIC fusion partner (LHFP); lipase A (LIPA); myristoylated alanine-rich protein kinase C substrate (MARCKS); 6-phosphogluconolactonase (PGLS); phosphatase and tensin homolog (PTEN); reversion-inducing-cysteine-rich protein with kazal motifs (RECK); tumor necrosis factor (ligand) superfamily member 10 (TNFSF10); ATP-binding cassette, subfamily A (ABC1) member 1 (ABCA1); Rho guanine nucleotide exchange factor (GEF) 40 (ARHGEF4; FLJ10357); cancer susceptibility candidate 1 (CASC1); dehydrogenase/reductase (SDR family) member 9 (DHRS9); disrupted in schizophrenia 1 (DISC1); eukaryotic translation initiation factor 2-alpha kinase 2 (EIF2AK2); uncharacterized LOC727820 (LOC727820); mitogen-activated protein kinase kinase kinase 3 (MAP3K3); mitochondrially encoded NADH dehydrogenase 6 (MT-ND6; ND6); RNA binding motif protein 47 (RBM47); RPTOR independent companion of MTOR complex 2 (RICTOR); sterile alpha motif domain containing 9-like (SAMD9L); scavenger receptor class F member 1 (SCARF1); solute carrier family 36 (proton/amino acid symporter) member 1 (SLC36A1); signal transducer and activator of transcription 1, 91 kDa (STAT1); cytochrome c oxidase subunit Vb (COX5B); SWI/SNF related matrix associated actin dependent regulator of chromatin subfamily a member 1 (SMARCA1); ubiquitin-like modifier activating enzyme 6 (UBA6); zinc finger CCCH-type antiviral 1 (ZC3HAV1); tyrosine kinase, non-receptor 2 (TNK2), and combinations thereof. See, Table 5 for a list of biomarkers identified as showing an increase in expression level.

In another embodiment, the expression level of the blood biomarker in the sample obtained from the subject is decreased as compared to the reference expression level of the biomarker. Suitable biomarkers that indicate a risk for suicide when the expression level decreases as compared to the reference expression level have been found to include, for example, cluster 4 antigen (CD24; CD24 molecule); ATPase type 13A2 (ATP13A2); epoxide hydrolase 1, microsomal (xenobiotic) (EPHX1); HtrA serine peptidase 1 (HTRA1); leptin receptor (LEPR); spectrin beta non-erythrocytic 1 (SPTBN1); muscleblind-like 2 (MBNL2); olfactory receptor family 2 subfamily J member 3 (OR2J3); Ras homolog enriched in brain (RHEB); glutamate receptor, ionotropic, N-methyl D-aspartate-associated protein 1 (GRINA); D-box binding protein, promyelocytic leukemia (PML), potassium inwardly-rectifying channel, subfamily J, member 2 (KCNJ2), topoisomerase (DNA) 1 (TOP1) and combinations thereof. See, Table 5 for a list of biomarkers identified as showing a decrease in expression level.

In another embodiment, the method includes determining the expression level of a blood biomarker in the sample obtained from the subject that is increased as compared to the reference expression level of the biomarker and determining the expression level of the blood biomarker in the sample obtained from the subject that is decreased as compared to the reference expression level of the biomarker. For example, spermidine/spermine N1-acetyltransferase 1 (SAT1); forkhead box N3 (FOXN3); guanylate binding protein 1 (GBP1); phosphoinositide-3-kinase regulatory subunit 5 (PIK3R5); apolipoprotein L2 (APOL2); ATPase H+ transporting lysosomal 9 kDa, V0 subunit e1 (ATP6V0E1); GRINL1A complex locus (GCOM1); interleukin 1 beta (IL1B); lipoma HMGIC fusion partner (LHFP); lipase A (LIPA); myristoylated alanine-rich protein kinase C substrate (MARCKS); 6-phosphogluconolactonase (PGLS); phosphatase and tensin homolog (PTEN); reversion-inducing-cysteine-rich protein with kazal motifs (RECK); tumor necrosis factor (ligand) superfamily member 10 (TNFSF10); ATP-binding cassette, subfamily A (ABC1) member 1 (ABCA1); Rho guanine nucleotide exchange factor (GEF) 40 (ARHGEF4; FLJ10357); cancer susceptibility candidate 1 (CASC1); dehydrogenase/reductase (SDR family) member 9 (DHRS9); disrupted in schizophrenia 1 (DISC1); eukaryotic translation initiation factor 2-alpha kinase 2 (EIF2AK2); uncharacterized LOC727820 (LOC727820); mitogen-activated protein kinase kinase kinase 3 (MAP3K3); mitochondrially encoded NADH dehydrogenase 6 (MT-ND6; ND6); RNA binding motif protein 47 (RBM47); RPTOR independent companion of MTOR complex 2 (RICTOR); sterile alpha motif domain containing 9-like (SAMD9L); scavenger receptor class F member 1 (SCARF1); solute carrier family 36 (proton/amino acid symporter) member 1 (SLC36A1); signal transducer and activator of transcription 1, 91 kDa (STAT1); cytochrome c oxidase subunit Vb (COX5B); SWI/SNF related matrix associated actin dependent regulator of chromatin subfamily a member 1 (SMARCA1); ubiquitin-like modifier activating enzyme 6 (UBA6); zinc finger CCCH-type antiviral 1 (ZC3HAV1); tyrosine kinase, non-receptor 2 (TNK2), and combinations thereof in the blood sample of the subject can be increased as compared to the reference expression level, and cluster 4 antigen (CD24; CD24 molecule); ATPase type 13A2 (ATP13A2); epoxide hydrolase 1, microsomal (xenobiotic) (EPHX1); HtrA serine peptidase 1 (HTRA1); leptin receptor (LEPR); spectrin beta non-erythrocytic 1 (SPTBN1); muscleblind-like 2 (MBNL2); olfactory receptor family 2 subfamily J member 3 (OR2J3); Ras homolog enriched in brain (RHEB); glutamate receptor, ionotropic, N-methyl D-aspartate-associated protein 1 (GRINA); D-box binding protein, promyelocytic leukemia (PML), potassium inwardly-rectifying channel, subfamily J, member 2 (KCNJ2), topoisomerase (DNA) 1 (TOP1) and combinations thereof in the blood sample of the subject can be decreased as compared to the reference expression level to indicate an increase in the risk of suicide in a subject.

A particularly suitable sample for which the expression level of a biomarker is determined can be, for example, blood, including whole blood, leukocytes, and megakaryocytes. Other suitable samples for which the expression level of a biomarker is determined can be, for example, brain, cerebrospinal fluid, olfactory epithelium cells, fibroblasts from skin biopsies, induced pluripotent stem cells, and neuronal-like cells derived therefrom.

While described herein as a change in expression level, in some embodiments, particular levels of one or more of the above-described biomarkers can be useful for objectively identifying subjects at risk for future suicide. For example, it has been found that levels of SAT1 at 2500 Affymetrix microarray fluorescence intensity units (AU) or greater, including 2600 AU or greater, including 2700 AU or greater, including 2800 AU or greater, including 2900 AU or greater, and including 3000 AU or greater, have been found to be at increased risk for future suicide.

In another aspect, the present disclosure is directed to a method for monitoring response of a subject to a treatment for suicidal risk. As used herein, "treatment for suicidal risk" refers to a drug, nutritional, pharmaceutical, or the like, and combinations thereof that can modify the likelihood of a subject attempting and/or completing suicide. The method includes obtaining an expression level of a biomarker; administering a treatment for suicidal risk to the subject; and determining the expression level of the biomarker in a sample obtained from the subject after the treatment is administered, wherein a change in the expression level of the biomarker in the sample obtained from the subject after the treatment is administered as compared to the expression level of the biomarker before the treatment is administered indicates a response to the treatment.

Administration of the treatment can be by any suitable method known by those skilled in the art such as, for example, topical administration, enteral administration and parenteral administration. Suitable methods of administration can be, for example, transdermal administration, oral administration, and injection.

Suitable treatments for suicidal risk can be, for example, clozapine, omega-3 fatty acids (e.g., docosahexaenoic acid (DHA)), lithium, IL-1 trap, canakinumab, nicorandil, amiodarone, arsenic trioxide, vemurafenib, elsamitrucin, T 0128, CT-2106, BN80927, tafluposide, TAS-103, beta-lapachone, irinotecan, topo tecan, 9-amino-20-camptothecin, rubitecan, gimatecan, karenitecin, and combinations thereof.

Response to the treatment can be a decrease in the expression level of a biomarker after treatment. Biomarkers for which a decrease in the expression level of the biomarker indicates a response to the treatment can be, for example, spermidine/spermine N1-acetyltransferase 1 (SAT1); forkhead box N3 (FOXN3); guanylate binding protein 1 (GBP1); phosphoinositide-3-kinase regulatory subunit 5 (PIK3R5); apolipoprotein L2 (APOL2); ATPase H+ transporting lysosomal 9 kDa, V0 subunit e1 (ATP6V0E1); GRINL1A complex locus (GCOM1); lipoma HMGIC fusion partner (LHFP); lipase A (LIPA); myristoylated alanine-rich protein kinase C substrate (MARCKS); 6-phosphogluconolactonase (PGLS); reversion-inducing-cysteine-rich protein with kazal motifs (RECK); tumor necrosis factor (ligand) superfamily member 10 (TNFSF10); ATP-binding cassette, subfamily A (ABC1) member 1 (ABCA1); Rho guanine nucleotide exchange factor (GEF) 40 (ARHGEF4; FLJ10357); cancer susceptibility candidate 1 (CASC1); dehydrogenase/reductase (SDR family) member 9 (DHRS9); disrupted in schizophrenia 1 (DISC1); eukaryotic translation initiation factor 2-alpha kinase 2 (EIF2AK2); uncharacterized LOC727820 (LOC727820); mitogen-activated protein kinase kinase kinase 3 (MAP3K3); mitochondrially encoded NADH dehydrogenase 6 (MT-ND6; ND6); RNA binding motif protein 47 (RBM47); RPTOR independent companion of MTOR complex 2 (RICTOR); sterile alpha motif domain containing 9-like (SAMD9L); scavenger receptor class F member 1 (SCARF1); solute carrier family 36 (proton/amino acid symporter) member 1 (SLC36A1); signal transducer and activator of transcription 1, 91 kDa (STAT1); cytochrome c oxidase subunit Vb (COX5B); SWI/SNF related matrix associated actin dependent regulator of chromatin subfamily a member 1 (SMARCA1); ubiquitin-like modifier activating enzyme 6 (UBA6); zinc finger CCCH-type antiviral 1 (ZC3HAV1); tyrosine kinase, non-receptor 2 (TNK2), and combinations thereof.

Response to the treatment can alternatively be an increase in the expression level of a biomarker after treatment. Biomarkers for which an increase in the expression level of the biomarker indicates a response to the treatment can be, for example, small cell lung carcinoma cluster 4 antigen (CD24; CD24 molecule); ATPase type 13A2 (ATP13A2); epoxide hydrolase 1, microsomal (xenobiotic) (EPHX1); HtrA serine peptidase 1 (HTRA1); leptin receptor (LEPR); spectrin beta non-erythrocytic 1 (SPTBN1); muscleblind-like 2 (MBNL2); olfactory receptor family 2 subfamily J member 3 (OR2J3); Ras homolog enriched in brain (RHEB); glutamate receptor, ionotropic, N-methyl D-aspartate-associated protein 1 (GRINA); D-box binding protein and combinations thereof.

Response to the treatment can be a decrease in the expression level of a first biomarker and an increase in a second biomarker. The first biomarker can be, for example, spermidine/spermine N1-acetyltransferase 1 (SAT1); forkhead box N3 (FOXN3); guanylate binding protein 1 (GBP1); phosphoinositide-3-kinase regulatory subunit 5 (PIK3R5); apolipoprotein L2 (APOL2); ATPase H+ transporting lysosomal 9 kDa, V0 subunit e1 (ATP6V0E1); GRINL1A complex locus (GCOM1); lipoma HMGIC fusion partner (LHFP); lipase A (LIPA); myristoylated alanine-rich protein kinase C substrate (MARCKS); 6-phosphogluconolactonase (PGLS); reversion-inducing-cysteine-rich protein with kazal motifs (RECK); tumor necrosis factor (ligand) superfamily member 10 (TNFSF10); ATP-binding cassette, subfamily A (ABC1) member 1 (ABCA1); Rho guanine nucleotide exchange factor (GEF) 40 (ARHGEF4; FLJ10357); cancer susceptibility candidate 1 (CASC1); dehydrogenase/reductase (SDR family) member 9 (DHRS9); disrupted in schizophrenia 1 (DISC1); eukaryotic translation initiation factor 2-alpha kinase 2 (EIF2AK2); uncharacterized LOC727820 (LOC727820); mitogen-activated protein kinase kinase kinase 3 (MAP3K3); mitochondrially encoded NADH dehydrogenase 6 (MT-ND6; ND6); RNA binding motif protein 47 (RBM47); RPTOR independent companion of MTOR complex 2 (RICTOR); sterile alpha motif domain containing 9-like (SAMD9L); scavenger receptor class F member 1 (SCARF1); solute carrier family 36 (proton/amino acid symporter) member 1 (SLC36A1); signal transducer and activator of transcription 1, 91 kDa (STAT1); cytochrome c oxidase subunit Vb (COX5B); SWI/SNF related matrix associated actin dependent regulator of chromatin subfamily a member 1 (SMARCA1); ubiquitin-like modifier activating enzyme 6 (UBA6); zinc finger CCCH-type antiviral 1 (ZC3HAV1); and combinations thereof. The second biomarker can be, for example, cluster 4 antigen (CD24; CD24 molecule); ATPase type 13A2 (ATP13A2); epoxide hydrolase 1, microsomal (xenobiotic) (EPHX1); HtrA serine peptidase 1 (HTRA1); leptin receptor (LEPR); spectrin beta non-erythrocytic 1 (SPTBN1); muscleblind-like 2 (MBNL2); olfactory receptor family 2 subfamily J member 3 (OR2J3); Ras homolog enriched in brain (RHEB); glutamate receptor, ionotropic, N-methyl D-aspartate-associated protein 1 (GRINA); D-box binding protein, interleukin 1 beta (IL1B), phosphatase and tensin homolog (PTEN), promyelocytic leukemia (PML), potassium inwardly-rectifying channel, subfamily J, member 2 (KCNJ2), topoisomerase (DNA) 1 (TOP1) and combinations thereof. See, Table 5.

In another aspect, the present disclosure is directed to a method for determining suicidal risk as a side-effect of an antidepressant. The method includes obtaining an expression level of a biomarker from the subject; administering an antidepressant to the subject; and determining an expression level of the biomarker in a sample obtained from the subject after the antidepressant is administered. A change in the expression level of the biomarker in the sample obtained from the subject after the antidepressant is administered as compared to the expression level of the biomarker before the antidepressant is administered indicates suicidal risk as a side-effect of the antidepressant.

It is known that suicide risk is a rare, but very serious side-effect of some drugs. Upon initiation of antidepressant therapy, subjects can sometimes experience a sudden onset of suicidal ideation (e.g., suicidal thoughts and behaviors) that accompanies treatment. Subjects can become suicidal in the first weeks of treatment, upon a dosage change and/or a combination thereof. This has caused the U.S. Food and Drug Administration to require manufacturers to place explicit warnings on the label of the drug stating that its use may cause a risk of suicide.

Suitable antidepressants can be, for example, bupropion, citalopram, escitalopram, fluoxetine, fluvoxamine, mirtazapine, nefazodone, paroxetine, sertraline, and venlafaxine.

Suitable biomarkers can be, for example, spermidine/spermine N1-acetyltransferase 1 (SAT1); forkhead box N3 (FOXN3); guanylate binding protein 1 (GBP1); phosphoinositide-3-kinase regulatory subunit 5 (PIK3R5); apolipoprotein L2 (APOL2); ATPase H+ transporting lysosomal 9 kDa, V0 subunit e1 (ATP6V0E1); GRINL1A complex locus (GCOM1); interleukin 1 beta (IL1B); lipoma HMGIC fusion partner (LHFP); lipase A (LIPA); myristoylated alanine-rich protein kinase C substrate (MARCKS); 6-phosphogluconolactonase (PGLS); phosphatase and tensin homolog (PTEN); reversion-inducing-cysteine-rich protein with kazal motifs (RECK); tumor necrosis factor (ligand) superfamily member 10 (TNFSF10); ATP-binding cassette, subfamily A (ABC1) member 1 (ABCA1); Rho guanine nucleotide exchange factor (GEF) 40 (ARHGEF4; FLJ10357); cancer susceptibility candidate 1 (CASC1); dehydrogenase/reductase (SDR family) member 9 (DHRS9); disrupted in schizophrenia 1 (DISC1); eukaryotic translation initiation factor 2-alpha kinase 2 (EIF2AK2); uncharacterized LOC727820 (LOC727820); mitogen-activated protein kinase kinase kinase 3 (MAP3K3); mitochondrially encoded NADH dehydrogenase 6 (MT-ND6; ND6); RNA binding motif protein 47 (RBM47); RPTOR independent companion of MTOR complex 2 (RICTOR); sterile alpha motif domain containing 9-like (SAMD9L); scavenger receptor class F member 1 (SCARF1); solute carrier family 36 (proton/amino acid symporter) member 1 (SLC36A1); signal transducer and activator of transcription 1, 91 kDa (STAT1); cytochrome c oxidase subunit Vb (COX5B); SWI/SNF related matrix associated actin dependent regulator of chromatin subfamily a member 1 (SMARCA1); ubiquitin-like modifier activating enzyme 6 (UBA6); zinc finger CCCH-type antiviral 1 (ZC3HAV1); tyrosine kinase, non-receptor 2 (TNK2); cluster 4 antigen (CD24; CD24 molecule); ATPase type 13A2 (ATP13A2); epoxide hydrolase 1, microsomal (xenobiotic) (EPHX1); HtrA serine peptidase 1 (HTRA1); leptin receptor (LEPR); spectrin beta non-erythrocytic 1 (SPTBN1); muscleblind-like 2 (MBNL2); olfactory receptor family 2 subfamily J member 3 (OR2J3); Ras homolog enriched in brain (RHEB); glutamate receptor, ionotropic, N-methyl D-aspartate-associated protein 1 (GRINA); D-box binding protein, promyelocytic leukemia (PML), potassium inwardly-rectifying channel, subfamily J, member 2 (KCNJ2), topoisomerase (DNA) 1 (TOP1) and combinations thereof. Particularly suitable biomarkers include SAT1, MARCKS, PTEN, MAP3K3, and combinations thereof.

In yet another aspect, the present disclosure is directed to a method of predicting hospitalization of a subject at risk of suicide. The method includes obtaining a first expression level of a blood biomarker in an initial sample obtained from the subject; and determining a second expression level of the blood biomarker in a subsequent sample obtained from the subject, wherein an increase in the expression level of the blood biomarker in the subsequent sample obtained from the subject as compared to the expression level of the initial sample indicates a higher risk of future hospitalizations due to suicidality.

Suitable biomarkers can be, for example, spermidine/spermine N1-acetyltransferase 1 (SAT1); myristoylated alanine-rich protein kinase C substrate (MARCKS); 6-phosphogluconolactonase (PGLS); phosphatase and tensin homolog (PTEN); mitogen-activated protein kinase kinase kinase 3 (MAP3K3); and combinations thereof.

EXAMPLES

Example 1

Materials and Methods

In this Example, whole-genome gene expression profiling of blood samples was conducted to identify blood gene expression biomarkers for suicidality.

Human subjects. Male Caucasian subjects diagnosed with bipolar disorder ("Discovery Cohort") were evaluated that had a diametrical change in suicidal ideation scores from no suicidal ideation to high suicidal ideation from visit to visit. The subjects were limited to minimize any potential gender-related and ethnicity-related state effects on gene expression. A demographic breakdown of the Discovery Cohort subjects is shown in Table 1A.

A "Validation Cohort", in which the top biomarker findings from the Discovery Cohort testing were evaluated, consisted of an age-matched cohort of 9 male suicide completers obtained through the Marion County Coroner's Office (8 Caucasians, 1 African-American) (Table 1B). The subjects in the Validation Cohort were required to have a last observed alive post-mortem interval of 24 hours or less, and had to have completed suicide by means other than overdose, which could affect gene expression.

TABLE 1

Demographics (1) Detailed. (2) Aggregate. Diagnosis established by comprehensive structured clinical interview (DIGS). NOS—not otherwise specified. Suicidal Ideation question is from the Hamilton Rating Scale for Depression obtained at the time of the blood draw for each subject.

(1) A. Discovery Cohort

| SubjectID-Visit | Diagnosis | Age | Gender | Ethnicity | Suicidal Ideation |
|---|---|---|---|---|---|
| phchp023v1 | Bipolar Disorder NOS | 52 | M | Caucasian | 0 |
| phchp023v2 | Bipolar Disorder NOS | 52 | M | Caucasian | 3 |
| phchp023v3 | Bipolar Disorder NOS | 52 | M | Caucasian | 0 |
| phchp093v1 | Bipolar I Disorder | 51 | M | Caucasian | 0 |
| phchp093v2 | Bipolar I Disorder | 51 | M | Caucasian | 0 |
| phchp093v3 | Bipolar I Disorder | 52 | M | Caucasian | 3 |
| phchp095v1 | Bipolar I Disorder | 28 | M | Caucasian | 3 |
| phchp095v2 | Bipolar I Disorder | 29 | M | Caucasian | 0 |
| phchp095v3 | Bipolar I Disorder | 29 | M | Caucasian | 2 |
| phchp122v1 | Bipolar Disorder NOS | 51 | M | Caucasian | 0 |
| phchp122v2 | Bipolar Disorder NOS | 51 | M | Caucasian | 2 |
| phchp128v1 | Bipolar I Disorder | 45 | M | Caucasian | 2 |
| phchp128v2 | Bipolar I Disorder | 45 | M | Caucasian | 0 |
| phchp136v1 | Bipolar I Disorder | 41 | M | Caucasian | 0 |
| phchp136v2 | Bipolar I Disorder | 41 | M | Caucasian | 0 |
| phchp136v3 | Bipolar I Disorder | 41 | M | Caucasian | 3 |
| phchp153v1 | Bipolar II Disorder | 55 | M | Caucasian | 0 |
| phchp153v2 | Bipolar II Disorder | 55 | M | Caucasian | 2 |
| phchp153v3 | Bipolar II Disorder | 56 | M | Caucasian | 0 |
| phchp179v1 | Bipolar Disorder NOS | 36 | M | Caucasian | 0 |
| phchp179v2 | Bipolar Disorder NOS | 37 | M | Caucasian | 0 |
| phchp179v3 | Bipolar Disorder NOS | 37 | M | Caucasian | 3 |
| phchp183v1 | Bipolar I Disorder | 48 | M | Caucasian | 3 |
| phchp183v2 | Bipolar I Disorder | 48 | M | Caucasian | 0 |

B. Validation Cohort

| SubjectID | Psychiatric Diagnosis | Age | Gender | Ethnicity | Suicide |
|---|---|---|---|---|---|
| INBR009 | Bipolar/Schizophrenia | 59 | M | Caucasian | Hanging |
| INBR011 | Depression/ADHD | 26 | M | Caucasian | GSW to chest |
| INBR012 | Unknown | 39 | M | Caucasian | GSW to head |
| INBR013 | Depression | 68 | M | African-American | GSW to mouth |
| INBR014 | None | 27 | M | Caucasian | Hanging |
| INBR015 | None | 40 | M | Caucasian | Hanging |
| INBR016 | Anxiety/TBI | 68 | M | Caucasian | GSW to head |
| INBR017 | Depression | 56 | M | Caucasian | GSW to chest |
| INBR018 | None | 65 | M | Caucasian | Slit wrist |

TABLE 1-continued

Demographics (1) Detailed. (2) Aggregate. Diagnosis established by comprehensive structured clinical interview (DIGS). NOS—not otherwise specified. Suicidal Ideation question is from the Hamilton Rating Scale for Depression obtained at the time of the blood draw for each subject.

(2)

| Discovery Cohort | Suicidal Ideation | | |
|---|---|---|---|
| SI (score) | No SI (0) | High SI (2-4) | Overall |
| Number of subjects (number of chips) | 9(14) | 9(10) | 9(24) |
| Age mean years (SD) | 46.1 (8.1) | 43.8 (9.7) | 45.1 (8.7) |
| range | 29-56 | 28-55 | 28-56 |
| Ethnicity # subjects (Caucasian/African-American) | (9/0) | (9/0) | (9/0) |

| Test Cohort | Suicide Completers | | |
|---|---|---|---|
| Number of subjects (number of chips) | 9(9) | | |
| Age mean years (SD) | 49.8 (17) | | |
| range | 26-68 | | |
| Ethnicity # subjects (Caucasian/African-American) | (8/1) | | |

The Discovery Cohort subjects were on a variety of different psychiatric medications, including mood stabilizers, antidepressants, antipsychotics, benzodiazepines, and others as listed in Table 2A (Table 2B provides toxicology for subjects in the coroner's office test cohort-suicide completers). Medications can have a strong influence on gene expression. However, this Example tested differentially expressed genes based at on intra-subject analyses, which factor out not only genetic background, effects but also medication effects. Moreover, there was no consistent pattern found in any particular type of medication, or between any change in medications and suicidal ideation in the rare instances where there were changes in medications between visits. Subjects were excluded, however, if they had significant acute medical or neurological illnesses, or had evidence of active substance abuse or dependence.

TABLE 2A

Psychiatric medications of Discovery Cohort subjects.

| SubjectID-Visit | Psychiatric Medications |
|---|---|
| phchp023v1 | FLEXARIL 10 MG FOR SLEEP PRN<br>LAMOTRIGINE 200 MG<br>ZIPRASIDONE 60 MG |
| v2 | FLEXARIL 10 MG FOR SLEEP PRN<br>LAMOTRIGINE 200 MG<br>ZIPRASIDONE 60 MG |
| v3 | FLEXARIL 10 MG FOR SLEEP PRN<br>LAMOTRIGINE 200 MG<br>ZIPRASIDONE 60 MG |

TABLE 2A-continued

Psychiatric medications of Discovery Cohort subjects.

| SubjectID-Visit | Psychiatric Medications |
|---|---|
| Phchp093v1 | CITALOPRAM HYDROBROMIDE 40 MG TAB TAKE ONE-HALF TABLET ORALLY EVERY DAY<br>VALPROIC ACID 500 MG 24 HR (ER) SA TAB TAKE THREE TABLETS ORALLY AT BEDTIME<br>QUETIAPINE FUMARATE 100 MG TAB TAKE ONE TABLET ORALLY AT BEDTIME<br>GABAPENTIN 300 MG CAP TAKE ONE CAPSULE ORALLY AT BEDTIME FOR 3 DAYS, THEN TAKE ONE CAPSULE, TWICE A DAY<br>QUETIAPINE FUMARATE 25 MG TAB TAKE ONE TABLET ORALLY EVERY DAY AS NEEDED |
| v2 | CITALOPRAM HYDROBROMIDE 40 MG TAB TAKE ONE-HALF TABLET ORALLY EVERY DAY<br>VALPROIC ACID 500 MG 24 HR (ER) SA TAB TAKE THREE TABLETS ORALLY AT BEDTIME<br>DOXEPIN HCL 10 MG CAP TAKE ONE CAPSULE ORALLY AT BEDTIME<br>GABAPENTIN 300 MG CAP TAKE TWO CAPSULES ORALLY TWICE A DAY AND TAKE THREE CAPSULES AT BEDTIME<br>QUETIAPINE FUMARATE 100 MG TAB TAKE ONE TABLET ORALLY AT BEDTIME<br>QUETIAPINE FUMARATE 25 MG TAB TAKE ONE TABLET ORALLY EVERY DAY |
| v3 | CITALOPRAM HYDROBROMIDE 40 MG TAB TAKE ONE-HALF TABLET ORALLY EVERY DAY<br>VALPROIC ACID 500 MG 24 HR (ER) SA TAB TAKE THREE TABLETS ORALLY AT BEDTIME<br>DOXEPIN HCL 10 MG CAP TAKE ONE CAPSULE OLLY AT BEDTIME |

TABLE 2A-continued

Psychiatric medications of Discovery Cohort subjects.

| SubjectID-Visit | Psychiatric Medications |
|---|---|
| | GABAPENTIN 300 MG CAP TAKE TWO CAPSULES ORALLY TWICE A DAY WITH FOOD |
| | QUETIAPINE FUMARATE 100 MG TAB TAKE ONE TABLET ORALLY PENDING AT BEDTIME |
| | QUETIAPINE FUMARATE 25 MG TAB TAKE ONE TABLET ORALLY EVERY DAY |
| Phchp095v1 | VALPROIC ACID 250 MG 24 HR (ER) SA TAB TAKE SEVEN TABLETS ORALLY AT BEDTIME |
| | RISPERIDONE 2 MG TAB TAKE ONE TABLET ORALLY EVERY DAY |
| | SERTRALILNE HCL 100 MG TAB TAKE ONE TABLET ORALLY EVERY DAY |
| v2 | VALPROIC ACID 250 MG 24 HR (ER) SA TAB TAKE SEVEN TABLETS ORALLY AT BEDTIME |
| | RISPERIDONE 2 MG TAB TAKE ONE TABLET ORALLY EVERY DAY |
| | SERTRALINE HCL 100 MG TAB TAKE ONE TABLET ORALLY EVERY DAY |
| v3 | BENZTROPINE MESYLATE ORAL 1 MG TAB TAKE ONE TABLET ORALLY TWICE A DAY |
| | TRAZODONE 100 MG TAB TAKE ONE TABLET ORALLY AT BEDTIME |
| | RISPERIDONE 4 MG TAB TAKE ONE TABLET ORALLY EVERY DAY |
| | LORAZEPAM INJ IM Q4H PRN 2 MG/1 ML |
| | LORAZEPAM TAB PO Q6H PRN 2 MG |
| Phchp122v1 | AMITRIPTYLINE HCL 10 MG TAB TAKE ONE TABLET ORALLY THREE TIMES DAILY AT 10AM, 2PM AND 10PM |
| | LEVETIRACETAM 500 MG TAB TAKE ONE TABLET ORALLY TWICE A DAY |
| | LORAZEPAM 0.5 MG TAB TAKE 1 TABLET ORALLY TWICE A DAY |
| | LUBRICATING (PF) OPH OINT APPLY ½ INCH RIBBON IN BOTH EYES AT BEDTIME |
| | RISPERIDONE 4 MG TAB TAKE ONE-HALF TABLET ORALLY AT BEDTIME |
| | TOPIRAMATE 25 MG TAB TAKE ONE TABLET ORALLY TWICE A DAY; INCREASE AS DIRECTED TO TWO TABLETS TWICE A DAY |
| | TRAZODONE 100 MG TAB TAKE ONE TABLET ORALLY AT BEDTIME AS NEEDED FOR INSOMNIA |
| v2 | VALPROIC ACID 500 MG 24 HR (ER) SA TAB TAKE TWO TABLETS ORALLY AT BEDTIME |
| | LORAZEPAM 1 MG TAB TAKE TWO TABLETS ORALLY AT BEDTIME AS NEEDED FOR INSOMNIA |
| | MIRTAZAPINE 30 MG TAB TAKE ONE TABLET ORALLY AT BEDTIME |
| | PRAZOSIN 2 MG CAP TAKE ONE CAPSULE ORALLY TWICE A DAY. TAKE SECOND DOSE AT BEDTIME. |
| | VENLAFAXINE HCL 150 MG 24 HR SA TAB TAKE ONE TABLET ORALLY TWICE A DAY (BREAKFAST AND LUNCH) |
| | ZIPRASIDON 80 MG CAP TAKE TWO CAPSULES ORALLY EVERY EVENING WITH DINNER |
| phchp128v1 | DISULFIRAM 250 MG TAB TAKE ONE TABLET ORALLY EVERY DAY |
| | VALPROIC ACID 500 MG 24 HR (ER) SA TAB TAKE THREE TABLETS ORALLY AT BEDTIME |
| | TRAZODONE 50 MG TAB TAKE ONE TABLET ORALLY AT BEDTIME AS NEEDED FOR INSOMNIA |
| V2 | DISULFIRAM 250 MG TAB TAKE ONE TABLET ORALLY EVERY DAY |
| | VALPROIC ACID 500 MG 24 HR (ER) SA TAB TAKE THREE TABLETS ORALLY AT BEDTIME |
| | TRAZODONE 50 MG TAB TAKE ONE TABLET ORALLY AT BEDTIME AS NEEDED FOR INSOMNIA |
| PHCHP136V1 | BENZTROPINE MESYLATE ORAL MESYLATE 1 MG TAB TAKE ONE TABLET ORALLY TWICE A DAY |
| | CHLORPROMAZINE 100 MG TAB TAKE ONE TABLET ORALLY AT BEDTIME |
| | HALOPERIDOL DECANOATE 5 ML(100 MG/ML) INJ INJECT 200 MG HOLD(2 ML) INTRAMUSCULAR EVERY 4 WEEKS |
| | OXCARBAZEPINE 300 MG TAB TAKE ONE TABLET ORALLY EVERY MORNING AND TAKE THREE TABLETS AT BEDTIME |
| | FISH OIL CAP/TAB |
| v2 | BENZTROPINE MESYLATE ORAL MESYLATE 2 MG TAB TAKE ONE TABLET ORALLY TWICE A DAY |
| | CHLORPROMAZINE 100 MG TAB TAKE ONE TABLET ORALLY AT BEDTIME |
| | HALOPERIDOL DECANOATE 5 ML(100 MG/ML) NJ INJECT 200 MG HOLD (2 ML) INTRAMUSCULAR EVERY 4 WEEKS |
| | OXCARBAZEPINE 300 MG TAB TAKE ONE TABLET ORALLY EVERY MORNING AND TAKE THREE TABLETS AT BEDTIME |
| v3 | BENZTROPINE MESYLATE ORAL MESYLATE 2 MG TAB TAKE ONE TABLET ORALLY TWICE A DAY |
| | CHLORPROMAZINE 100 MG TAB TAKE ONE TABLET ORALLY AT BEDTIME |
| | HALOPERIDOL DECANOATE 5 ML(100 MG/ML) INJ INJECT 200 MG HOLD(2 ML) INTRAMUSCULAR EVERY 4 WEEKS |
| | OXCARBAZEPINE 300 MG TAB TAKE ONE TABLET ORALLY EVERY MORNING AND TAKE THREE TABLETS AT BEDTIME |
| Phchp153v1 | TRAZODONE 50 MG TAB TAKE ONE TO ONE AND ONE-HALF TABLETS ORALLY AT BEDTIME |
| | VENLAFAXINE HCL 225 MG 24 HR SA TAB TAKE ONE TABLET ORALLY EVERY DAY WITH BREAKFAST |
| v2 | TRAZODONE 100 MG TAB TAKE ONE TABLET ORALLY AT BEDTIME |
| | VENLAFAXINE HCL 225 MG 24 HR SA TAB TAKE ONE TABLET ORALLY EVERY DAY WITH BREAKFAST |
| v3 | VENLAFAXINE HCL 150 MG 24 HR SA TAB-1X PER DAY |
| | TRAZADONE HCL 50 MG-1X PER DAY |
| Phchp179v1 | LISDEXAMFETAMINE (40 MG) |
| | QUETIAPINE (600 MG) |
| | PAROXETINE (30 MG) |
| | ALPRAZOLAM (½ MG PER NIGHT) |
| | ZOLPIDEM (10 MG PER NIGHT) |
| v2 | No Psychiatric Medication |
| v3 | QUETIAPINE 100 MG-IS BEING TAPERED OFF |
| | ZIPRASIDONE 120 MG |
| | PAROXETINE 30 MG |
| | ALPRAZOLAM unknown dosage, PRN |
| | LISDEXAMFETAMINE 50 MG |
| PHCHP183V1 | ARIPIPRAZOLE TAB 20 MG PO DAILY |
| | BENZTROPINE MESYLATE ORAL TAB 1 MG PO Q4H PRN |
| | VALPROIC ACID TAB, SA, 24 HR (EXPENDED 2000 MG PO BEDTIME |
| | HALOPERIDOL INJ, SOLN 5 MG IM Q4H PRN |
| | HALOPERIDOL TAB 5 MG PO Q4H PRN |
| | HYDROXYZINE PAMOATE CAP, ORAL 25 MG PO Q6H PRN |
| | LORAZEPAM INJ 2 MG/1 ML IM Q4H PRN |
| | RISPERIDONE TAB 1 MG PO BID |
| | HYDROXYZINE PAMOATE 25 MG CAP TAKE ONE CAPSULE ORALLY EVERY 6 HOURS AS NEEDED FOR ANXIETY |
| | RISPERIDONE 1 MG TAB TAKE ONE-HALF TABLET ORALLY TWICE A DAY |
| | FISH OIL CAP/TAB ORALLY |
| v2 | ARIPIPRAZOLE 20 MG TAB TAKE ONE TABLET ORALLY EVERY DAY |
| | HYDROXYZINE PAMOATE 25 MG CAP TAKE ONE CAPSULE ORALLY EVERY 6 HOURS AS NEEDED FOR ANXIETY |
| | CITALOPRAM HYDROBROMIDE 10 MG TAB TAKE ONE-HALF TABLET ORALLY EVERY MORNING |

TABLE 2B

Toxicology for subject in the coroner's office test cohort-suicide completers

| SubjectID | Toxicology |
| --- | --- |
| INBR009 | |
| INBR011 | ALPRAZOLAM 3.2 NG/ML |
| | TRAMADOL 331 NG/ML |
| | NORTRAMADOL 179 NG/ML |
| | BUPROPION 136 NG/ML |
| | CITALOPRAM/ESCITALOPRAM 229 NG/ML |
| | CAFFEINE POSITIVE |
| | COTININE POSITIVE |
| INBR012 | Not Available |
| INBR013 | CAFFEINE POSITIVE |
| INBR014 | ETHANOL 0.15% (W/V) |
| | CAFFEINE |
| INBR015 | ETHANOL 0.119% (W/V) |
| | CAFFEINE |
| INBR016 | Not Available |
| INBR017 | Not Available |
| INBR018 | ETHANOL 0.057% (W/V) |
| | AMIODARONE |
| | CAFFEINE |
| | COTININE |

The subjects were subjected to diagnostic assessments using Diagnostic Interview for Genetic Studies, which is the scale used by the Genetics Initiative Consortia for both bipolar disorder and major depression, at a baseline visit, followed by up to three testing visits, three to six months apart. Particularly, six subjects were subjected to three follow-up testing visits and three subjects were subjected to two follow-up testing visits, resulting in a total of 24 blood samples for subsequent microarray studies as discussed herein. At each testing visit, the subjects received a series of psychiatric rating scales, including the Hamilton Rating Scale for Depression (HAMD-17), which includes a suicidal ideation rating item (FIG. 1B), and blood was drawn. The suicidal ideation scores varied during the visits from no ideation to high suicidal ideation.

Gene Expression Analysis

Using the nine subjects with multiple visits, corresponding to 24 chips, from the Discovery Cohort a differential analysis was run using Partek Genomic Suites 6.6 software package (Partek Incorporated, St. Louis, Mo.). Normalization was performed on all 24 chips by robust multi-array analysis (RMA), background corrected with quartile normalization and a median polish probe set summarization of all 24 chips to obtain the normalized expression levels of all probe sets for each chip. Two analyses, an intra-subject analysis and an inter-subject analysis, were conducted to establish a list of differentially expressed probe sets.

RNA extraction. During each visit, from about 2.5 ml to about 5.0 ml of whole blood was collected from the subjects separately into two PaxGene tubes, treated to stabilize RNA, by routine venipuncture. The cells from the whole blood were concentrated by centrifugation, the pellet washed, resuspended and incubated in buffers containing proteinase K for protein digestion. A second centrifugation step was conducted to remove residual cell debris. Ethanol was added. After ethanol addition, the supernatant was applied to a silica-gel membrane/column. The column was centrifuged and contaminants were removed in three wash steps. RNA bound to the membrane was then eluted using DEPC-treated water.

Globin reduction. To remove globin mRNA, total RNA from the whole blood was mixed with a biotinylated Capture Oligo Mix that is specific for human globin mRNA. The mixture was then incubated for 15 minutes to allow the biotinylated oligonucleotides to hybridize with the globin mRNA. Streptavidin magnetic beads were then added, and the mixture was incubated for 30 minutes. During this incubation, streptavidin binds to the biotinylated oligonucleotides, thereby capturing the globin mRNA on the magnetic beads. The streptavidin magnetic beads were then pulled to the side of the tube with a magnet, and the RNA, depleted of the globin mRNA, was transferred to a fresh tube. The treated RNA was further purified using a rapid magnetic bead-based purification method consisting of adding an RNA binding bead suspension to the samples and using magnetic capture to wash and elute the globin-clear RNA.

Sample labeling. Samples were labeled using an Ambion MessageAmp II-BiotinEnhanced antisense RNA (aRNA) amplification kit. The procedure involved the following steps:

1) Reverse transcription to synthesize first strand cDNA was primed with T7 Oligo(dT) primer to synthesize cDNA containing a T7 promoter sequence.
2) Second strand cDNA synthesis converted the single-stranded cDNA into a double-stranded DNA (dsDNA) template for transcription. The reaction employed DNA polymerase and RNase H to simultaneously degrade the RNA and synthesize second strand cDNA.
3) cDNA purification removed RNA, primers, enzymes, and salts that would inhibit in vitro transcription.
4) In vitro transcription to synthesize aRNA with biotin-NTP mix generated multiple copies of biotin-modified aRNA from the double-stranded cDNA templates; this was the amplification step.
5) aRNA purification removed unincorporated NTPs, salts, enzymes, and inorganic phosphate to improve the stability of the biotin-modified aRNA.
6) aRNA fragmentation in a reaction that employs a metal-induced hydrolysis. The fragmented labeled aRNA is then ready for hybridization to the Affymetrix microarray chip.

Microarrays. Biotin-labeled aRNA was then hybridized to Affymetrix HG-U133 Plus 2.0 GeneChips (Affymetrix, Santa Clara, Calif.) with over 40,000 genes and expressed sequence tags (ESTs) according to manufacturer's protocols (www.affymetrix.com/support/technical/manual/expression_manual.affx). All GAPDH 3'/5' ratios should be less than 2.0 and backgrounds under 50. Arrays were stained using standard Affymetrix protocols for antibody signal amplification and scanned on an Affymetrix GeneArray 2500 scanner with a target intensity set at 250. Present/absent calls were determined using GCOS software with thresholds set at default values. Quality control measures including 30/50 ratios for glyceraldehyde 3-phosphate dehydrogenase and b-actin, scale factors, background and Q values were within acceptable limits.

Analysis. Each subject's suicidal ideation (SI) scores at time of blood collection (0—no SI compared to 2 and above—high SI) were used for analysis. Particularly, gene expression differences between the no SI and the high SI states using both an intra-subject and an inter-subject design as shown in FIG. 1A were analyzed.

An intra-subject analysis using a fold change in expression of at least 1.2 between high and no suicidal ideation visits within each subject was performed. There were in total 15 comparisons. Probe sets that had a 1.2 fold change were then assigned either a 1 (increased in high suicidal ideation) or a −1 (decreased in high suicidal ideation) in each comparison. These values were then summed for each probe set across the 15 comparisons, yielding a range of scores between −11 and 12. Probe sets in the top 5% (1,269 probe sets, <5% of 54,675 total probe sets) had an absolute value of 7 and greater, receiving an internal Convergent Functional Genomics (CFG) score of 1 point. Those probe sets in the top 0.1% (24 probe sets, <0.1% of 54,675 total probe sets) had a total absolute value of 11 and greater and received an internal CFG score of 3 points.

Additionally, an inter-subject analysis using t-test (2-tailed, unequal variance) was performed to find probes differentially expressed between high suicidal ideation and no suicidal ideation chips (FIG. 1A), resulting in 648 probe sets with P<0.05. Probe sets with a P<0.05 received an internal CFG score of 1 point, while probe sets with P<0.001 received 3 points.

Results were then further filtered by only selecting probe sets that overlapped between the intra-subject and the inter-subject analyses, resulting in 279 probe sets corresponding to 246 unique genes. Gene names for the probe sets were identified using Partek as well as NetAffyx (Affymetrix) for Affymetrix HG-U133 Plus 2.0 GeneChips, followed by GeneCards to confirm the primary gene symbol. In addition, for those probe sets that were not assigned a gene name by Partek or NetAffyx, the UCSC Genome Browser on Human February 2009 (GRCh37/hg19) was used to directly map them to known genes. Genes were then scored using manually curated CFG databases as described below and shown in FIG. 2.

Convergent Functional Genomics (CFG) Databases

Manually curated databases were created in the Laboratory of Neurophenomics, Indiana University School of Medicine (www.neurophenomics.info) of all the human gene expression (postmortem brain, blood, cell cultures), human genetic (association, CNVs, linkage) and animal model gene expression and genetic studies published to date on psychiatric disorders. Only the findings deemed significant in the primary publication, by the study authors, using their particular experimental design and thresholds, were included in the databases. The databases included only primary literature data and did not include review papers or other secondary data integration analyses to avoid redundancy and circularity. These large and constantly updated databases have been used in previous CFG cross-validation and prioritization studies.

Human Postmortem Brain Gene Expression Evidence. Information about genes was obtained and imported in the databases searching the primary literature with PubMed (ncbi.nlm.nih.gov/PubMed), using various combinations of keywords (e.g., gene name and suicide and human brain). Postmortem convergence was deemed to occur for a gene if there were published reports of human postmortem data showing changes in expression of that gene in brains from patients who died from suicide.

Human Genetic Evidence Association and Linkage. To designate convergence for a particular gene, the gene had to have independent published evidence of association or linkage for suicide. For linkage, the location of each gene was obtained through GeneCards (www.genecards.org), and the sex averaged cM location of the start of the gene was then obtained through compgen.rutgers.edu/old/map-interpolator/. For linkage convergence, the start of the gene had to map within 5cM of the location of a marker linked to the disorder.

CFG Scoring. For CFG analysis, two external cross-validating lines of evidence were weighed such that findings in human postmortem brain tissue, the target organ, were prioritized over genetic findings. Human brain expression evidence was given 4 points, while human genetic evidence was given a maximum of 2 points for association, and 1 point for linkage. Each line of evidence was capped in such a way that any positive findings within that line of evidence resulted in maximum points regardless of how many different studies support that single line of evidence, to avoid potential popularity biases.

In addition to the above external CFG score, genes based upon the initial differential expression analyses used to identify them were also prioritized. Probe sets identified by differential expression analyses could receive a maximum of 6 points (1 or 3 points from intra-subject analyses, and 1 or 3 points from inter-subject analyses). Thus, the maximum possible total CFG score for each gene was 12 points (6 points for internal score+6 points for external score).

Figure 2:
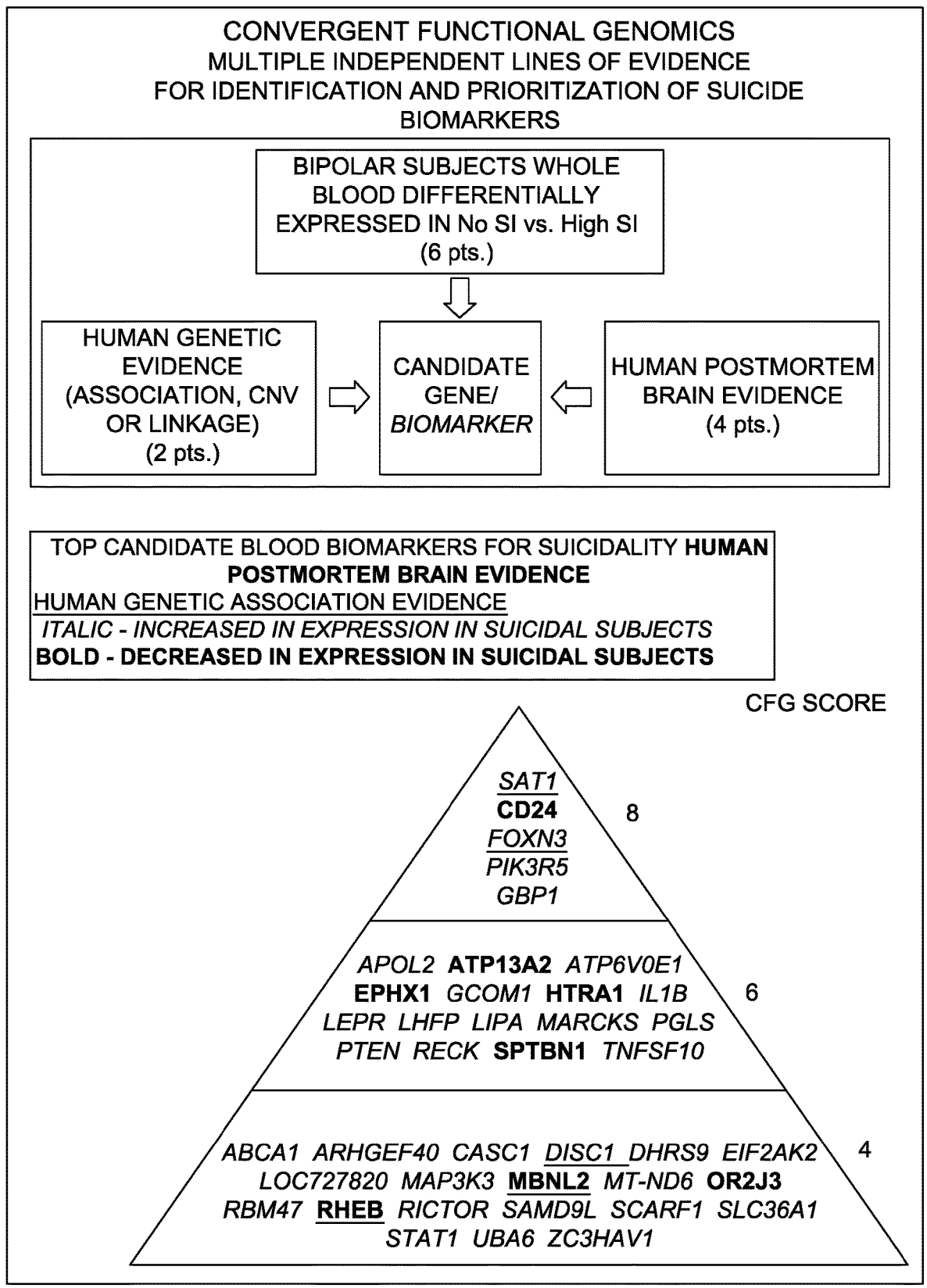
FIG. 2 depicts the convergent functional genomics (CFG) approach for identification and prioritization of genomic biomarkers for suicidality as discussed in Example 1.

The above-described scoring system provided a good separation of genes based on differential expression and on independent cross-validating evidence in the field (FIG. 2).

Pathway Analyses

IPA 9.0 (Ingenuity Systems, www.ingenuity.com, Redwood City, Calif.) was used to analyze the biological roles, including top canonical pathways and diseases, of the candidate genes resulting from the above findings (Table 3), as well as used to identify genes in the data sets that were the target of existing drugs (Table 4). Pathways were identified from the IPA library of canonical pathways that were most significantly associated with genes in the data set. The significance of the association between the data set and the canonical pathway was measured in two ways: 1) a ratio of the number of molecules from the data set that map to the pathway divided by the total number of molecules that map to the canonical pathway is displayed; and 2) Fisher's exact test was used to calculate a p-value determining the probability that the association between the genes in the data set and the canonical pathway was explained by chance alone. A KEGG pathway analysis through the Partek Genomic Suites 6.6 software package was also conducted.

TABLE 3

Ingenuity Pathway Analyses.
A. Pathways.
B. Disease and Disorders.

A.

| | | INGENUITY Pathways | | | KEGG Pathways | | |
|---|---|---|---|---|---|---|---|
| | # | Top Canonical Pathways | P-Value | Ratio | Pathway Name | Enrichment Score | Enrichment p-value |
| CFG score >= 6.0 | 1 | Role of Tissue Factor in Cancer | 2.63E−04 | 3/115 (0.026) | Apoptosis | 6.69102 | 0.001242 |
| N = 21 genes | 2 | Dendritic Cell Maturation | 9.83E−04 | 3/207 (0.014) | Measles | 6.06369 | 0.002326 |

TABLE 3-continued

Ingenuity Pathway Analyses.
A. Pathways.
B. Disease and Disorders.

|  | # | Pathway | P-Value | Ratio | Disease/Pathway | Score | P-Value |
|---|---|---|---|---|---|---|---|
|  | 3 | Melanoma Signaling | 1.13E−03 | 2/46 (0.043) | Endometrial cancer | 4.96787 | 0.006958 |
|  | 4 | Docosahexaenoic Acid (DHA) Signaling | 1.18E−03 | 2/49 (0.041) | Influenza A | 4.90223 | 0.00743 |
|  | 5 | Endometrial Cancer Signaling | 1.69E−03 | 2/57 (0.035) | Phosphatidyl-inositol signaling system | 4.85448 | 0.007793 |
| CFG score >= 4.0 N = 41 genes | 1 | NF-kB Signaling | 4.42E−04 | 4/175 (0.023) | Measles | 8.7667 | 0.000156 |
|  | 2 | Dendritic Cell Maturation | 5.38E−04 | 4/207 (0.019) | Influenza A | 6.87308 | 0.001035 |
|  | 3 | PDGF Signaling | 7.5E−04 | 3/85 (0.035) | mTOR signaling pathway | 6.34986 | 0.001747 |
|  | 4 | Role of Pattern Recognition Receptors in Recognition of Bacteria and Viruses | 1.14E−03 | 3/106 (0.028) | Apoptosis | 4.75687 | 0.008592 |
|  | 5 | Role of Tissue Factor in Cancer | 1.78E−03 | 3/115 (0.026) | Toll-like receptor signaling pathway | 4.37269 | 0.012617 |
| All genes differentially expressed N = 246 genes (279 probe sets) | 1 | Retinoic acid Mediated Apoptosis Signaling | 1.12E−03 | 5/69 (0.072) | Ubiquitin mediated proteolysis | 4.80416 | 0.0081956 |
|  | 2 | Role of PKR in Interferon Induction and Antiviral Response | 1.19E−03 | 4/46 (0.087) | Herpes simplex infection | 4.14288 | 0.0158771 |
|  | 3 | UVA-induced MAPK Signaling | 3.90E−03 | 5/92 (0.054) | Phagosome | 4.0301 | 0.0177725 |
|  | 4 | Dendritic Cell Maturation | 4.71E−03 | 7/207 (0.034) | Measles | 3.72158 | 0.0241958 |
|  | 5 | Role of Pattern Recognition Receptors in Recognition of Bacteria and Viruses | 5.38E−03 | 5/106 (0.047) | Influenza A | 5.03358 | 0.0065155 |

B.
INGENUITY

|  | # | Diseases and Disorders | P-Value | # Molecules |
|---|---|---|---|---|
| CFG score >= 6.0 N = 21 genes | 1 | Cancer | 1.22E−06-4.54E−03 | 14 |
|  | 2 | Connective Tissue Disorders | 2.19E−04-3.41E−03 | 8 |
|  | 3 | Inflammatory Disease | 2.19E−04-4.54E−03 | 8 |
|  | 4 | Skeletal and Muscular Disorders | 2.19E−04-4.42E−03 | 9 |
|  | 5 | Gastrointestinal Disease | 2.22E−04-4.54E−03 | 12 |
| CFG score >= 4.0 N = 41 genes | 1 | Cancer | 4.51E−06-6.45E−03 | 20 |
|  | 2 | Inflammatory Response | 2.70E−05-6.45E−03 | 12 |
|  | 3 | Antimicrobial Response | 9.95E−05-6.45E−03 | 4 |
|  | 4 | Infectious Disease | 1.25E−04-5.52E−03 | 6 |
|  | 5 | Connective Tissue Disorders | 1.53E−04-6.45E−03 | 11 |

TABLE 4

Ingenuity drug targets analysis. Repositioning of existing drugs for treating suicidality.

| | CFG Score | Direction of change | Location | Type(s) | Drug(s) |
|---|---|---|---|---|---|
| IL1B interleukin 1, beta | 8 | I | Extracellular Space | cytokine | IL-1 trap, canakinumab |
| KCNJ2 potassium inwardly-rectifying channel, subfamily J, member 2 | 4 | I | Plasma Membrane | ion channel | nicorandil, amiodarone |
| PML promyelocytic leukemia | 4 | I | Nucleus | transcription regulator | arsenic trioxide |
| TNK2 tyrosine kinase, non-receptor, 2 | 4 | D | Cytoplasm | kinase | vemurafenib |
| TOP1 topoisomerase (DNA) I | 2 | I | Nucleus | enzyme | elsamitrucin, T 0128, CT-2106, BN 80927, tafluposide, TAS-103, beta-lapachone, irinotecan, topotecan, 9-amino-20-camptothecin, rubitecan, gimatecan, karenitecin |

Validation Analyses

Figure 3G:
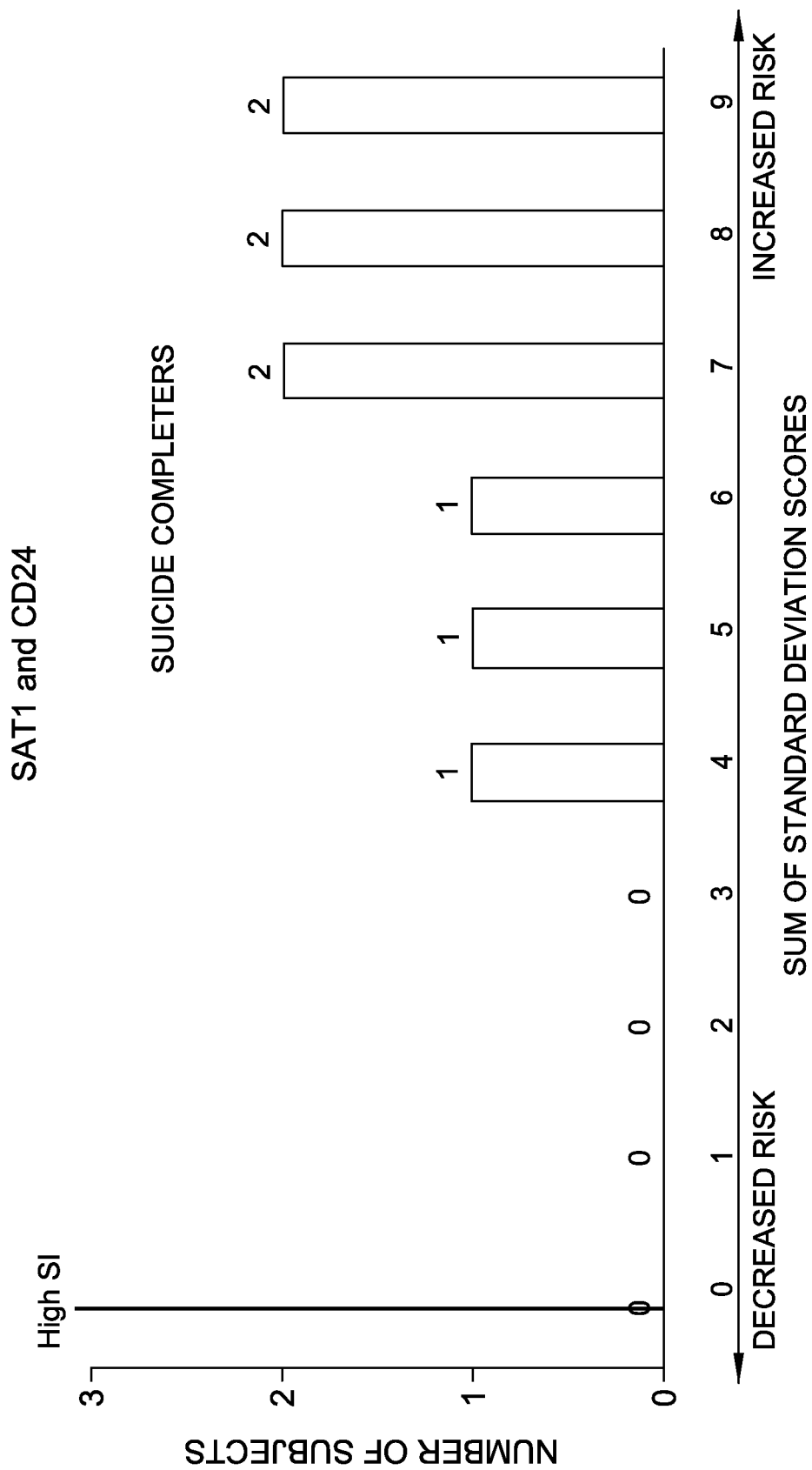

The nine Affymetrix microarray data files from the Validation Cohort was imported as .cel files into Partek Genomic Suites 6.6 software package (Partek Incorporated St. Louis, Mo.). A robust multi-array analysis (RMA), background corrected with quartile normalization and a median polish probe set summarization of all 24+9=33 chips was conducted to obtain the normalized expression levels of all probe sets for each chip. Partek normalizes expression data into a log base of 2 for visualization. The data was non-log by taking 2 to the power of the transformed expression value. The non-log transformed expression data was then used to compare expression levels of SAT1 and CD24 in the different groups (FIG. 3G).

Figures 3H, 3I:
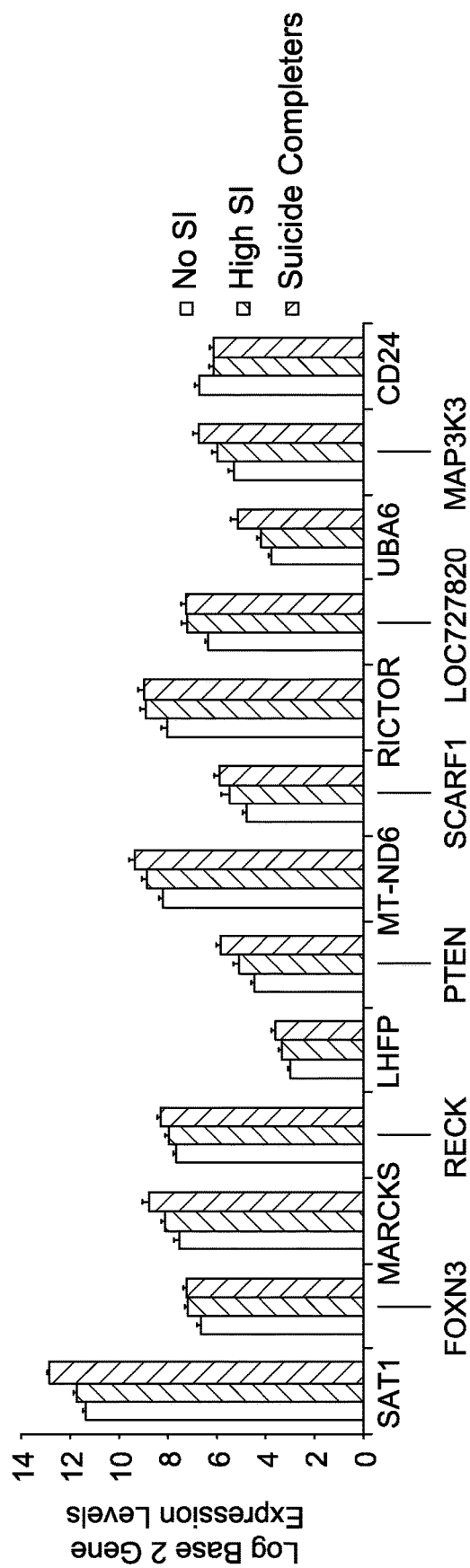
Figure 4A:
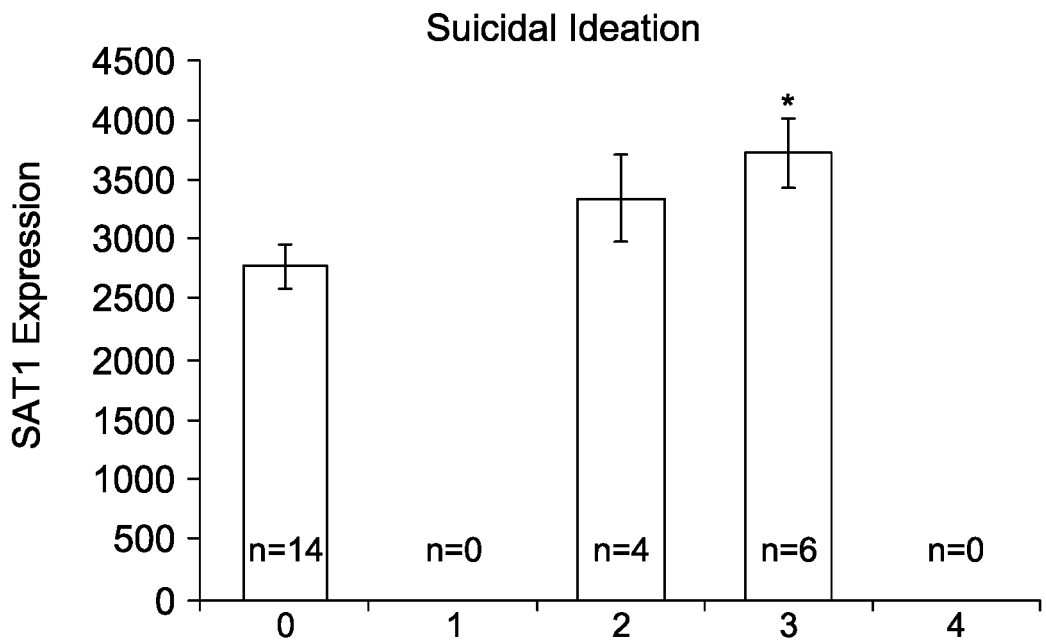
FIGS. 4A-F depict SAT1 expression in the bipolar discovery cohort: relationship with suicidal ideation, mood, psychosis, anxiety, and stress as discussed in Example 1.
Figure 4B:
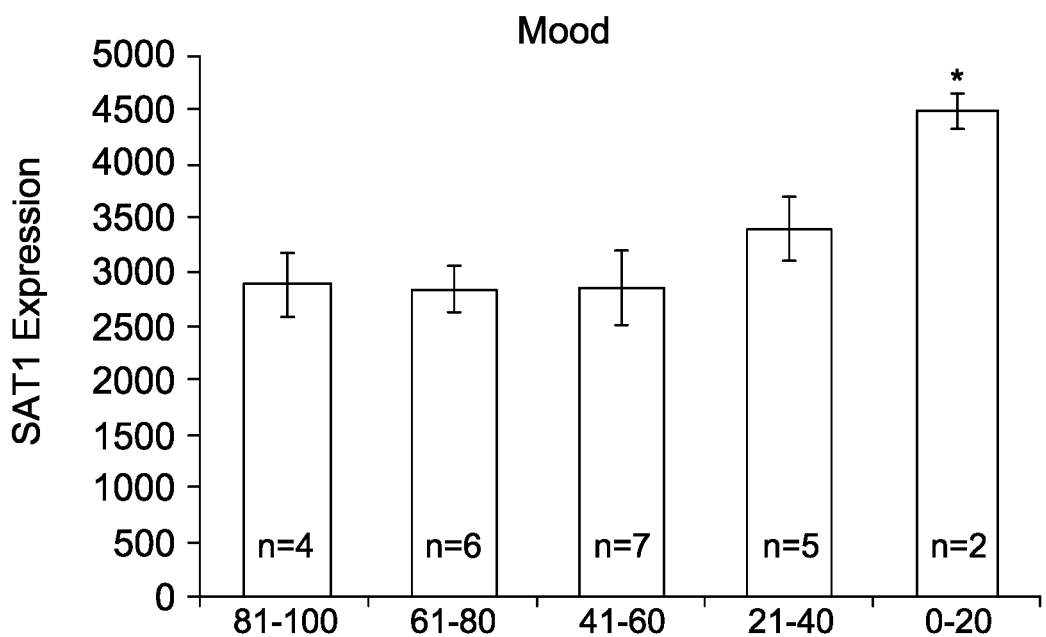
Figure 4C:
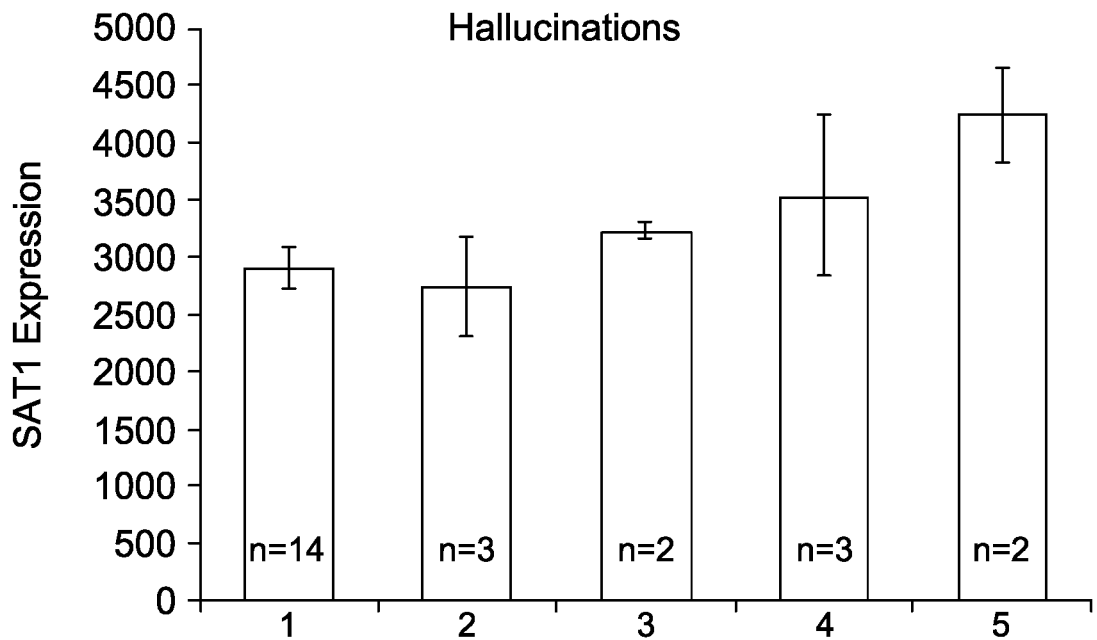
Figure 4D:
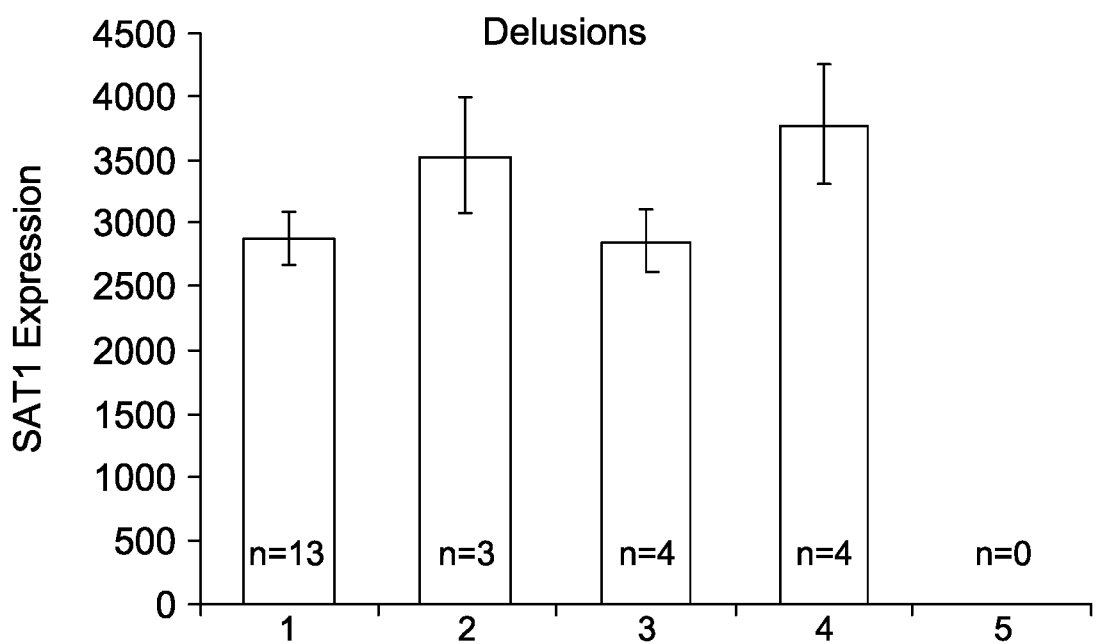
Figure 4E:
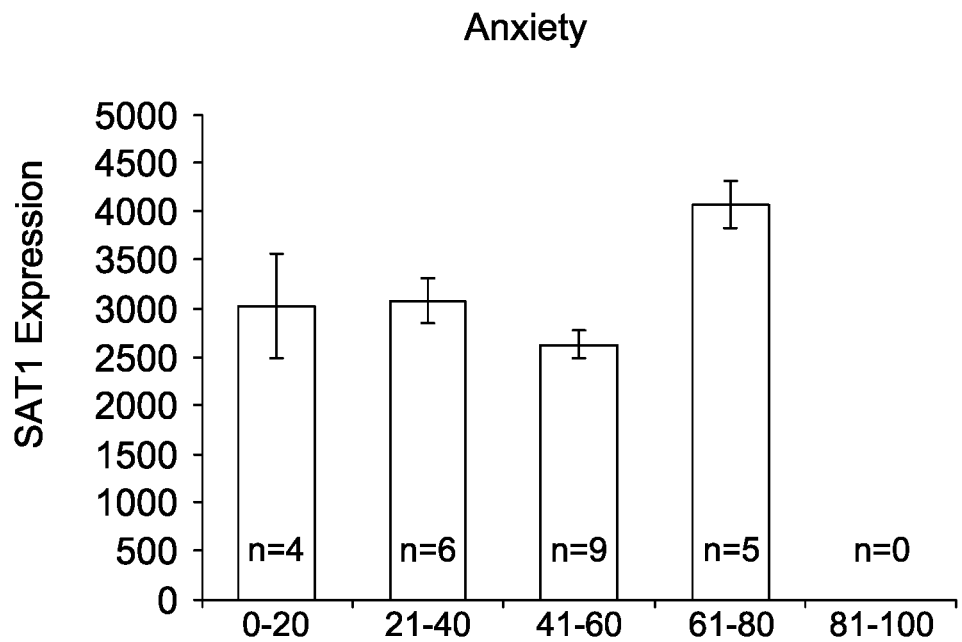
Figure 4F:
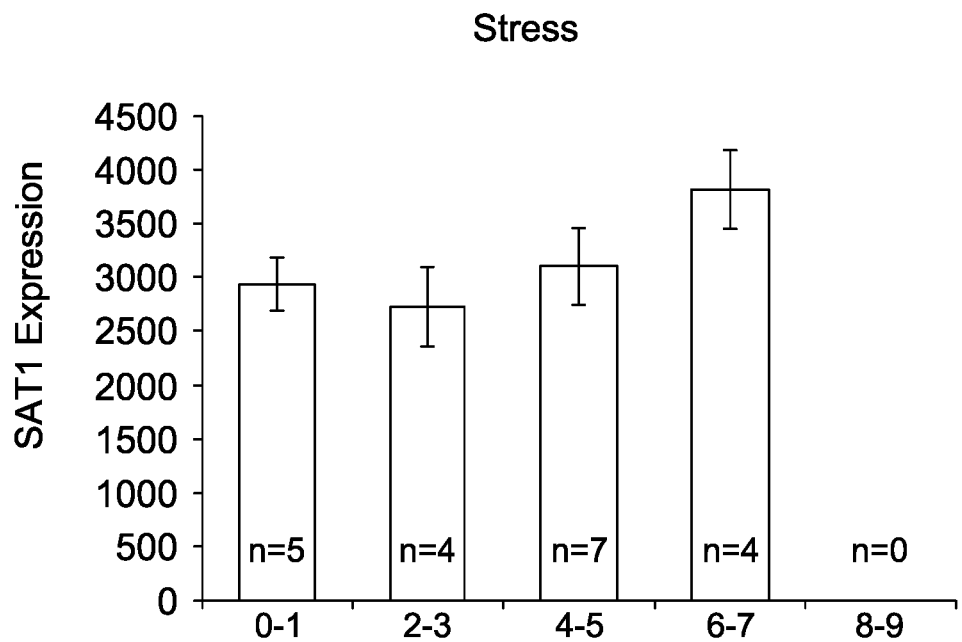
Figures 5D, 5E:
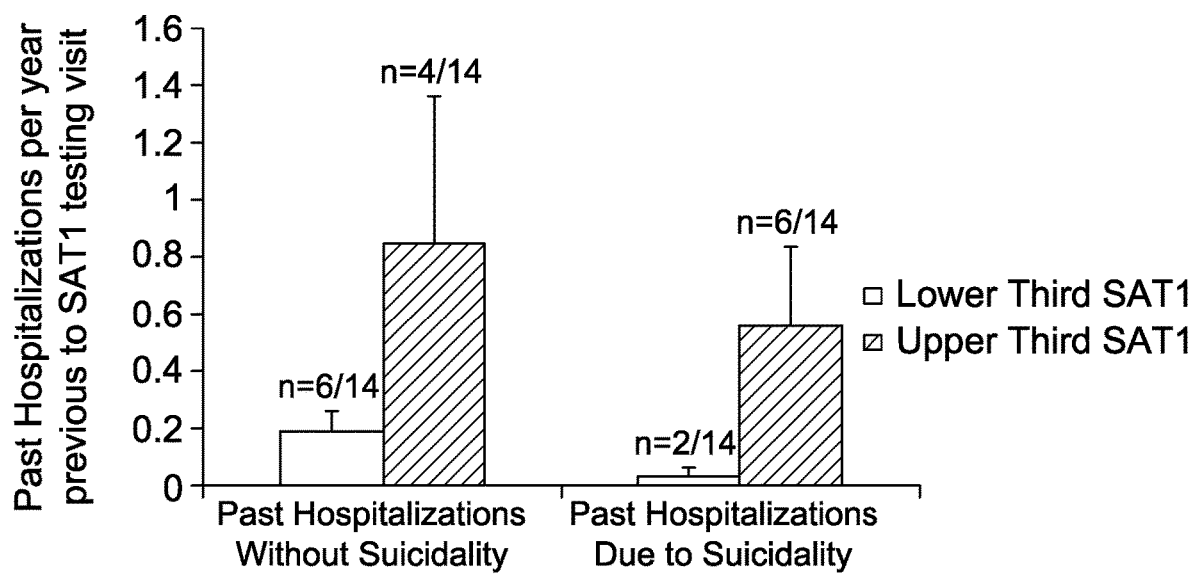
Figures 6D, 6E:
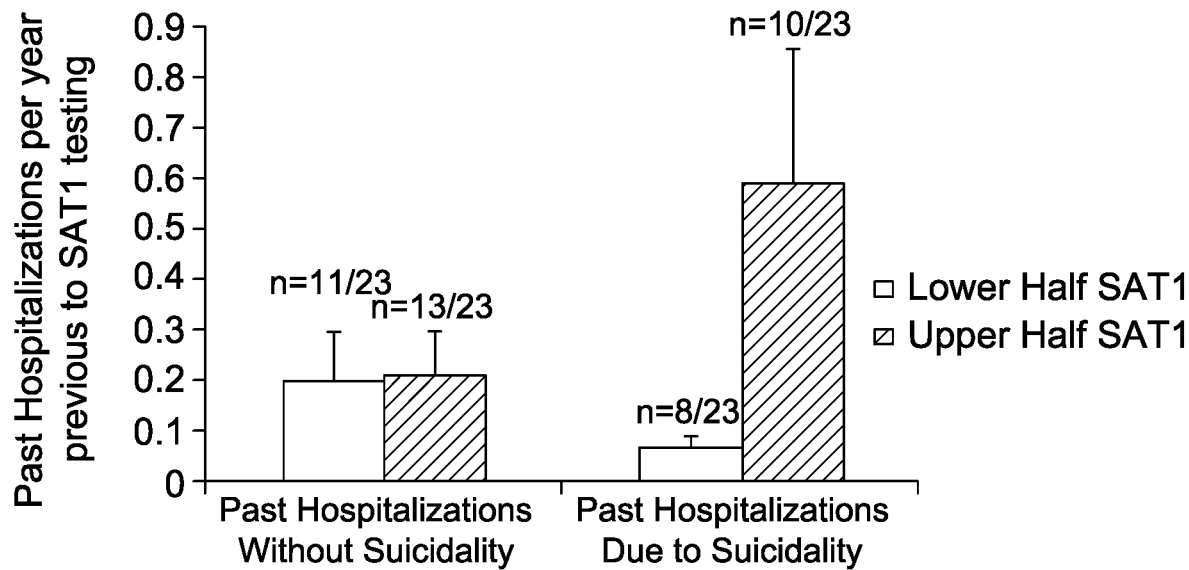

Further, testing of the top candidate biomarkers for suicidality were conduct (see FIGS. 3H and 3I). As shown, thirteen of the 41 CFG-top scoring biomarkers from Table 5 below showed step-wise significant change from no suicide ideation to high suicide ideation, to the validation suicide completers group. Six of them (15%) remained significant after strict Bonferroni correction for multiple comparisons. The top CFG scoring biomarker, SAT1, remained the top biomarker after validation.

Results

Whole-genome gene expression profiling in blood samples from a longitudinally-followed homogeneous cohort of male subjects with a major mood disorder (bipolar disorder) that predisposes to suicidality was conducted. The samples were collected at repeated visits, 3 to 6 months apart. State information about suicidal ideation was collected from a questionnaire administered at the time of each blood draw. An intra-subject design was used to analyze data from 9 subjects that switched from no suicidal ideation to high suicidal ideation at different visits, which factors out genetic variability, as well as some medications, lifestyle and demographic variability. An inter-subject case-case analysis was also used to identify genes differentially expressed in the blood in no suicidal ideation states versus high suicidal ideation states. The top 0.1% and 5% of the gene expression probe sets distributions were considered and differentially scored. Overlap between the intra-subject and inter-subject analyses of gene expression changes was required. Such a restrictive approach was used as a way of minimizing false positives, even at the risk of having false negatives. For example, there were genes on each of the two lists, from intra- and inter-subject analyses, that had clear prior evidence for involvement in suicidality, such as MT1E (Sequeira A. et al., Gene expression changes in the prefrontal cortex, anterior cingulate cortex and nucleus accumbens of mood disorders subjects that committed suicide, PloS one 7, e35367, doi:10,1371/journal.pone.0035367 (2012)), respectively GSK3B (Karege F. et al., Alteration in kinase activity but not in protein levels of protein kinase B and glycogen synthase kinase-3beta in ventral prefrontal cortex of depressed suicide victims. Biol Psychiatry 61, 240-245, doi:10.1016/j.biopsych.2006.04.036 (2007)), but were not included in the subsequent analyses because they were not in the overlap.

A CFG approach was then used to cross-match the list of 246 overlapping top differentially expressed genes from the blood samples with other key lines of evidence (human postmortem brain data, human genetic data) implicating them in suicidality, as a way of identifying and prioritizing disease-relevant genomic biomarkers, extracting generalizable signal out of potential cohort-specific residual noise and genetic heterogeneity. Manually curated databases of the psychiatric genomic and proteomic literature to date was created and used in the CFG analyses. The CFG approach was thus a de facto field-wide collaboration. In essence, in a Bayesian fashion, the whole body of knowledge in the field was used to leverage findings from the Discovery Cohort data sets. Unlike the use of CFG in previous studies, no human peripheral tissue evidence from the literature was used as there was none directly matching the instant genes, reflecting perhaps the dearth of peripheral gene expression work done so far on suicides, and the need for a study like the instant Example. Animal model evidence was also not used as there were to date no clear studies in animal models of self-harm or suicidality. SAT1 (spermidine/spermine N1-acetyltransferase 1) was the top blood biomarker increased in suicidal states (i.e. the top risk marker), and CD24 (CD24 molecule; small cell lung carcinoma cluster 4 antigen) was the top blood biomarker decreased in suicidal states (i.e. the top protective marker) (FIG. 2 and Table 5).

TABLE 5

Top gene expression biomarkers for suicidality

| Gene Symbol/ Gene name | Probe-sets | Change (I = Increase) (D = Decrease) | Differential Expression Score | Prior Human Genetic Evidence | Prior Human Brain Expression Evidence | Total CFG Score |
|---|---|---|---|---|---|---|
| SAT1 spermidine/spermine N1-acetyltransferase 1 | 203455_s_at | I | 2 | (Assoc) Suicide attempt (Fiori. Wanner et al. 2010). Suicide (Sequeira, Gwadry et al. 2006) | Suicide in Depression (D) PFC (Chen. Fiori et al., 2010) Suicide(D) AMY, PFC, HIP, THAL (Fiori, Bureau et al. 2011) Suicide(D) PFC (Flori and Turacki 2011) Suicide (D) PFC (Fiori, Mechawar et al. 2009) Suicide (D) PFC (Fiori, Zouk et al. 2011) Suicide(D) PFC (Guipponi, Deutsch et al. 2009) Suicide(D)PFC (Klempan, T. A. et al 2009) Suicide(D)PFC (Sequeira, A. et al. 2006) | 8 |
| CD24 CD24 molecule | 209772_s_at | D | 4 | | Suicide in mood disorder)(D)NAC (Sequeira A. et al. 2012) | 8 |
| FOXN3 forkhead box N3 | 230790_x_at | I | 2 | (Assoc) Suicide (Galfalvy, H. et al. 2011) | Suicide (I) PFC (Galfalvy, H. et al. 2011) | 8 |
| GBP1 guanylate binding protein 1, interferon-inducible, 67 kDa | 231577_x_at 202269_x_at 202270_at | I | 4 2 2 | | Suicide in mood disorders (D) NAC (Karege, F. et al. 2007). | 8 6 6 |
| PIK3R5 Phosphoinositide-3-kinase, regulatory subunit5 | 227553_at | I | 4 | | Suicide in mood disorder (D) PFC (Seqeira, Morgan et al. 2012) | 8 |
| APOL2 Apolipoprotein L2 | 221653_x_at | I | 2 | | Suicide PFC (I) (Kekesi, K. A. et al. 2012) | 6 |
| ATP13A2 ATPase type 13A2 | 218608_at | D | 2 | | Suicide(D) (Sequeira, A. et al. 2012) | 6 |
| ATP6V0E1 ATPase, H+ transporting, lysosomal 9 kDa, V0 subunit e1 | 214149_s_at 214244_s_at | I | 2 | | Suicide(D)PFC (Sequeira A. et al. 2006) | 6 |
| EPHX1 epoxide hydrolase 1, microsomal (xenobiotic) | 202017_at | D | 2 | | Suicide in Schizophrenia (D) PFC (Kim, Choi et al. 2007) | 6 |
| GCOM1 GRINL1A complex locus | 239099_at | I | 2 | | Suicide in Depression (D) Klempan T A, 2009 | 6 |
| HTRA1 HtrA serine peptidase 1 | 201185_at | D | 2 | | Suicide(I) (Sequeria, A. et al. 2012) | 6 |

TABLE 5-continued

Top gene expression biomarkers for suicidality

| Gene Symbol/ Gene name | Probe-sets | Change (I = Increase) (D = Decrease) | Differential Expression Score | Prior Human Genetic Evidence | Prior Human Brain Expression Evidence | Total CFG Score |
|---|---|---|---|---|---|---|
| IL1B interleukin 1, beta | 39402_at | I | 2 | | Suicide(I) PFC (Pandey, G. N. et al., 2012) | 6 |
| LEPR leptin receptor | 211354_s_at | D | 2 | | Suicide(D) PFC (Klempan, T. A. et al. 2009) Suicide(D) PFC (Lalovic, Klempen et al. 2010) Suicide(D) HIP (Sequeria, A. et al. 2007) Suicide in Depression (I) PFC (Zhurov V. et al. 2012) | 6 |
| LHFP lipoma HMGIC fusion partner | 218656_s_at | I | 2 | | Suicide in mood disorder (I) NAC (Sequeria, A. et al. 2012) | 6 |
| LIPA lipase A | 236156_at | I | 2 | | Violent Suicide (I) PFC (Freemantle, E et al. 2013) | 6 |
| MARCKS myristoylated alanine-rich protein kinase C substrate | 213002_at | I | 2 | | Suicide in Depression (I) (Pandey, G. N. et al. 2003) | 6 |
| PGLS 6-Phosphogluconolactonase | 230699_at | I | 2 | | Suicide PFC (D) (Kekesi K. A. et al. 2012) | 6 |
| PTEN phosphatase and tensin homolog | 222176_at | I | 2 | | Suicide PFC, HIP (I) (Dwivedi Y. et al. 2010) | 6 |
| RECK reversion-inducing-cysteine-rich protein with kazal motifs | 216153_x_at | I | 2 | | Suicide (I) PFC (Sequeira A. et al. 2012) | 6 |
| SPTBN1 spectrin, beta, non-erythrocytic 1 | 200671_s_at | D | 2 | | Suicide in mood disorders (I) NAC (Sequeira A. et al. 2012) | 6 |
| TNFSF10 tumor necrosis factor (ligand) superfamily, member 10 | 202688_at 202687_s_at 214329_x_at | I | 2 | | Suicide in Schizophrenia (I)PFC (Kim, S. et al. 2007) Suicide in Depression (I) PFC (Zhurov V. et al. 2012) | 6 |
| ABCA1 ATP-binding cassette, sub-family A (ABC1), member 1 | 203504_s_at | I | 4 | | | 4 |
| ARHGEF40 (FLJ10357) Rho guanine nucleotide exchange factor (GEF) 40 | 241631_at | I | 4 | | | 4 |
| CASC1 cancer susceptibility candidate 1 | 220168_at | I | 4 | | | 4 |
| DHRS9 dehydrogenase/reductase (SDR family) member 9 | 219799_s_at | I | 4 | | | 4 |
| DISC1 disrupted in schizophrenia 1 | 244642_at | I | 2 | (Assoc) Suicide (Galfalvy H. et al. 2011) | | 4 |

TABLE 5-continued

Top gene expression biomarkers for suicidality

| Gene Symbol/ Gene name | Probe-sets | Change (I = Increase) (D = Decrease) | Differential Expression Score | Prior Human Genetic Evidence | Prior Human Brain Expression Evidence | Total CFG Score |
|---|---|---|---|---|---|---|
| EIF2AK2 eukaryotic translation initiation factor 2-alpha kinase 2 | 204211_x_at | I | 4 | | | 4 |
| LOC727820 uncharacterized LOC727820 | 231247_s_at LOC727820 | I | 4 | | | 4 |
| MAP3K3 mitogen-activated protein kinase kinase kinase 3 | 242117_at | I | 4 | | | 4 |
| MBNL2 muscleblind-like 2 (*Drosophila*) | 205017_s_at | D | 2 | (Assoc) Suicide (Galfalvy H. et al. 2011) | | 4 |
| MT-ND6 (ND6) mitochondrially encoded NADH dehydrogenase 6 | 1553575_at | I | 4 | | | 4 |
| OR2J3 olfactory receptor, family 2, subfamily J, member 3 | 217334_at | D | 4 | | | 4 |
| RBM47 RNA binding motif protein 47 | 1565597_at | I | 4 | | | 4 |
| RHEB Ras homolog enriched in brain | 227633_at | D | 2 | (Assoc) Suicide (Menke A. et al. 2012) | | 4 |
| RICTOR RPTOR independent companion of MTOR, complex 2 | 228248_at | I | 4 | | | 4 |
| SAMD9L sterile alpha motif domain containing 9-like | 243271_at; 230036_at | I | 4 | | | 4 |

In order to validate the Discovery Cohort findings in the most stringent way possible, SAT1 levels in blood samples from the Validation Cohort of 9 consecutive male suicide completers obtained from the coroner's office were evaluated. SAT1 gene expression levels were found to be elevated in 9 out of 9 (100%) subjects who committed suicide. In each suicide completer, the increase in SAT1 was at least three standard deviations above the average levels in high suicidal ideation subjects. The results were further strengthened by using a panel of the two markers (SAT1 and CD24) (FIGS. 3A-C). As shown in FIGS. 3A-3C, risk marker SAT1 expression was significantly increased (p=0.0057) between subjects with high suicidal ideation (SI) (mean=3413.37) and those reporting no suicidal ideation (mean=2642.97). In the Validation Cohort of suicide completers (mean=7171.51), a significantly greater expression of SAT1 was found as compared to both high suicide ideation (p=7.27e-07) and no suicide ideation (p=1.51e-07) groups from the Discovery Cohort (FIG. 3A). Further, suicide risk score was calculated by scoring the standard deviation band a subject fell within as derived from the high suicide ideation Discovery Cohort, starting from the mean of the high suicide ideation Discovery Cohort (FIG. 3B). 0 indicates the subject fell between the means of the high and low suicide ideation subjects in the Discovery Cohort. A score of 1 means between the mean of the high suicide ideation and the first standard deviation above it, score of 2 between the first and second standard deviation, score of 3 between the second and third standard deviation, and so on.

As shown in FIGS. 3D-3F, protective marker CD 24 expression was significantly decreased (p=0.0044) within the Discovery Cohort between subjects reporting high suicide ideation (mean=73.01) and no suicide ideation (mean=108.634). The Validation Cohort of suicide completers (mean=71.61) was also significantly decreased (p=0.0031) when compared to subjects reporting no suicide ideation (FIG. 3D). Suicide risk score was defined as the standard deviation band in which the subject expression fell below the mean of the high suicide ideation Discovery Cohort (FIG. 3E).

FIG. 3G shows the sum of standard deviation suicide risk scores for both biomarkers (SAT1 and CD24) in the Validation Cohort (i.e., suicide completers).

One of the other biomarkers identified to be decreased in high suicidal states in the current Example was the circadian clock gene DBP (D-box binding protein). Serendipitously, previous work showed that mice engineered to lack DBP were stress-reactive and displayed a behavioral phenotype similar to bipolar disorder and co-morbid alcoholism (Le-Niculescu H. et al., "Phenomic, convergent functional genomic, and biomarker studies in a stress-reactive genetic animal model of bipolar disorder and co-morbid alcoholism," American Journal of Medical Genetics, Part B, Neuropsychiatric genetics: the official publication of the International Society of Psychiatric Genetics 147B, 134-166, doi:10.1002/ajmg.b.30707 (2008)). In addition to bipolar disorder, alcoholism is known to increase the risk for suicide. Treatment with omega-3 fatty acids normalized the phenotype of those mice. Low omega-3 levels have been previously correlated with increased suicidality in human epidemiological studies (see Sublette M. et al., "Omega-3 polyunsaturated essential fatty acid status as a predictor of future suicide risk," Am J Psychiatry 163, 1100-1102, doi: 10.1176/appi.ajp.163.6.110 (2006); Lewis M. D. et al., "Suicide deaths of active-duty US military and omega-3 fatty-acid status: a case-control comparison," J Clin Psychiatry 72, 1585-1590, doi:10.4088/JCP.11m06879 (2011)). Pathway analyses of the instant suicidality biomarker data identified among the top pathways the omega-3 docosahexaenoic acid (DHA) signaling pathway. Several of the biomarkers from this Example (those bolded in Table 6 in "Modulated by DHA" column)) were changed in expression by omega-3 treatment in the blood of the DBP mouse model in opposite direction to our human suicidality data (Table 6). PTEN, a biomarker increased in suicidality in the current Example in the blood, as well as in the brain of suicide completers, was also increased in the amygdala and decreased in the prefrontal cortex of DBP knock-out mice subjected to stress.

TABLE 6

Genes in our dataset modulated by Clozapine and Omega-3 Fatty Acids (DHA).

| Gene Symbol | Gene Name | Direction of Change | CFG score | Modulated by Clozapine | Modulated by DHA |
|---|---|---|---|---|---|
| SAT1 | spermidine/spermine N1-acetyl transferase 1 | I | 8 | | (D) Blood |
| GBP1 | guanylate nucleotide binding protein 1 | I | 8 | | (D) Blood |
| ATP13A2 | ATPase type 13A2 | D | 6 | (D) VT | |
| EPHX1 | epoxide hydrolase 1, microsomal | D | 6 | (D) VT | |
| IL1B | interleukin 1 beta | I | 6 | (I) Blood | (D) Blood |
| LHFP | lipoma HMGIC fusion partner | I | 6 | (I) Blood, VT | (D) Blood |
| MARCKS | myristoylated alanine rich protein kinase C substrate | I | 6 | | (I) HIP |
| PTEN | phosphatase and tensin homolog | I | 6 | (I) VT | |
| SPTBN1 | spectrin, beta, non-erythrocytic 1 | D | 6 | (I) Blood, VT | (D) Blood |
| ABCA1 | ATP-binding cassette, sub-family A (ABC1), member 1 | I | 4 | (I) VT | |
| MAP3K3 | mitogen-activated protein kinase kinase kinase 3 | I | 4 | | (D) Blood |
| MBNL2 | muscleblind-like 2 | D | 4 | (I) Blood | (D) Blood |
| ATG3 | autophagy-related 3 (yeast) | I | 2 | | (D) Blood |
| ATXN2 | ataxin 2 | I | 2 | (I) VT | |
| CCR1 | chemokine (C-C motif) receptor 1 | I | 2 | | (D) Blood |
| CCRN4L | CCR4 carbon catabolite repression 4-like | I | 2 | | (I) Blood |
| CD84 | CD84 antigen | D | 2 | (I) Blood | (D) Blood |
| CEACAM1 | CEA-related cell adhesion molecule 1 | I | 2 | | (D) Blood |
| CELA1 | chymotrypsin-like elastase family, member 1 | D | 2 | | (D) Blood |
| CLEC4E | C-type lectin domain family 4, member e | I | 2 | | (D) Blood |
| CLEC7A | C-type lectin domain family 7, member a | I | 2 | | (D) Blood |
| CORO1C | coronin, actin binding protein 1C | I | 2 | (D) VT | |
| DLGAP1 | discs, large (*Drosophila*) homolog-associated protein 1 | I | 2 | (I) VT | |
| DOCK1 | dedicator of cytokinesis 1 | D | 2 | (D) VT | |
| DOCK4 | dedicator of cytokinesis 4 | I | 2 | (D) HIP | |
| FABP3 | fatty acid binding protein 3, muscle and heart | I | 2 | (I) VT | |
| FNIP1 | folliculin interacting protein 1 | I | 2 | (I) VT | |
| FOXK2 | forkhead box K2 | D | 2 | (I) VT | |
| FZR1 | fizzy/cell division cycle 20 related 1 (Drosophila) | D | 2 | | (I) Blood |
| GBP2 | guanylate nucleotide binding protein 2 | I | 2 | (D) VT | |
| GREM1 | gremlin 1 | I | 2 | | (D) HIP |
| IFIT2 | interferon-induced protein with tetratricopeptide repeats 2 | I | 2 | (I) Blood | (D) Blood |
| IFIT3 | interferon-induced protein with tetratricopeptide repeats 3 | I | 2 | | (D) NAC |
| IL1RAP | interleukin 1 receptor accessory protein | I | 2 | (I) VT | |

TABLE 6-continued

Genes in our dataset modulated by Clozapine and Omega-3 Fatty Acids (DHA).

| Gene Symbol | Gene Name | Direction of Change | CFG score | Modulated by Clozapine | Modulated by DHA |
|---|---|---|---|---|---|
| KLHDC3 | kelch domain containing 3 | D | 2 | (I) VT | |
| KPNA3 | karyopherin (importin) alpha 3 | I | 2 | (D) VT | |
| LARP4 | La ribonucleoprotein domain family, member 4 | D | 2 | (I) VT | |
| LONRF1 | LON peptidase N-terminal domain and ring finger 1 | I | 2 | (I) VT | |
| MCTP1 | multiple C2 domains, transmembrane 1 | I | 2 | | (I) HIP |
| MDM4 | transformed mouse 3T3 cell double minute 4 | I | 2 | | (D) Blood |
| NUB1 | negative regulator of ubiquitin-like proteins 1 | I | 2 | (D) VT | |
| NUDT3 | nudix (nucleotide diphosphate linked moiety X)-type motif 3 | I | 2 | | (D) Blood |
| OGT | O-linked N-acetylglucosamine (GlcNAc) transferase | I | 2 | (I) Blood | (D) HIP; (I) NAC |
| PELI1 | pellino 1 | I | 2 | (I) AMY | (I) HIP |
| PKN2 | protein kinase N2 | I | 2 | | (I) Blood |
| R3HDM1 | R3H domain 1 (binds single-stranded nucleic acids) | I | 2 | (I) VT | (D) Blood |
| RAI14 | retinoic acid induced 14 | D | 2 | | (I) HIP |
| RASSF3 | Ras association (RaIGDS/AF-6) domain family member 3 | I | 2 | (I) VT | (D) Blood |
| RPL37A | ribosomal protein L37a | I | 2 | | (I) Blood |
| RPLP2 | ribosomal protein, large P2 | I | 2 | | (I) Blood |
| RSAD2 | radical S-adenosyl methionine domain containing 2 | I | 2 | (I) Blood | (I) Blood |
| S100A8 | S100 calcium binding protein A8 (calgranulin A) | I | 2 | (D) Blood | (D) Blood |
| SFRP2 | secreted frizzled-related protein 2 | D | 2 | (D) VT | |
| SLC25A37 | solute carrier family 25, member 37 | I | 2 | (I) VT | (I) Blood |
| SLC2A13 | solute carrier family 2 (facilitated glucose transporter), member 13 | I | 2 | (I) VT | |
| SPOCK2 | sparc/osteonectin, cwcv and kazal-like domains proteoglycan 2 | D | 2 | (I) VT | |
| TAOK1 | TAO kinase 1 | I | 2 | (I) VT | (D) PFC; (I) HIP |
| TB1X | transducin (beta)-like 1 X-linked | I | 2 | (D) VT | |
| TCEA1 | transcription elongation factor A (SII) 1 | I | 2 | (D) VT | (I) Blood |
| TMEM140 | transmembrane protein 140 | I | 2 | (I) Blood | (D) Blood |
| TMEM154 | transmembrane protein 154 | I | 2 | | (D) Blood |
| TNFAIP6 | tumor necrosis factor alpha induced protein 6 | I | 2 | (I) AMY | |
| TNK2 | tyrosine kinase, non-receptor, 2 | D | 2 | (D) VT | |
| TOP1 | topoisomerase (DNA) I | I | 2 | (I) VT | (I) Blood |
| TRIP12 | thyroid hormone receptor interactor 12 | I | 2 | (I) VT | |
| TRPM7 | transient receptor potential cation channel, subfamily M, member 7 | I | 2 | | (D) AMY |
| UBE2B | ubiquitin-conjugating enzyme E2B, RAD6 homology (S. cerevisiae) | I | 2 | (I) Blood, AMY, PFC | (I) Blood |
| WDR77 | WD repeat domain 77 | D | 2 | (D) VT | |

Bold are genes that are changed in opposite direction to suicidal ideation by one or both of the treatments.

Other circadian clock-modulated genes identified as biomarkers for suicidality were PIK3R5, MARCKS, IL1B, CASC1, CCRN4L, H3F3B, RBCK1, TNK2, and UBE2B. Additionally, biomarkers, as bolded in Table 6 in the "Modulated by Clozapine" column, provided evidence for modulation by clozapine in blood in opposite direction to the human suicidality data in previous independent animal model pharmacogenomics studies (Table 6). Clozapine is the only FDA approved treatment for suicidality. Thus, the convergent evidence for the instant biomarkers is strong in translational ways beyond those used for their discovery and selection. S100A8 may be a key biomarker to monitor in terms of response to treatment with classic (clozapine) and complementary (omega-3) agents. Other potential drugs to be studied for modulating suicidality were revealed by the above analyses (Tables 4 and 6).

SAT1, FOXN3, DISC1, MBNL2 and RHEB had genetic association evidence for suicidality, suggesting that they are not only state biomarkers but also trait factors influencing suicidal risk. DISC1 is also one of the top candidate genes for schizophrenia based on a large scale CFG analysis of schizophrenia GWAS recently conducted (Ayalew M. et al., "Convergent functional genomics of schizophrenia: from comprehensive understanding to genetic risk prediction," Molecular Psychiatry 17, 887-905, doi:10.1038/mp.2012.37 (2012)), while DISC1 and MBNL2 are also among the top candidate genes for bipolar disorder based on a large scale CFG analysis of bipolar disorder GWAS (Patel S. D. et al., "Coming to grips with complex disorders: genetic risk prediction in bipolar disorder using panels of genes identified through convergence functional genomics," American Journal of Medical Genetics Part b, Neuropsychiatric genetics: the official publication of the International Society of Psychiatric genetics 153B, 850-877, doi:10.1pp2/ajmg.b.31087 (2010)). Additionally, DISC1 has clear animal model data for the role of its interaction with environmental stress in the pathophysiology of psychotic depression. DISC1 and MBNL2 may thus be key state and trait factors for suicidality risk in psychotic mood disorder subjects, and an indication for clozapine treatment in such subjects.

Suicide biomarkers that were identified in this study were overlapped with biomarkers identified as mood biomarkers (Le-Niculescu H. et al., "Identifying blood biomarkers for mood disorders using convergent functional genomics," Molecular Psychiatry 14, 156-174, doi:10.1111/ele.12064 (2009)) and psychosis biomarkers (Kurian S. M. et al., "Identification of blood biomarkers for psychosis using convergent functional genomics," Molecular Psychiatry 16, 37-58, doi:10.1038/mp.2009.117 (2011)) (Table 7). DOCK5 and 4 other biomarkers (as bolded in Table 7 in the "Direction of change in Mood" column were changed in high suicidal states in opposite direction to their change in high mood states, and DOCK5 and 6 other biomarkers (as bolded in Table 7 in the "Direction of change in Hallucination" or "Direction of change in Delusions" columns) were changed in the same direction as their change in high psychosis states, suggesting that suicidality can indeed be viewed as a psychotic depressed state, and that DOCK5 may be an additional key biomarker reflecting that state.

TABLE 7

Genes with evidence as mood and/or psychosis blood biomarkers.

| Gene Symbol | Gene Name | CFG score in SI | Direction of change in SI | Direction of change in Mood | Direction of change in Hallucination | Direction of change in Delusions |
|---|---|---|---|---|---|---|
| LEPR | leptin receptor | 6 | D | (I) | | |
| CD84 | CD84 molecule | 2 | D | | | (I) |
| DOCK5 | dedicator of cytokinesis 5 | 2 | I | (D) | (I) | |
| EPM2A | epilepsy, progressive myoclonus type 2A, Lafora disease (laforin) | 2 | D | | | (D) |
| ERICH1 | glutamate-rich 1 | 2 | I | | (D) | (D) |
| FKBP7 | FK506 binding protein 7 | 2 | D | | | (D) |
| IDH1 | isocitrate dehydrogenase 1 (NADP+), soluble | 2 | I | | | (D) |
| KIAA0494 | KIAA0494 | 2 | I | (D) | | |
| LARP4 | La ribonucleoprotein domain family, member 4 | 2 | D | (D) | | |
| MXD1 | MAX dimerization protein 1 | 2 | I | | | (I) |
| PID1 | phosphotyrosine interaction domain containing 1 | 2 | D | | | (D) |
| PML | promyelocytic leukemia | 2 | I | | | (I) |
| PPP2R1B | protein phosphatase 2, regulatory subunit A, beta | 2 | D | | | (D) |
| SLC2A13 | solute carrier family 2 (facilitated glucose transporter), member 13 | 2 | I | (D) | | |

TABLE 7-continued

Genes with evidence as mood and/or psychosis blood biomarkers.

| Gene Symbol | Gene Name | CFG score in SI | Direction of change in SI | Direction of change in Mood | Direction of change in Hallucination | Direction of change in Delusions |
|---|---|---|---|---|---|---|
| TRIM6 | tripartite motif containing 6 | 2 | I | (D) | | |
| TRPM7 | transient receptor potential cation channel, subfamily M, member 7 | 2 | I | (I) | | |

Discussion

This Example shows overlap at a gene and pathway level with cancer and apoptosis (Table 3, Table 8). SAT1, for example, is a key catabolic enzyme for polyamines Polyamine levels within cells control cell viability, and significant decreases in polyamine levels can result in apoptosis. They appear to reflect an endowment for cellular and organismal activity and growth, key characteristics of mood. SAT1, which increased in suicidal subjects of this Example, is highly inducible by a variety of stimuli, including toxins, cytokines, heat shock, ischemia, and other stresses.

TABLE 8

Complete list of genes differentially expressed in the discovery cohort overlapping between the intra-subject and inter-subject analyses (n = 246).

| Probe set ID | Gene Symbol | Gene Name | Change | Total CFG Score | Evidence or possible roles in apoptosis |
|---|---|---|---|---|---|
| 203455_s_at | SAT1 | spermidine/spermine N1-acetyltransferase 1 | I | 8 | yes |
| 209772_s_at | CD24 | CD24 molecule | D | 8 | yes |
| 230790_x_at | FOXN3 | forkhead box N3 | I | 8 | |
| 231577_s_at; 202269_x_at; 202270_at | GBP1 | guanylate binding protein 1, interferon-inducible | I | 8 | yes |
| 227553_at | PIK3R5 | phosphoinositide-3-kinase, regulatory subunit 5 | I | 8 | |
| 221653_x_at | APOL2 | apolipoprotein L, 2 | I | 6 | |
| 218608_at | ATP13A2 | ATPase type 13A2 | D | 6 | |
| 214149_s_at | ATP6V0E1 | ATPase, H+ transporting, lysosomal 9 kDa, V0 subunit e1 | I | 6 | |
| 202017_at | EPHX1 | epoxide hydrolase 1, microsomal (xenobiotic) | D | 6 | yes |
| 239099_at | GCOM1 | GRINL1A complex locus 1 | I | 6 | |
| 201185_at | HTRA1 | HtrA serine peptidase 1 | D | 6 | yes |
| 39402_at | IL1B | interleukin 1, beta | I | 6 | yes |
| 211354_s_at | LEPR | leptin receptor | D | 6 | yes |
| 218656_s_at | LHFP | lipoma HMGIC fusion partner | I | 6 | |
| 236156_at | LIPA | lipase A, lysosomal acid, cholesterol esterase | I | 6 | |
| 213002_at | MARCKS | myristoylated alanine-rich protein kinase C substrate | I | 6 | yes |
| 230699_at | PGLS | 6-phosphogluconolactonase | I | 6 | |
| 222176_at | PTEN | phosphatase and tensin homolog | I | 6 | yes |
| 216153_x_at | RECK | reversion-inducing-cysteine-rich protein with kazal motifs | I | 6 | yes |
| 200671_s_at | SPTBN1 | spectrin, beta, non-erythrocytic 1 | D | 6 | yes |
| 202688_at | TNFSF10 | tumor necrosis factor (ligand) superfamily, member 10 | I | 6 | yes |
| 203504_s_at; 203505_at | ABCA1 | ATP-binding cassette, sub-family A (ABC1), member 1 | I | 4 | |
| 241631_at | ARHGEF40 | Rho guanine nucleotide exchange factor (GEF) 40 | I | 4 | |
| 220168_at | CASC1 | cancer susceptibility candidate 1 | I | 4 | |
| 219799_s_at | DHRS9 | dehydrogenase/reductase (SDR family) member 9 | I | 4 | |
| 244642_at | DISC1 | disrupted in schizophrenia 1 | I | 4 | |
| 204211_x_at | EIF2AK2 | eukaryotic translation initiation factor 2-alpha kinase 2 | I | 4 | yes |
| 231247_s_at | LOC727820 | uncharacterized LOC727820 | I | 4 | |
| 242117_at | MAP3K3 | mitogen-activated protein kinase kinase kinase 3 | I | 4 | yes |
| 205017_s_at | MBNL2 | muscleblind-like splicing regulator 2 | D | 4 | |
| 1553575_at | MT-ND6 | mitochondrially encoded NADH dehydrogenase 6 | I | 4 | |

TABLE 8-continued

Complete list of genes differentially expressed in the discovery cohort overlapping between the intra-subject and inter-subject analyses (n = 246).

| Probe set ID | Gene Symbol | Gene Name | Change | Total CFG Score | Evidence or possible roles in apoptosis |
|---|---|---|---|---|---|
| 217334_at | OR2J3 | olfactory receptor, family 2, subfamily J, member 3 | D | 4 | |
| 1565597_at | RBM47 | RNA binding motif protein 47 | I | 4 | |
| 227633_at | RHEB | Ras homolog enriched in brain | D | 4 | yes |
| 228248_at | RICTOR | RPTOR independent companion of MTOR, complex 2 | I | 4 | |
| 243271_at; 230036_at | SAMD9L | sterile alpha motif domain containing 9-like | I | 4 | |
| 206995_x_at | SCARF1 | scavenger receptor class F, member 1 | I | 4 | |
| 213119_at | SLC36A1 | solute carrier family 36 (proton/amino acid symporter), member 1 | I | 4 | |
| 232375_at | STAT1 | signal transducer and activator of transcription 1, 91 kDa | I | 4 | yes |
| 236879_at | UBA6 | ubiquitin-like modifier activating enzyme 6 | I | 4 | |
| 1563075_s_at | ZC3HAV1 | zinc finger CCCH-type, antiviral 1 | I | 4 | |
| 213736_at | COX5B | cytochrome c oxidase subunit Vb | I | 3 | |
| 203874_s_at | SMARCA1 | SWI/SNF related, matrix associated, actin dependent regulator of chromatin, subfamily a, member 1 | I | 3 | |
| 229577_at | AGPAT6 | 1-acylglycerol-3-phosphate O-acyltransferase 6 (lysophosphatidic acid acyltransferase, zeta) | D | 2 | |
| 206513_at | AIM2 | absent in melanoma 2 | I | 2 | yes |
| 227438_at | ALPK1 | alpha-kinase 1 | I | 2 | |
| 210873_x_at | APOBEC3A | apolipoprotein B mRNA editing enzyme, catalytic polypeptide-like 3A | I | 2 | |
| 239002_at | ASPM | asp (abnormal spindle) homolog, microcephaly associated (Drosophila) | D | 2 | |
| 222840_at | ATG2B | autophagy related 2B | D | 2 | |
| 220237_at | ATG3 | autophagy related 3 | I | 2 | |
| 211852_s_at | ATRN | attractin | D | 2 | |
| 243839_s_at | ATXN2 | ataxin 2 | I | 2 | yes |
| 204516_at | ATXN7 | ataxin 7 | I | 2 | |
| 203140_at; 228758_at | BCL6 | B-cell CLL/lymphoma 6 | I | 2 | yes |
| 219072_at | BCL7C | B-cell CLL/lymphoma 7C | D | 2 | |
| 214068_at | BEAN1 | brain expressed, associated with NEDD4, 1 | D | 2 | |
| 212563_at | BOP1 | block of proliferation 1 | D | 2 | |
| 233809_at | C15orf63 | chromosome 15 open reading frame 63 | I | 2 | yes |
| 221954_at | C20orf111 | chromosome 20 open reading frame 111 | I | 2 | yes |
| 1564276_at | C5orf56 | chromosome 5 open reading frame 56 | I | 2 | |
| 1553329_at | C7orf45 | chromosome 7 open reading frame 45 | I | 2 | |
| 227364_at | CAPZA1 | capping protein (actin filament) muscle Z-line, alpha 1 | I | 2 | yes |
| 213596_at | CASP4 | caspase 4, apoptosis-related cysteine peptidase | I | 2 | yes |
| 207500_at | CASP5 | caspase 5, apoptosis-related cysteine peptidase | I | 2 | yes |
| 205099_s_at | CCR1 | chemokine (C-C motif) receptor 1 | I | 2 | yes |
| 1554283_at | CCRN4L | CCR4 carbon catabolite repression 4-like (S. cerevisiae) | I | 2 | |
| 206485_at | CD5 | CD5 molecule | D | 2 | yes |
| 243931_at | CD58 | CD58 molecule | I | 2 | yes |
| 211189_x_at | CD84 | CD84 molecule | D | 2 | |
| 234255_at | CDC42SE2 | CDC42 small effector 2 | I | 2 | |
| 209498_at | CEACAM1 | carcinoembryonic antigen-related cell adhesion molecule 1 (biliary glycoprotein) | I | 2 | yes |
| 224198_at | CELA1 | chymotrypsin-like elastase family, member 1 | D | 2 | |

TABLE 8-continued

Complete list of genes differentially expressed in the discovery cohort overlapping between the intra-subject and inter-subject analyses (n = 246).

| Probe set ID | Gene Symbol | Gene Name | Change | Total CFG Score | Evidence or possible roles in apoptosis |
|---|---|---|---|---|---|
| 210069_at | CHKB-CPT1B | CHKB-CPT1B readthrough (non-protein coding) | I | 2 | |
| 222174_at | CHURC1-FNTB | CHURC1-FNTB readthrough | D | 2 | |
| 209571_at | CIR1 | corepressor interacting with RBPJ, 1 | I | 2 | |
| 219859_at | CLEC4E | C-type lectin domain family 4, member E | I | 2 | |
| 221698_s_at | CLEC7A | C-type lectin domain family 7, member A | I | 2 | yes |
| 200861_at | CNOT1 | CCR4-NOT transcription complex, subunit 1 | D | 2 | |
| 211141_s_at | CNOT3 | CCR4-NOT transcription complex, subunit 3 | D | 2 | |
| 1569703_a_at | CORO1C | coronin, actin binding protein, 1C | I | 2 | yes |
| 205624_at | CPA3 | carboxypeptidase A3 (mast cell) | I | 2 | |
| 203532_x_at | CUL5 | cullin 5 | D | 2 | yes |
| 202434_s_at | CYP1B1 | cytochrome P450, family 1, subfamily B, polypeptide 1 | D | 2 | yes |
| 208281_x_at | DAZ1 | deleted in azoospermia 1 | I | 2 | |
| 209782_s_at | DBP | D site of albumin promoter (albumin D-box) binding protein | D | 2 | yes |
| 218943_s_at | DDX58 | DEAD box polypeptide 58 | I | 2 | yes |
| 240358_at | DENND3 | DENN/MADD domain containing 3 | I | 2 | |
| 1556769_a_at | DLGAP1 | discs, large (*Drosophila*) homolog-associated protein 1 | I | 2 | |
| 233052_at | DNAH8 | dynein, axonemal, heavy chain 8 | D | 2 | yes |
| 223371_s_at | DNAJC4 | DnaJ (Hsp40) homolog, subfamily C, member 4 | D | 2 | |
| 237311_at | DOCK1 | dedicator of cytokinesis 1 | D | 2 | yes |
| 244840_x_at | DOCK4 | dedicator of cytokinesis 4 | I | 2 | |
| 230207_s_at | DOCK5 | dedicator of cytokinesis 5 | I | 2 | |
| 225415_at | DTX3L | deltex 3-like (*Drosophila*) | I | 2 | |
| 210525_x_at | EFCAB11 | EF-hand calcium binding domain 11 | I | 2 | |
| 214313_s_at | EIF5B | eukaryotic translation initiation factor 5B | I | 2 | |
| 224727_at | EMC10 | ER membrane protein complex subunit 10 | D | 2 | |
| 217245_at | EPAG | early lymphoid activation protein | D | 2 | |
| 220874_at | EPB41 | erythrocyte membrane protein band 4.1 (elliptocytosis 1, RH-linked) | I | 2 | |
| 210870_s_at | EPM2A | epilepsy, progressive myoclonus type 2A, Lafora disease (laforin) | D | 2 | yes |
| 239979_at | EPSTI1 | epithelial stromal interaction 1 (breast) | I | 2 | |
| 1570371_a_at | EPT1 | ethanolaminephosphotransferase 1 (CDP-ethanolamine-specific) | D | 2 | |
| 227016_at | ERICH1 | glutamate-rich 1 | I | 2 | |
| 225764_at | ETV6 | ets variant 6 | I | 2 | yes |
| 214285_at | FABP3 | fatty acid binding protein 3, muscle and heart (mammary-derived growth inhibitor) | I | 2 | |
| 1557385_at | FAM161A | family with sequence similarity 161, member A | D | 2 | |
| 229543_at | FAM26F | family with sequence similarity 26, member F | I | 2 | |
| 216950_s_at | FCGR1A | Fc fragment of IgG, high affinity Ia, receptor (CD64) | I | 2 | yes |
| 1554360_at; 231302_at | FCHSD2 | FCH and double SH3 domains 2 | I | 2 | |
| 1553906_s_at | FGD2 | FYVE, RhoGEF and PH domain containing 2 | I | 2 | yes |
| 224002_s_at | FKBP7 | FK506 binding protein 7 | D | 2 | |
| 211454_x_at; 224288_x_at | FKSG49 | FKSG49 | I | 2 | |
| 226419_s_at | FLJ44342 | uncharacterized LOC645460 | I | 2 | |
| 228768_at | FNIP1 | folliculin interacting protein 1 | I | 2 | |
| 1556667_at | FONG | uncharacterized LOC348751 | D | 2 | |
| 242938_s_at | FOXK2 | forkhead box K2 | D | 2 | |
| 230645_at | FRMD3 | FERM domain containing 3 | I | 2 | |
| 230744_at | FSTL1 | follistatin-like 1 | D | 2 | |

TABLE 8-continued

Complete list of genes differentially expressed in the discovery cohort overlapping
between the intra-subject and inter-subject analyses (n = 246).

| Probe set ID | Gene Symbol | Gene Name | Change | Total CFG Score | Evidence or possible roles in apoptosis |
|---|---|---|---|---|---|
| 1563509_at; 224148_at | FYB | FYN binding protein | I | 2 | |
| 209416_s_at | FZR1 | fizzy/cell division cycle 20 related 1 (*Drosophila*) | D | 2 | yes |
| 202748_at; 242907_at | GBP2 | guanylate binding protein 2, interferon-inducible | I | 2 | |
| 229625_at | GBP5 | guanylate binding protein 5 | I | 2 | |
| 211060_x_at | GPAA1 | glycosylphosphatidylinositol anchor attachment protein 1 homolog (yeast) | D | 2 | |
| 237690_at | GPR115 | G protein-coupled receptor 115 | I | 2 | |
| 218468_s_at | GREM1 | gremlin 1 | I | 2 | yes |
| 235957_at | GRIP1 | glutamate receptor interacting protein 1 | I | 2 | |
| 213826_s_at | H3F3B | H3 histone, family 3B (H3.3B) | I | 2 | |
| 205221_at | HGD | homogentisate 1,2-dioxygenase | I | 2 | |
| 227614_at | HKDC1 | hexokinase domain containing 1 | D | 2 | |
| 210747_at | HLA-DQB1 | major histocompatibility complex, class II, DQ beta 1 | I | 2 | yes |
| 242001_at | IDH1 | isocitrate dehydrogenase 1 (NADP+), soluble | I | 2 | |
| 226757_at | IFIT2 | interferon-induced protein with tetratricopeptide repeats 2 | I | 2 | yes |
| 229450_at | IFIT3 | interferon-induced protein with tetratricopeptide repeats 3 | I | 2 | |
| 230128_at | IGLL5 | immunoglobulin lambda-like polypeptide 5 | I | 2 | |
| 225025_at | IGSF8 | immunoglobulin superfamily, member 8 | D | 2 | |
| 1562468_at | IL1RAP | interleukin 1 receptor accessory protein | I | 2 | yes |
| 207688_s_at | INHBC | inhibin, beta C | I | 2 | yes |
| 238725_at | IRF1 | interferon regulatory factor 1 | I | 2 | yes |
| 210119_at; 216782_at | KCNJ15 | potassium inwardly-rectifying channel, subfamily J, member 15 | I | 2 | |
| 231513_at; 206765_at | KCNJ2 | potassium inwardly-rectifying channel, subfamily J, member 2 | I | 2 | |
| 1559023_a_at | KIAA0494 | KIAA0494 | I | 2 | |
| 225193_at | KIAA1967 | KIAA1967 | D | 2 | yes |
| 208784_s_at | KLHDC3 | kelch domain containing 3 | D | 2 | |
| 1565690_at | KPNA3 | karyopherin alpha 3 (importin alpha 4) | I | 2 | |
| 208974_x_at | KPNB1 | karyopherin (importin) beta 1 | I | 2 | yes |
| 1555384_a_at | LARP4 | La ribonucleoprotein domain family, member 4 | D | 2 | |
| 215229_at | LOC100129973 | uncharacterized LOC100129973 | D | 2 | |
| 1569746_s_at | LOC100505783 | uncharacterized LOC100505783 | I | 2 | |
| 215322_at | LONRF1 | LON peptidase N-terminal domain and ring finger 1 | I | 2 | |
| 233818_at | LTN1 | listerin E3 ubiquitin protein ligase 1 | I | 2 | |
| 232283_at | LYSMD1 | LysM, putative peptidoglycan-binding, domain containing 1 | I | 2 | |
| 215902_at | MARCH 6 | membrane-associated ring finger (C3HC4) 6, E3 ubiquitin protein ligase | I | 2 | |
| 1554730_at | MCTP1 | multiple C2 domains, transmembrane 1 | I | 2 | |
| 235589_s_at | MDM4 | Mdm4 p53 binding protein homolog (mouse) | I | 2 | yes |
| 222567_s_at | MEX3C | mex-3 homolog C (*C. elegans*) | D | 2 | |
| 241541_at | MIB2 | mindbomb E3 ubiquitin protein ligase 2 | I | 2 | |
| 225826_at | MMAB | methylmalonic aciduria (cobalamin deficiency) cblB type | D | 2 | |
| 239273_s_at | MMP28 | matrix metallopeptidase 28 | D | 2 | yes |
| 221995_s_at | MRP63 | mitochondrial ribosomal protein 63 | I | 2 | |
| 228846_at | MXD1 | MAX dimerization protein 1 | I | 2 | yes |
| 211010_s_at | NCR3 | natural cytotoxicity triggering receptor 3 | D | 2 | yes |

TABLE 8-continued

Complete list of genes differentially expressed in the discovery cohort overlapping between the intra-subject and inter-subject analyses (n = 246).

| Probe set ID | Gene Symbol | Gene Name | Change | Total CFG Score | Evidence or possible roles in apoptosis |
|---|---|---|---|---|---|
| 243357_at | NEGR1 | neuronal growth regulator 1 | D | 2 | |
| 223218_s_at | NFKBIZ | nuclear factor of kappa light polypeptide gene enhancer in B-cells inhibitor, zeta | I | 2 | yes |
| 214101_s_at | NPEPPS | aminopeptidase puromycin sensitive | I | 2 | |
| 1557071_s_at | NUB1 | negative regulator of ubiquitin-like proteins 1 | I | 2 | yes |
| 1561847_at | NUDT17 | nudix (nucleoside diphosphate linked moiety X)-type motif 17 | D | 2 | |
| 1569990_at | NUDT3 | nudix (nucleoside diphosphate linked moiety X)-type motif 3 | I | 2 | |
| 243934_at | ODF3B | outer dense fiber of sperm tails 3B | I | 2 | |
| 229787_s_at | OGT | O-linked N-acetylglucosamine (GlcNAc) transferase | I | 2 | yes |
| 1569617_at | OSBP2 | oxysterol binding protein 2 | D | 2 | |
| 243287_s_at | OSTM1 | osteopetrosis associated transmembrane protein 1 | I | 2 | |
| 231838_at | PABPC1L | poly(A) binding protein, cytoplasmic 1-like | I | 2 | |
| 235157_at | PARP14 | poly (ADP-ribose) polymerase family, member 14 | I | 2 | |
| 227807_at | PARP9 | poly (ADP-ribose) polymerase family, member 9 | I | 2 | |
| 241956_at | PCGF5 | polycomb group ring finger 5 | I | 2 | |
| 222045_s_at | PCIF1 | PDX1 C-terminal inhibiting factor 1 | D | 2 | |
| 217695_x_at | PELI1 | pellino E3 ubiquitin protein ligase 1 | I | 2 | |
| 225958_at | PHC1 | polyhomeotic homolog 1 (*Drosophila*) | I | 2 | |
| 237867_s_at | PID1 | phosphotyrosine interaction domain containing 1 | D | 2 | |
| 216112_at | PKN2 | protein kinase N2 | I | 2 | yes |
| 241916_at | PLSCR1 | phospholipid scramblase 1 | I | 2 | yes |
| 235508_at | PML | promyelocytic leukemia | I | 2 | yes |
| 202884_s_at | PPP2R1B | protein phosphatase 2, regulatory subunit A, beta | D | 2 | yes |
| 1559119_at | PPP6R3 | protein phosphatase 6, regulatory subunit 3 | I | 2 | |
| 221270_s_at | QTRT1 | queuine tRNA-ribosyltransferase 1 | D | 2 | |
| 241320_at | R3HDM1 | R3H domain containing 1 | I | 2 | |
| 1553285_s_at | RAD9B | RAD9 homolog B (*S. pombe*) | I | 2 | |
| 202052_s_at | RAI14 | retinoic acid induced 14 | D | 2 | yes |
| 230466_s_at | RASSF3 | Ras association (RalGDS/AF-6) domain family member 3 | I | 2 | |
| 204927_at | RASSF7 | Ras association (RalGDS/AF-6) domain family (N-terminal) member 7 | D | 2 | |
| 237626_at | RB1CC1 | RB1-inducible coiled-coil 1 | I | 2 | yes |
| 232150_at | RBCK1 | RanBP-type and C3HC4-type zinc finger containing 1 | I | 2 | yes |
| 1560340_s_at | RP9P | retinitis pigmentosa 9 pseudogene | I | 2 | |
| 214041_x_at | RPL37A | ribosomal protein L37a | I | 2 | |
| 200908_s_at | RPLP2 | ribosomal protein, large, P2 | I | 2 | |
| 242625_at | RSAD2 | radical S-adenosyl methionine domain containing 2 | I | 2 | |
| 214370_at | S100A8 | S100 calcium binding protein A8 | I | 2 | yes |
| 242190_at | SDAD1 | SDA1 domain containing 1 | I | 2 | |
| 214257_s_at | SEC22B | SEC22 vesicle trafficking protein homolog B (*S. cerevisiae*) (gene/pseudogene) | I | 2 | |
| 223121_s_at | SFRP2 | secreted frizzled-related protein 2 | D | 2 | yes |
| 35626_at | SGSH | N-sulfoglucosamine sulfohydrolase | D | 2 | |
| 228527_s_at | SLC25A37 | solute carrier family 25 (mitochondrial iron transporter), member 37 | I | 2 | |
| 234268_at | SLC2A13 | solute carrier family 2 (facilitated glucose transporter), member 13 | I | 2 | |

TABLE 8-continued

Complete list of genes differentially expressed in the discovery cohort overlapping between the intra-subject and inter-subject analyses (n = 246).

| Probe set ID | Gene Symbol | Gene Name | Change | Total CFG Score | Evidence or possible roles in apoptosis |
|---|---|---|---|---|---|
| 235536_at | SNORD89 | small nucleolar RNA, C/D box 89 | I | 2 | |
| 208012_x_at; 209762_x_at | SP110 | SP110 nuclear body protein | I | 2 | |
| 228975_at | SP6 | Sp6 transcription factor | D | 2 | |
| 1557593_at | SPAG17 | sperm associated antigen 17 | D | 2 | |
| 202523_s_at | SPOCK2 | sparc/osteonectin, cwcv and kazal-like domains proteoglycan (testican) 2 | D | 2 | |
| 243522_at | SPPL3 | signal peptide peptidase like 3 | I | 2 | |
| 213562_s_at | SQLE | squalene epoxidase | D | 2 | |
| 219055_at | SRBD1 | S1 RNA binding domain 1 | I | 2 | |
| 1565566_a_at | STX7 | syntaxin 7 | I | 2 | |
| 1557305_at | TACC1 | transforming, acidic coiled-coil containing protein 1 | I | 2 | |
| 216226_at | TAF4B | TAF4b RNA polymerase II, TATA box binding protein (TBP)-associated factor, 105 kDa | D | 2 | |
| 231193_s_at | TAOK1 | TAO kinase 1 | I | 2 | yes |
| 225973_at | TAP2 | transporter 2, ATP-binding cassette, sub-family B (MDR/TAP) | I | 2 | |
| 221398_at | TAS2R8 | taste receptor, type 2, member 8 | I | 2 | |
| 213401_s_at | TBL1X | transducin (beta)-like 1X-linked | I | 2 | |
| 1566208_at | TCEA1 | transcription elongation factor A (SII), 1 | I | 2 | |
| 1552804_a_at | TIRAP | toll-interleukin 1 receptor (TIR) domain containing adaptor protein | D | 2 | yes |
| 224321_at | TMEFF2 | transmembrane protein with EGF-like and two follistatin-like domains 2 | I | 2 | |
| 235159_at | TMEM140; 243465_at | transmembrane protein 140 | I | 2 | |
| 238063_at | TMEM154 | transmembrane protein 154 | I | 2 | |
| 227386_s_at | TMEM200B | transmembrane protein 200B | I | 2 | |
| 1554206_at | TMLHE | trimethyllysine hydroxylase, epsilon | I | 2 | |
| 206025_s_at; 206026_s_at | TNFAIP6 | tumor necrosis factor, alpha-induced protein 6 | I | 2 | |
| 1555557_a_at | TNK2 | tyrosine kinase, non-receptor, 2 | D | 2 | |
| 1558354_s_at | TOP1 | topoisomerase (DNA) I | I | 2 | yes |
| 231978_at | TPCN2 | two pore segment channel 2 | I | 2 | |
| 223599_at | TRIM6 | tripartite motif containing 6 | I | 2 | |
| 242688_at | TRIP12 | thyroid hormone receptor interactor 12 | I | 2 | |
| 1565887_at | TRPM7 | transient receptor potential cation channel, subfamily M, member 7 | I | 2 | yes |
| 215107_s_at | TTC22 | tetratricopeptide repeat domain 22 | D | 2 | |
| 202476_s_at | TUBGCP2 | tubulin, gamma complex associated protein 2 | D | 2 | yes |
| 228588_s_at | UBE2B | ubiquitin-conjugating enzyme E2B | I | 2 | yes |
| 1568903_at | UBR5 | ubiquitin protein ligase E3 component n-recognin 5 | I | 2 | yes |
| 205586_x_at | VGF | VGF nerve growth factor inducible | D | 2 | |
| 242390_at | WDFY1 | WD repeat and FYVE domain containing 1 | I | 2 | |
| 201421_s_at | WDR77 | WD repeat domain 77 | D | 2 | |
| 1569428_at | WIBG | within bgcn homolog (Drosophila) | D | 2 | yes |
| 213734_at | WSB2 | WD repeat and SOCS box containing 2 | I | 2 | |
| 228617_at | XAF1 | XIAP associated factor 1 | I | 2 | yes |
| 1554037_a_at | ZBTB24 | zinc finger and BTB domain containing 24 | D | 2 | |
| 219062_s_at | ZCCHC2 | zinc finger, CCHC domain containing 2 | I | 2 | |
| 1555982_at | ZFYVE16 | zinc finger, FYVE domain containing 16 | I | 2 | |
| 228864_at | ZNF653 | zinc finger protein 653 | D | 2 | |

CD24, the top biomarker decreased in suicidal subjects of this Example, also has roles in apoptosis. Mice lacking CD24 show an increased rate of apoptosis (Duckworth C. A. et al., "CD24 is expressed in gastric parietal cells and regulates apoptosis and the response to *Helicobacter felis* infection in the murine stomach," American Journal of Physiology, Gastrointestinal and Liver Physiology 303, G915-926, doi:10.1152/ajpgi.00068.2012 (2012)). It could be that simpler mechanisms related to cellular survival and programed cell-death decision have been recruited by evolution for higher mental functions such as thoughts and behaviors leading to suicidality. In that sense, suicidality could be viewed as whole-organism self-poptosis. Interestingly, lithium, a medication with clinical evidence for preventing suicidality in bipolar disorder, has anti-apoptotic effects at a cellular level. Imaging studies have shown reduced gray matter volume in the brain of individuals with bipolar disorder and history of suicide attempts. Long-term lithium treatment was associated with increased gray matter volumes in the same areas where suicide was associated with decreased gray matter.

Taken together, the results of this Example have implications for the understanding of suicide, as well as for the development of objective laboratory tests and tools to diagnose and track suicidal risk and to monitor response to treatment.

More particularly, it was found that suicidality may be associated with dysphoric mood, as well as increased psychosis, anxiety and stress. SAT1 blood gene expression levels, in particular, showed a trend towards increase in low mood, high psychosis, high anxiety, and high stress in the bipolar subjects (see FIGS. 4A-4F).

Example 2

In this Example, SAT1 was validated by analyzing subsequent hospitalizations with and without suicidality and to previous hospitalizations with and without suicidality in two live follow-up cohorts, one bipolar (n=42) and one psychosis (schizophrenia/schizoaffective; n=46).

Particularly, the bipolar follow-up cohort (Table 9A) consisted of male Caucasian subjects in which whole-genome blood gene expression data, including levels of SAT1, were obtained at the testing visits as described in Example 1. If the subjects had multiple testing visits, the visit with the highest SAT1 level was selected for this analysis. The subjects' subsequent number of hospitalizations with or without suicidality was tabulated from electronic medical records.

The psychosis (schizophrenia/schizoaffective) follow-up cohort (n=46) (Table 9B) similarly consisted of Caucasian subjects in which whole-genome blood gene expression data, including levels of SAT1, were obtained at testing visits as described for the bipolar follow-up cohort. If the subjects had multiple testing visits, the visit with the highest SAT1 level was selected for this analysis. The subjects' subsequent number of hospitalizations with or without suicidality was tabulated from electronic medical records. A hospitalization was deemed to be without suicidality if suicidality was not listed as a reason for admission, and no suicidal ideation was described in the admission and discharge medical notes. Conversely, a hospitalization was deemed to be due to suicidality if suicidal acts or intent was listed as a reason for admission, and suicidal ideation was described in the admission and discharge medical notes.

TABLE 9A

Demographic Data for Live Bipolar Cohort (n = 42)

| SubjectID-Visit | Diagnosis | Age | Gender | Ethnicity | SAT1 Levels | Years since testing | Future Hosp. w/o suicidality | Future Hosp. due to suicidality | Frequency of Future Hosp. w/o suicidality | Frequency of Future Hosp. due to suicidality |
|---|---|---|---|---|---|---|---|---|---|---|
| phchp234v1 | Bipolar II Disorder | 44 | M | Caucasian | 1955.2 | 0.83 | 0 | 0 | 0 | 0 |
| phchp053v2 | Bipolar I Disorder | 58 | M | Caucasian | 2178.3 | 5.67 | 4 | 0 | 0.71 | 0 |
| phchp152v1 | Bipolar I Disorder | 45 | M | Caucasian | 2178.8 | 2.33 | 0 | 0 | 0 | 0 |
| phchp122v1 | Bipolar Disorder NOS | 51 | M | Caucasian | 2245.6 | 0.58 | 0 | 0 | 0 | 0 |
| phchp190v3 | Bipolar Disorder NOS | 50 | M | Caucasian | 2300.6 | 1.25 | 0 | 0 | 0 | 0 |
| phchp020v3 | Bipolar Disorder NOS | 63 | M | Caucasian | 2342.6 | 4.08 | 0 | 0 | 0 | 0 |
| phchp113v1 | Bipolar I Disorder | 37 | M | Caucasian | 2437.4 | 3.00 | 0 | 0 | 0 | 0 |
| phchp132v2 | Bipolar I Disorder | 51 | M | Caucasian | 2558.9 | 2.33 | 0 | 0 | 0 | 0 |
| phchp184v3 | Bipolar Disorder NOS | 64 | M | Caucasian | 2575.4 | 1.33 | 0 | 0 | 0 | 0 |
| phchp039v3 | Bipolar I Disorder | 52 | M | Caucasian | 2580.1 | 5.75 | 0 | 0 | 0 | 0 |
| phchp147v1 | Bipolar II Disorder | 38 | M | Caucasian | 2582.8 | 2.25 | 0 | 0 | 0 | 0 |
| phchp178v1 | Bipolar I Disorder | 49 | M | Caucasian | 2616.8 | 1.0 | 0 | 0 | 0 | 0 |
| phchp136v3 | Bipolar I Disorder | 41 | M | Caucasian | 2635.9 | 2.0 | 0 | 0 | 0 | 0 |
| phchp045v1 | Bipolar I Disorder | 36 | M | Caucasian | 2721.0 | 5.42 | 0 | 0 | 0 | 0 |
| phchp224v1 | Bipolar I Disorder | 59 | M | Caucasian | 2748.1 | 1.08 | 1 | 1 | 0.92 | 0.92 |
| phchp183v1 | Bipolar I Disorder | 48 | M | Caucasian | 2750.9 | 0.42 | 2 | 1 | 4.80 | 2.40 |

TABLE 9A-continued

Demographic Data for Live Bipolar Cohort (n = 42)

| SubjectID-Visit | Diagnosis | Age | Gender | Ethnicity | SAT1 Levels | Years since testing | Future Hosp. w/o suicidality | Future Hosp. due to suicidality | Frequency of Future Hosp. w/o suicidality | Frequency of Future Hosp. due to suicidality |
|---|---|---|---|---|---|---|---|---|---|---|
| phchp171v2 | Bipolar Disorder NOS | 36 | M | Caucasian | 2795.7 | 1.50 | 0 | 0 | 0 | 0 |
| phchp166v1 | Bipolar Disorder NOS | 56 | M | Caucasian | 2829.6 | 1.92 | 0 | 0 | 0 | 0 |
| phchp253v1 | Bipolar Disorder NOS | 25 | M | Caucasian | 2888.5 | 1.0 | 0 | 0 | 0 | 0 |
| phchp186v1 | Bipolar II Disorder | 43 | M | Caucasian | 2901.5 | 1.67 | 0 | 0 | 0 | 0 |
| phchp079v2 | Bipolar Disorder | 44 | M | Caucasian | 3053.2 | 4.50 | 0 | 0 | 0 | 0 |
| phchp128v1 | Bipolar I Disorder | 45 | M | Caucasian | 3118.6 | 2.67 | 0 | 0 | 0 | 0 |
| phchp080v1 | Bipolar I Disorder | 44 | M | Caucasian | 3153.6 | 5.00 | 0 | 0 | 0 | 0 |
| phchp088v1 | Bipolar I Disorder | 44 | M | Caucasian | 3194.1 | 4.58 | 0 | 10 | 0 | 2.18 |
| phchp109v1 | Bipolar I Disorder | 22 | M | Caucasian | 3200.8 | 3.00 | 1 | 2 | 0.33 | 0.67 |
| phchp134v3 | Bipolar II Disorder | 59 | M | Caucasian | 3202.3 | 1.92 | 0 | 0 | 0 | 0 |
| phchp153v1 | Bipolar II Disorder | 55 | M | Caucasian | 3304.9 | 2.0 | 0 | 0 | 0 | 0 |
| phchp274v2 | Bipolar Disorder NOS | 48 | M | Caucasian | 3349.0 | 0.50 | 0 | 0 | 0 | 0 |
| phchp140v3 | Bipolar II Disorder | 38 | M | Caucasian | 3393.8 | 1.92 | 0 | 0 | 0 | 0 |
| phchp030v3 | Bipolar I Disorder | 49 | M | Caucasian | 3395.2 | 5.92 | 0 | 3 | 0 | 0.51 |
| phchp124v1 | Bipolar I Disorder | 53 | M | Caucasian | 3660.9 | 2.50 | 0 | 6 | 0 | 2.40 |
| phchp095v3 | Bipolar I Disorder | 29 | M | Caucasian | 3695.4 | 0.33 | 0 | 1 | 0 | 3.00 |
| phchp100v1 | Bipolar I Disorder | 28 | M | Caucasian | 3767.8 | 1.58 | 0 | 0 | 0 | 0 |
| phchp210v3 | Bipolar I Disorder | 44 | M | Caucasian | 3844.6 | 0.50 | 0 | 0 | 0 | 0 |
| phchp219v1 | Bipolar Disorder NOS | 61 | M | Caucasian | 3845.1 | 1.17 | 0 | 0 | 0 | 0 |
| phchp031v3 | Bipolar I Disorder | 52 | M | Caucasian | 4080.7 | 4.08 | 1 | 0 | 0.24 | 0 |
| phchp093v3 | Bipolar I Disorder | 52 | M | Caucasian | 4137.4 | 2.67 | 0 | 1 | 0 | 0.38 |
| phchp067v1 | Bipolar II Disorder | 39 | M | Caucasian | 4214.7 | 5.58 | 0 | 0 | 0 | 0 |
| phchp142v3 | Bipolar I Disorder | 55 | M | Caucasian | 4310.7 | 1.92 | 0 | 0 | 0 | 0 |
| phchp112v2 | Bipolar I Disorder | 46 | M | Caucasian | 4410.4 | 1.33 | 0 | 0 | 0 | 0 |
| phchp149v2 | Bipolar Disorder NOS | 45 | M | Caucasian | 4586.9 | 2.00 | 1 | 0 | 0.5 | 0 |
| phchp117v1 | Bipolar I Disorder | 43 | M | Caucasian | 6531.1 | 3.00 | 0 | 0 | 0 | 0 |

TABLE 9B

Demographic Data for Live Psychosis Cohort (n = 46)

| SubjectID-Visit | Diagnosis | Age | Gender | Ethnicity | SAT1 Levels | Years since testing | Future Hosp. w/o suicidality | Future Hosp. due to suicidality | Frequency of Future Hosp. w/o suicidality | Frequency of Future Hosp. due to suicidality |
|---|---|---|---|---|---|---|---|---|---|---|
| phchp222v2 | Schizophrenia | 60 | M | Caucasian | 1410.6 | 0.67 | 0 | 0 | 0 | 0 |
| phchp175v1 | Schizoaffective Disorder | 42 | M | Caucasian | 1773.9 | 2.08 | 0 | 0 | 0 | 0 |
| phchp139v1 | Schizophrenia | 24 | M | Caucasian | 1774.6 | 0.25 | 0 | 0 | 0 | 0 |
| phchp025v1 | Schizophrenia | 42 | M | Caucasian | 2004.6 | 6.83 | 0 | 0 | 0 | 0 |
| phchp051v1 | Schizoaffective Disorder | 52 | M | Caucasian | 2083.8 | 5.83 | 0 | 0 | 0 | 0 |
| phchp148v1 | Schizophrenia | 25 | M | Caucasian | 2254.7 | 2.17 | 1 | 0 | 0.46 | 0 |
| phchp133v1 | Schizophrenia | 55 | M | Caucasian | 2286 | 2.75 | 0 | 2 | 0 | 0.73 |

TABLE 9B-continued

Demographic Data for Live Psychosis Cohort (n = 46)

| SubjectID-Visit | Diagnosis | Age | Gender | Ethnicity | SAT1 Levels | Years since testing | Future Hosp. w/o suicidality | Future Hosp. due to suicidality | Frequency of Future Hosp. w/o suicidality | Frequency of Future Hosp. due to suicidality |
|---|---|---|---|---|---|---|---|---|---|---|
| phchp033v1 | Schizoaffective Disorder | 48 | M | Caucasian | 2291.4 | 2.58 | 0 | 1 | 0 | 0.39 |
| phchp027v1 | Schizoaffective Disorder | 40 | M | Caucasian | 2406.3 | 6.67 | 3 | 0 | 0.45 | 0 |
| phchp012v1 | Schizoaffective Disorder | 55 | M | Caucasian | 2458.1 | 5.17 | 1 | 1 | 0.19 | 0.19 |
| phchp089v2 | Schizoaffective Disorder | 33 | M | Caucasian | 2545.3 | 4.42 | 0 | 0 | 0 | 0 |
| phchp060v1 | Schizophrenia | 62 | M | Caucasian | 2589.2 | 3.50 | 2 | 0 | 0.57 | 0 |
| phchp046v1 | Schizoaffective Disorder | 45 | M | Caucasian | 2732.3 | 6.17 | 0 | 1 | 0 | 0.16 |
| phchp103v1 | Schizoaffective Disorder | 61 | M | Caucasian | 2763.7 | 2.58 | 1 | 2 | 0.39 | 0.77 |
| phchp010v2 | Schizoaffective Disorder | 45 | M | Caucasian | 2778.5 | 6.92 | 0 | 0 | 0 | 0 |
| phchp005v1 | Schizoaffective Disorder | 45 | M | Caucasian | 2797.8 | 7.33 | 1 | 1 | 0.14 | 0.14 |
| phchp022v1 | Schizophrenia | 48 | M | Caucasian | 2846.6 | 6.83 | 0 | 0 | 0 | 0 |
| phchp195v3 | Schizophrenia | 53 | M | Caucasian | 2846.6 | 1.17 | 0 | 0 | 0 | 0 |
| phchp129v1 | Schizoaffective Disorder | 22 | M | Caucasian | 2871.5 | 2.83 | 5 | 1 | 1.76 | 0.35 |
| phchp120v1 | Delusional Disorder | 51 | M | Caucasian | 2877.9 | 3.00 | 0 | 0 | 0 | 0 |
| phchp211v1 | Schizophrenia | 62 | M | Caucasian | 2879.9 | 1.25 | 0 | 0 | 0 | 0 |
| phchp277v2 | Schizophrenia | 50 | M | Caucasian | 2904.8 | 0.58 | 0 | 0 | 0 | 0 |
| phchp101v1 | Schizoaffective Disorder | 74 | M | Caucasian | 2923.7 | 3.67 | 0 | 1 | 0 | 0.27 |
| phchp116v1 | Schizoaffective Disorder | 47 | M | Caucasian | 2962.1 | 0.50 | 0 | 1 | 0 | 2.00 |
| phchp052v1 | Schizophrenia | 60 | M | Caucasian | 2989.9 | 0.83 | 0 | 0 | 0 | 0 |
| phchp090v3 | Schizophrenia | 24 | M | Caucasian | 3046.4 | 1.00 | 0 | 2 | 0 | 2.00 |
| phchp197v1 | Schizophrenia | 56 | M | Caucasian | 3046.6 | 1.67 | 1 | 0 | 0.60 | 0 |
| phchp061v3 | Schizophrenia | 50 | M | Caucasian | 3115.6 | 4.92 | 1 | 6 | 0.20 | 1.22 |
| phchp057v1 | Schizoaffective Disorder | 47 | M | Caucasian | 3233.8 | 5.92 | 0 | 0 | 0 | 0 |
| phchp105v2 | Schizoaffective Disoder per chip | 59 | M | Caucasian | 3297.6 | 2.83 | 2 | 0 | 0.71 | 0 |
| phchp087v3 | Schizoaffective Disorder | 66 | M | Caucasian | 3523.5 | 4.25 | 0 | 0 | 0 | 0 |
| phchp091v1 | Schizoaffective Disorder | 55 | M | Caucasian | 3534.5 | 4.75 | 0 | 0 | 0 | 0 |
| phchp069v3 | Schizophrenia | 48 | M | Caucasian | 3819.8 | 5.25 | 0 | 0 | 0 | 0 |
| phchp062v3 | Schizophrenia | 57 | M | Caucasian | 3878.8 | 5.42 | 0 | 0 | 0 | 0 |
| phchp099v2 | Schizophrenia | 49 | M | Caucasian | 3993.4 | 3.58 | 0 | 0 | 0 | 0 |
| phchp049v1 | Schizoaffective Disorder | 46 | M | Caucasian | 4012.3 | 6.08 | 0 | 0 | 0 | 0 |
| phchp040v3 | Schizoaffective Disorder | 50 | M | Caucasian | 4019.2 | 5.25 | 1 | 0 | 0.19 | 0 |
| phchp042v3 | Schizoaffective Disorder | 44 | M | Caucasian | 4124.5 | 5.50 | 0 | 0 | 0 | 0 |
| phchp075v3 | Schizoaffective Disorder | 58 | M | Caucasian | 4127.1 | 4.83 | 1 | 5 | 0.21 | 1.03 |
| phchp108v2 | Schizophrenia | 42 | M | Caucasian | 4231.9 | 3.17 | 0 | 0 | 0 | 0 |
| phchp085v3 | Schizoaffective Disorder | 57 | M | Caucasian | 4335.9 | 4.50 | 0 | 0 | 0 | 0 |
| phchp151v3 | Schizophrenia | 24 | M | Caucasian | 4390.9 | 2.00 | 1 | 1 | 0.50 | 0.50 |
| phchp065v3 | Schizoaffective Disorder | 62 | M | Caucasian | 4439.2 | 5.25 | 0 | 0 | 0 | 0 |
| phchp086v3 | Schizophrenia | 49 | M | Caucasian | 4545.4 | 4.25 | 0 | 0 | 0 | 0 |
| phchp073v3 | Schizoaffective Disorder | 65 | M | Caucasian | 4874.4 | 4.92 | 0 | 12 | 0 | 2.44 |
| phchp072v3 | Schizoaffective Disorder | 60 | M | Caucasian | 5911.1 | 5.08 | 0 | 1 | 0 | 0.20 |

For future hospitalization analyses, robust multi-array analysis (RMA) as described in Example 1 was conducted and normalized for each cohort, prior to looking at biomarker levels in individual subjects. One-tail t-tests with equal variance were used for statistical comparisons. ROC curves were calculated using SPSS software for each of the four-dimensional analyses, predicting the state variable of hospitalizations due to suicidality.

Higher SAT1 levels compared to lower SAT1 levels at time of testing differentiated future as well as past hospitalizations due to suicidality in the bipolar disorder subjects (FIGS. 5A-5E). A similar, but weaker, pattern was exhibited in the psychosis (schizophrenia/schizoaffective) subjects (FIGS. 6A-6E). Remarkably, besides SAT1, three other biomarkers (PTEN, MARCKS and MAP3K3) of the six biomarkers that survived Bonferroni correction in the suicide completers cohort validation step also showed similar but weaker results (Table 10 and FIGS. 7A-7C).

TABLE 11

SAT1 Expression Level Cut-offs from the ROC Curve (FIGS. 8A-8C)

| Cut-off | SAT1 Expression Levels | Sensitivity | Specificity | Accuracy |
|---|---|---|---|---|
| Higher Sensitivity | 2723.512 | 100.00% | 41.18% | 70.59% |
| Intermediate | 3173.874 | 75.00% | 61.76% | 68.38% |
| Higher Specificity | 3394.539 | 50.00% | 73.53% | 61.77% |

Figures 9A, 9B:
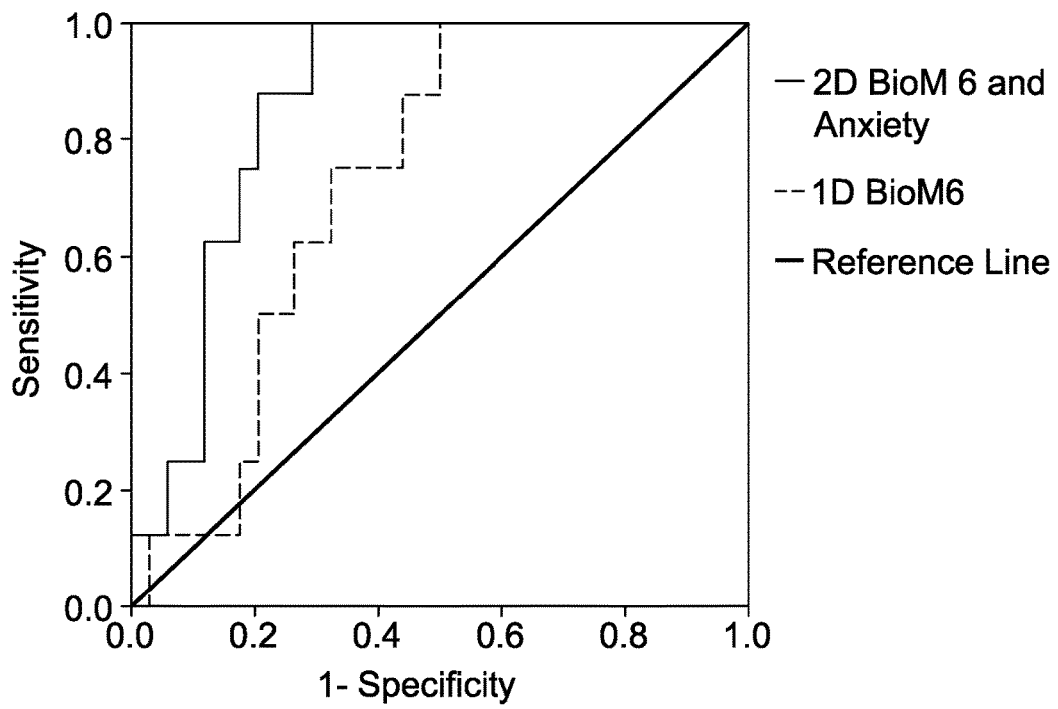
FIGS. 9A and 9B depict multi-dimensional prediction of future psychiatric hospitalizations due to suicidality as analyzed in Example 2. Data in each dimension was normalized to a 0-100 scale (with the mood VAS scale inverted, as the assumption was made that depressed mood states would more closely correlate with suicidality). The angle between dimensions was assumed to be 90 degrees, and a simple Pythagorean distance from origin score was calculated. The distribution of this score in the test cohort was used to generate an ROC curve for hospitalizations due to suicidality.

The multi-dimensional approach described above for SAT1 was also conducted to predict future hospitalizations, by adding data about mood, anxiety, and psychosis to the data about the six top biomarkers' expression levels (BioM 6, including the biomarkers SAT1, PTEN, MARCKS, MAP3K3, UBA6, and MT-ND6; FIGS. 9A-9B).

TABLE 10

Prospective and Retrospective Differentiation of Hospitalizations and Suicidality

| | Bipolar Disorder (n = 42) | | | | Psychosis (n = 46) Schizophrenia/Schizoaffective | | | |
|---|---|---|---|---|---|---|---|---|
| | Future Hospitalizations (since testing) | | Past Hospitalizations (prior to testing) | | Future Hospitalizations (since testing) | | Past Hospitalizations (prior to testing) | |
| | Without | With Suicidality | Without | With Suicidality | Without | With Suicidality | Without | With Suicidality |
| SAT1 | NS | H: 0.1195 T: 0.0484 | NS | H: 0.0743 T: 0.0363 | NS | NS (H: 0.0519) | NS | H: 0.0274 T: 0.0742 |
| PTEN | NS | H: 0.0271 T: 0.0324 | NS | H: 0.0598 T: 0.0491 | NS | NS | NS | NS |
| MARCKS | NS | NS | NS | H: 0.0227 T: 0.0242 | NS | NS | NS | NS |
| MAP3K3 | NS | NS | NS | H: 0.2052 T: 0.0273 | NS | NS | NS | NS |
| UBA6 | NS | NS | NS | NS | NS | NS | NS | NS |
| MT-ND6 | NS | NS | NS | NS | NS | NS | NS | NS |
| Panel of 3 (SAT1, PTEN, MAP3K3) | NS | H: 0.0184 T: 0.0530 | NS | H: 0.04905 T: 0.04914 | NS | NS | NS | NS |
| Panel of 6 (SAT1, PTEN, MAP3K3, UBA6, MARCK, MT-ND6) | NS | H: 0.1501 T: 0.0159 | NS | H: 0.0728 T: 0.0101 | NS | NS | NS | NS |

Taken together, the prospective and retrospective hospitalization data suggests SAT1, PTEN, MARCKS and MAP3K3 may be not only a state marker but perhaps a trait marker as well.

A multi-dimensional approach was also conducted to predict future hospitalizations, by adding data about mood, anxiety, and psychosis to the data about SAT1 expression levels (FIGS. 8A-8C). The ROC curve improved in a step-wise fashion, from an AUC of 0.640 with SAT1 alone, to an AUC of 0.798 with SAT1 and anxiety, an AUC of 0.813 with SAT1, anxiety and mood, and an AUC of 0.835 with SAT1, anxiety, mood and psychosis. Levels of SAT1 were identified that provided different levels of sensitivity and specificity (Table 11). The anxiety and mood information was obtained from simple visual analog scales, previously described in Niculescu, et al., "PhenoChipping of psychotic disorders: a novel approach for deconstructing and quantitating psychiatric phenotypes. *American Journal of Medical Genetics. Part B, Neuropsychiatric genetics: the official publication of the International Society of Psychiatric Genetics* 141B, 653-662, doi:10.1002/ajmg.b.30404 (2006).

These results demonstrate that combining clinical scale data for anxiety and mood with the blood biomarker date improves predictability of increased suicide ideation and/or future hospitalization.

The psychosis information was based on combining of the scores on the hallucinations and delusions in the PANSS (FIG. 10). Of note, this simple clinical-genomic approach did not directly ask about suicidal ideation, which some individuals may deny or choose not to share with clinicians.

Using discovery in live subjects and validation in suicide completers, possible biomarkers for suicidality were found. The top biomarker finding, SAT1, as well as PTEN, MARCKS and MAP3K3, were additionally validated by prospective and retrospective analyses in live subjects, looking at ability to predict and differentiate future and past hospitalizations due to suicidality in bipolar disorder and psychosis (schizophrenia/schizoaffective) (Table 10).

Beyond predictions, as a window into the biology of suicidality, the current Examples show overlap at a gene and pathway level with apoptosis. SAT1, for example, is a key catabolic enzyme for polyamines Polyamine levels within cells control cell viability, and significant decreases in polyamine levels can result in apoptosis. They seem to reflect an endowment for cellular and organismal activity and growth, key characteristics of mood. SAT1, which is increased in live suicidal ideation subjects and in suicide completers in the Examples, is highly inducible by a variety of stimuli, including toxins, cytokines, heat shock, ischemia, and other stresses. SAT1 overexpressing mice had alterations in their polyamine pool, hair loss, infertility and weight loss (Pietila et al., Activation of polyamine catabolism profoundly alters tissue polyamine pools and affects hair growth and female fertility in transgenic mice overexpressing spermidine/spermine N1-acetyltransferase. J Biol. Chem. 272, 18746-18751 (1997); Min et al., Altered levels of growth-related and novel gene transcripts in reproductive and other tissues of female mice overexpressing spermidien/spermine N1-actyltransferase (SSAT). J. Biol. Chem. 277, 3647-3657, doi:10.1074/jbc.M100751200 (2002)). Turecki and colleagues have provided compelling evidence for changes in the polyamine system in the brain of suicide completers (Fiori et al., Global gene expression profiling of the polyamine system in suicide completers. Int. J. Neuropsychopharmacol. 14, 595-605, doi:10.1017/S1461145710001574 (2011)).

CD24, the top biomarker found to decrease in suicidal subjects, also has roles in apoptosis. Specifically, mice lacking CD24 showed an increased rate of apoptosis (Duckworth et al. CD24 is expressed in gastric parietal cells and regulates apoptosis and the response to *Helicobacter felis* infection in the murine stomach. American Journal of Physiology. Gastrointestinal and liver physiology 303, G915-926, doi:10.1152/ajpgi.00068.2012 (2012)).

It could be that simpler mechanisms related to cellular survival and programed cell-death decision have been recruited by evolution for higher mental functions such as feelings, thoughts, actions and behaviors leading to suicidality. In that sense, suicidality could be viewed as whole-organism self-apoptosis. Apoptosis mechanisms have previously been implicated in mood disorders, and their inhibition in affective resilience (Malkesman et al. Targeting the BH3-interacting domain death agonist to develop mechanistically unique antidepressants. Mol. Psychiatry 17, 770-780, doi:10.1038/mp.2011.77 (2012)). Interestingly, lithium, a medication with clinical evidence for preventing suicidality in bipolar disorder, has anti-apoptotic effects at a cellular level (Lowthert et al., Increased ratio of anti-apoptotic to pro-apoptotic Bcl2 gene-family members in lithium-responders one month after treatment initiation. Biology of Mood & Anxiety Disorders 2, 15, doi:10.1186/2045-5380-2-15 (2012)). Imaging studies have shown reduced gray matter volume in the brain of individuals with bipolar disorder and history of suicide attempts. Long-term lithium treatment was associated with increased gray matter volumes in the same areas where suicide was associated with decreased gray matter (Benedetti et al., Opposite effects of suicidality and lithium on gray matter volumes in bipolar depression. J Affect Disord 135, 139-147, doi:10.1016/j.jad.2011.07.006 (2011)).

In view of the above, it will be seen that the several advantages of the disclosure are achieved and other advantageous results attained. As various changes could be made in the above methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A method for assessing and mitigating suicidality in a male bipolar subject in need thereof, comprising:
   determining an expression level of at least a first panel of blood biomarkers or a second panel of blood biomarkers in a sample from the subject, where the first panel of blood biomarkers comprises small cell lung carcinoma cluster 4 antigen (CD24; CD24 molecule), ATPase type 13A2 (ATP13A2), epoxide hydrolase 1, microsomal (xenobiotic) (EPHX1), HtrA serine peptidase 1 (HTRA1); leptin receptor (LEPR), spectrin beta non-erythrocytic 1 (SPTBN1), muscleblind-like 2 (MBNL2), olfactory receptor family 2 subfamily J member 3 (OR2J3), Ras homolog enriched in brain (RHEB), and where the second panel of blood biomarkers comprises spermidine/spermine N1-acetyltransferase 1 (SAT1); forkhead box N3 (FOXN3), guanylate binding protein 1 (GBP1), phosphoinositide-3-kinase regulatory subunit 5 (PIK3R5), apolipoprotein L2 (APOL2), ATPase H+ transporting lysosomal 9 kDa, VO subunit el (ATP6V0E1), GRINL1A complex locus (GCOM1), interleukin 1 beta (IL1B), lipoma HMGIC fusion partner (LHFP), lipase A (LIPA), myristoylated alanine-rich protein kinase C substrate (MARCKS), 6-phosphogluconolactonase (PGLS), phosphatase and tensin homolog (PTEN), reversion-inducing-cysteine-rich protein with kazal motifs (RECK), tumor necrosis factor (ligand) superfamily member 10 (TNFSF1O), ATP-binding cassette, subfamily A (ABCl) member 1 (ABCA1), Rho guanine nucleotide exchange factor (GEF) 40 (ARHGEF4; FLJ10357), cancer susceptibility candidate 1 (CASC1), dehydrogenase/reductase (SDR family) member 9 (DHRS9), disrupted in schizophrenia 1 (DISC1), eukaryotic translation initiation factor 2-alpha kinase 2 (EIF2AK2), uncharacterized LOC727820 (LOC727820), mitogen-activated protein kinase kinase kinase 3 (MAP3K3), mitochondrially encoded NADH dehydrogenase 6 (MT-ND6; ND6), RNA binding motif protein 47 (RBM47), RPTOR independent companion of MTOR complex 2 (RICTOR), sterile alpha motif domain containing 9-like (SAMD9L), scavenger receptor class F member 1 (SCARF1), solute carrier family 36 (proton/amino acid symporter) member 1 (SLC36A1), signal transducer and activator of transcription 1, 91 kDa (STAT1), cytochrome c oxidase subunit Vb (COX5B), SWI/SNF related matrix associated actin dependent regulator of chromatin subfamily a member 1 (SMARCA1), ubiquitin-like modifier activating enzyme 6 (UBA6), zinc finger CCCH-type antiviral 1 (ZC3HAV1) and tyrosine kinase, non-receptor 2 (TNK2);
   identifying a subject having suicidality where the expression level of the blood biomarkers in the first panel is decreased relative to a reference expression level, or, the expression level of the blood biomarkers in the second panel is increased relative to a reference expression level; and,
   administering to the subject identified as having suicidality a drug to treat the suicidality.

2. The method according to claim 1, where the identifying step further comprises comparing a biomarker panel score of the subject to a biomarker panel score of a reference.

3. The method according to claim 1, wherein: (a) individuals who have changes in one or more of SPTBN1, MBNL2, S100A8 are treated with clozapine; and (b) individuals who have changes in one or more of SAT1, GBP1, IL1B, LHFP, MAP3K3, S100A8 are treated with docosahexaenoic acid (DHA).

* * * * *